(12) United States Patent
Ashworth-Sharpe et al.

(10) Patent No.: US 12,130,284 B2
(45) Date of Patent: Oct. 29, 2024

(54) COLORS FOR CHROMOGENIC IHC AND ISH STAINING WITH MULTI-DYE QUINONE METHIDE AND TYRAMIDE CONJUGATES

(71) Applicant: Ventana Medical Systems, Inc., Tucson, AZ (US)

(72) Inventors: Julia Ashworth-Sharpe, Tucson, AZ (US); Brian D. Kelly, Tucson, AZ (US); Mark Lefever, Oro Valley, AZ (US); Nathan W. Polaske, Oracle, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 346 days.

(21) Appl. No.: 17/318,541

(22) Filed: May 12, 2021

(65) Prior Publication Data

US 2021/0341466 A1    Nov. 4, 2021

Related U.S. Application Data

(60) Division of application No. 16/226,427, filed on Dec. 19, 2018, now Pat. No. 11,143,648, which is a continuation of application No. PCT/EP2017/065795, filed on Jun. 27, 2017.

(51) Int. Cl.
| | |
|---|---|
| *G01N 33/533* | (2006.01) |
| *C09B 11/24* | (2006.01) |
| *C09B 23/08* | (2006.01) |
| *G01N 33/532* | (2006.01) |
| *G01N 33/58* | (2006.01) |

(52) U.S. Cl.
CPC ............ *G01N 33/533* (2013.01); *C09B 11/24* (2013.01); *C09B 23/083* (2013.01); *G01N 33/532* (2013.01); *G01N 33/582* (2013.01); *G01N 33/583* (2013.01)

(58) Field of Classification Search
CPC .. G01N 33/583; G01N 33/533; G01N 33/582; G01N 33/532; C09B 11/24; C09B 23/083; C09B 69/106; C09B 69/109
See application file for complete search history.

(56) References Cited

U.S. PATENT DOCUMENTS

| | | |
|---|---|---|
| 2007/0009980 A1 | 1/2007 | Graham |
| 2008/0293164 A1 | 11/2008 | Gaylord et al. |
| 2012/0171668 A1 | 7/2012 | May et al. |

FOREIGN PATENT DOCUMENTS

| | | | |
|---|---|---|---|
| WO | 2000014545 A1 | 3/2000 | |
| WO | 2003067210 A2 | 8/2003 | |
| WO | 2010111674 A2 | 9/2010 | |
| WO | WO-2015124703 A1 * | 8/2015 | ............ C07D 209/14 |

OTHER PUBLICATIONS

Gnaim et al. Quinone-Methide Species, A Gateway to Functional Molecular Systems: From Self-Immolative Dendrimers to Long-Wavelength Fluorescent Dyes. Gnaim et al. Acc. Chem. Res. 2014, vol. 47, pp. 2970-2984. (Year: 2014).*
Lebel Réjean et al: "Impact of H-aggregation on activatable MMP-2specific probes for optical imaging", Contrast Media & Molecular Imaging, vol. 7, No. 3, 2012, pp. 328-337.
Steven H L Verhelst et al: "A Mild Chemically Cleavable Linker System for Functional Proteomic Applications", Angewandte Chemie International Edition, vol. 46, No. 8, 2007, pp. 1284-1286.
Karunakaran A. Kalesh et al: "Peptide-based activity-based probes (ABPs) f_or target-specific profiling of protein tyrosine phosphatases (PTPs)", Chemical Communications, vol. 46, No. 4, 2010, p. 589.
Jonathan D. Sellars et al: "Fluorescence quenched quinone methide based activity probes—a cautionary tale", Organic & Biomolecular Chemistry, vol. 8, No. 7, 2010, p. 1610.
Toru Komatsu et al: "Design and Synthesis of an Enzyme ActivityBased Labeling Molecule with Fluorescence Spectral Change", Journal of the American Chemical Society, vol. 128, No. 50, 2006, pp. 15946-15947.
Chen Bifeng et al: "Chemoselective reduction and self-immolation based FRET probes for detecting hydrogen sulfide in solution and in cells", Organic & Biomolecular Chemistry, vol. 12, No. 30, 2014, p. 5629.
Zhu O et al: "Activity-based fluorescent probes that target phosphatases", Tetrahedron Letters, vol. 44, No. 13, 2003, pp. 2669-2672.
Nathan W Polaske et al: "Quinone Methide Signal Amplification: Covalent Reporter Labeling of Cancer Epitopes using Alkaline Phosphatase Substrates", Bioconjugate Chemistry, vol. 27, No. 3, Jan. 19, 2016, pp. 660-666.

* cited by examiner

*Primary Examiner* — Shafiqul Haq
(74) *Attorney, Agent, or Firm* — Charney IP Law LLC; Thomas M. Finetti

(57) ABSTRACT

Disclosed herein are novel chromogenic conjugates, the conjugates comprising at least two detectable moieties.

21 Claims, 14 Drawing Sheets

COLORS FOR CHROMOGENIC IHC AND ISH STAINING WITH MULTI-DYE QUINONE METHIDE AND TYRAMIDE CONJUGATES

CROSS REFERENCE TO RELATED APPLICATIONS

This application is a divisional of U.S. patent application Ser. No. 16/226,427 filed on Dec. 19, 2018, which application is a continuation of PCT/EP2017/065795, filed Jun. 27, 2017, which claims the benefit of U.S. Provisional Application No. 62/355,398, filed Jun. 28, 2016, the content of each of which is incorporated herein by reference in its entirety.

BACKGROUND OF THE DISCLOSURE

Filed of the Invention

The present disclosure relates to the field of chemistry and diagnostics.

Description of the Related Art

Immunohistochemistry (IHC) refers to the processes of detecting, localizing, and/or quantifying antigens, such as a protein, in a biological sample using antibodies specific to the particular antigens. IHC provides the substantial advantage of identifying exactly where a particular protein is located within the tissue sample. It is also an effective way to examine the tissues themselves. In situ hybridization (ISH) refers to the process of detecting, localizing, and quantifying nucleic acids. Both IHC and ISH can be performed on various biological samples, such as tissue (e.g. fresh frozen, formalin fixed, paraffin embedded) and cytological samples. Recognition of the targets can be detected using various labels (e.g., chromogenic, fluorescent, luminescent, radiometric), irrespective of whether the target is a nucleic acid or an antigen. To robustly detect, locate, and quantify targets in a clinical setting, amplification of the recognition event is desirable as the ability to confidently detect cellular markers of low abundance becomes increasingly important for diagnostic purposes. For example, depositing at the marker's site hundreds or thousands of label molecules in response to a single antigen detection event enhances, through amplification, the ability to detect that recognition event.

Adverse events often accompany amplification, such as non-specific signals that are apparent as an increased background signal. An increased background signal interferes with the clinical analysis by obscuring faint signals that may be associated with low, but clinically significant, expressions. Accordingly, while amplification of recognition events is desirable, amplification methods that do not the increase background signal are highly desirable. One such method is Tyramide Signal Amplification (TSA), which has also been referred to as catalyzed reporter deposition (CARD). U.S. Pat. No. 5,583,001 discloses a method for detecting and/or quantitating an analyte using an analyte-dependent enzyme activation system that relies on catalyzed reporter deposition to amplify the detectable label signal. Catalysis of an enzyme in a CARD or TSA method is enhanced by reacting a labeled phenol molecule with an enzyme. Modern methods utilizing TSA effectively increase the signals obtained from IHC and ISH assays while not producing significant background signal amplification (see, for example, U.S. application publication No. 2012/0171668 which is hereby incorporated by reference in its entirety for disclosure related to tyramide amplification reagents). Reagents for these amplification approaches are being applied to clinically important targets to provide robust diagnostic capabilities previously unattainable (VENTANA OptiView Amplification Kit, Ventana Medical Systems, Tucson AZ, Catalog No. 760-099).

TSA takes advantage of the reaction between horseradish peroxidase (HRP) and tyramide. In the presence of $H_2O_2$, tyramide is converted to a highly-reactive and short-lived radical intermediate that reacts preferentially with electron-rich amino acid residues on proteins. Covalently-bound detectable labels can then be detected by variety of chromogenic visualization techniques and/or by fluorescence microscopy. In solid-phase immunoassays, such as IHC and ISH, where spatial and morphological context is highly valued, the short lifetime of the radical intermediate results in covalent binding of the tyramide to proteins on tissue in close proximity to the site of generation, giving discrete and specific signal.

Co-pending application PCT/EP2015/053556 entitled "Quinone Methide Analog Signal Amplification," having an international filing date of Feb. 20, 2015, describes an alternative technique ("QMSA") that, like TSA, may be used to increase signal amplification without increasing background signals. Indeed, PCT/EP2015/053556 describes novel quinone methide analog precursors and methods of using the quinone methide analog precursors in detecting one or more targets in a biological sample. There, the method of detection is described as comprising the steps of contacting the sample with a detection probe, then contacting the sample with a labeling conjugate that comprises an enzyme. The enzyme interacts with a quinone methide analog precursor comprising a detectable label, forming a reactive quinone methide analog, which binds to the biological sample proximally to or directly on the target. The detectable label is then detected.

BRIEF SUMMARY OF THE DISCLOSURE

In one aspect of the present disclosure is a multi-dye conjugate comprising a tissue reactive moiety and at least two chromophores, wherein the tissue reactive moiety is selected from the group consisting of a quinone methide precursor or a tyramide or a derivative thereof, and wherein the at least two chromophores allow for the multi-dye conjugate to display or produce a color or signal different than either of the at least two chromogens individually.

In some embodiments, the at least two chromophores are selected, without limitation, from the group consisting of Rhodamine 800, TAMRA, Dabsyl, Cy5, Dabcyl, Cy3, Cy7, Cy3.5, CyB, Cy5.5, and fluorescein. In some embodiments, the multi-dye conjugate displays a color (or signal) different than a color (or signal) of either of the at least two chromophores.

In some embodiments, the at least two chromophores are conjugated to the tissue reactive moiety through a multifunctional linker. In some embodiments, the multi-functional linker is a heterobifunctional linker. In some embodiments, the heterobifunctional linker is lysine or a derivative thereof. In some embodiments, the multi-functional linker is a dendrimer. In some embodiments, the dendrimer is selected from the group consisting of polyamidoamine (PA-MAM) dendrimers, Janus dendrimers, and bis-MPA dendrimers.

In some embodiments, the multi-functional linker is selected from the group consisting of norspermidine and spermine. In some embodiments, the multi-functional linker comprises a molecular weight of between about 50 g/mol and about 300 g/mol. In some embodiments, a first of the at least two chromophores is conjugated directly or indirectly to the tissue reactive moiety, and a second of the at least two chromophores is conjugated directly or indirectly to the first chromophore.

In another aspect of the present disclosure is a multi-dye conjugate having Formula (I)

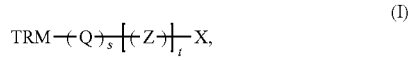

wherein

"TRM" is a tissue reactive moiety (e.g. a quinone methide precursor, a tyramide, or a tyramide derivative, such as further disclosed herein); Q is a branched or unbranched, linear or cyclic, substituted or unsubstituted group having between 2 and 40 carbon atoms, and optionally having one or more heteroatoms selected from O, N, or S; Z is a bond, or a branched or unbranched, linear or cyclic, substituted or unsubstituted, saturated or unsaturated, group having between 2 and 20 carbon atoms, and optionally having one or more heteroatoms selected from O, N, or S; X is H, $-[(Q)_d-[A]_n]_e$; $-N-([Z]-[X])_2$; or $-C(H)([Z]-[X])_2$; A is a detectable moiety (e.g. a chromogen); d is 0 or 1; e is an integer ranging from 1 to 4; s is 0 or an integer ranging from 1 to 4; and t is 0 or an integer ranging from 1 to 10; provided that the multi-dye conjugate comprises at least two A groups (e.g. two chromogens).

In some embodiments, TRM has the structure of Formula (II):

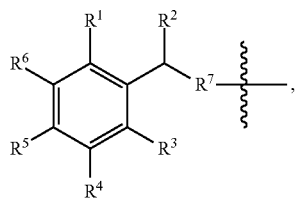

wherein $R^1$ is selected from the group consisting of phosphate, amide, nitro, urea, sulfate, methyl, ester, beta-lactam, and a sugar; $R^2$ is a halide; $R^3$, $R^4$, $R^5$, and $R^6$ are independently selected from hydrogen or an aliphatic group having between 1 and 4 carbon atoms; and $R^7$ is $-(CH_2)_wNH-$, $-O(CH_2)_wNH-$, $-N(H)C(O)(CH_2)_wNH-$, $-C(O)N(H)(CH_2)_wNH-$, $-(CH_2)_wO-$, $-O(CH_2)_wO-$, $-O(CH_2CH_2O)_w-$, $-N(H)C(O)(CH_2)_wO-$, $-C(O)N(H)(CH_2)_wO-$, $-C(o)N(H)(CH_2CH_2O)_w-$, $-(CH_2)_wS-$, $-O(CH_2)_wS-$, $-N(H)C(O)(CH_2)_wS-$, $-C(O)N(H)(CH_2)_wS-$, $-(CH_2)_wNH-$, $-C(O)N(H)(CH_2CH_2O)_wCH_2CH_2NH$, $-C(O)(CH_2CH_2O)_wCH_2CH_2NH-$, $-C(O)N(H)(CH_2)NHC(O)CH(CH_3)(CH_2)_wNH-$, or $-N(H)(CH_2)_wNH-$, where w is an integer ranging from 1 to 12.

In some embodiments, TRM has the structure of Formula (IIc):

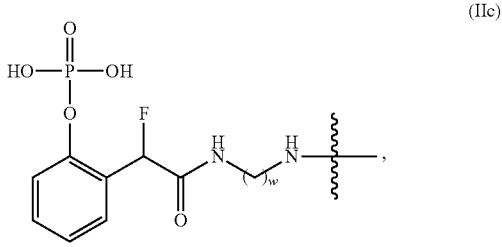

wherein w ranges from 1 to 12. In some embodiments, w ranges from 2 to 6.

In some embodiments, TRM is a tyramide or a tyramide derivative.

In some embodiments, Q has the structure of Formula (IVa)

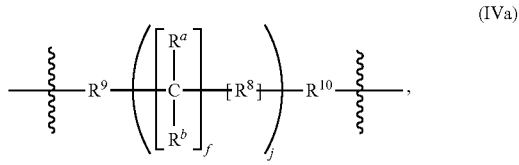

wherein f is 0, 1, or 2; $R^8$ is a bond, O, S, or $N(R^c)(R^d)$; $R^a$ and $R^b$ are independently H, a $C_1$-$C_4$ alkyl group, F, Cl, or $-N(R^c)(R^d)$; $R^c$ and $R^d$ are independently selected from $CH_3$ or H; $R^9$ and $R^{10}$ are independently a bond or a group selected from carbonyl, amide, imide, ester, ether, amine, thione, thiol; and j is an integer ranging from 1 to 8.

In some embodiments, Q has the structure of Formula (IVb):

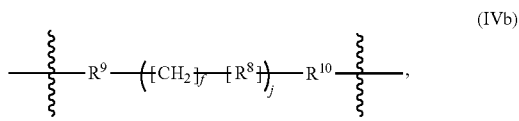

wherein f is 0, 1, or 2; $R^8$ is a bond, O, S, or $N(R^c)(R^d)$; $R^c$ and $R^d$ are independently $CH_3$ or H; $R^9$ and $R^{10}$ are independently a bond or a group selected from carbonyl, amide, imide, ester, ether, amine, or thiol; and j is an integer ranging from 1 to 8.

In some embodiments, Z has the structure of Formula (Va):

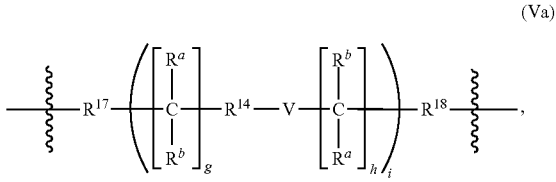

wherein $R^{17}$ and $R^{18}$ are independently a bond or a group selected from carbonyl, amide, imide, ester, ether, —NH, —N—, thione, or thiol; $R^{14}$ is a bond, a carbonyl, an imine, or a thione; V is a bond, —$C(R^{15})(R^{16})$—, —O—, —S—, —$N(R^{16})$—, —N(X)—; —$C(R^{15})(X)$; —$C(X)_2$—, or —$C(R^{15})(N(R^{16})(X))$; X is as defined herein; $R^a$ and $R^b$ are independently H, a $C_1$-$C_4$ alkyl group, F, Cl, or $N(R^{15})(R^{16})$; $R^{15}$ and $R^{16}$ are independently a bond or —$CH_3$ or H; g is 0 or an integer ranging from 1 to 4; h is 0 or an integer ranging from 1 to 8; and i is 1 or 2.

In some embodiments, g is 0, $R^{14}$ is a carbonyl, V is —$C(R^{15})(N(R^{16})(X))$, $R^{15}$ is H, $R^{16}$ is H, and h ranges from 2 to 6. In some embodiments, g is 0, $R^{14}$ is a carbonyl, V is —$C(R^{15})(N(R^{16})(X))$, $R^{15}$ is H, $R^{16}$ is H, and h ranges from 2 to 4. In some embodiments, g is 0, $R^{14}$ is a carbonyl, V is —$C(R^{15})(N(R^{16})(X))$, $R^{15}$ is H, $R^{16}$ is H, and h is 4. In some embodiments, g is 0, $R^{14}$ is a carbonyl, V is —$C(R^{15})(N(R^{16})(X))$, $R^{15}$ is H, $R^{16}$ is H, $R^a$ and $R^b$ are H, and h ranges from 2 to 4. In some embodiments, g is 0, $R^{14}$ is a carbonyl, V is —$C(R^{15})(N(R^{16})(X))$, $R^{15}$ is H, $R^{16}$ is H, $R^a$ and $R^b$ are H, $R^9$ is a bond, $R^{10}$ is an amine; and h ranges from 2 to 4. In some embodiments, g is 0, $R^{14}$ is a carbonyl, V is —$C(R^{15})(N(R^{16})(X))$, $R^{15}$ is H, $R^{16}$ is H, $R^a$ and $R^b$ are H, $R^9$ is a bond, $R^{10}$ is an amine; X is -$[(Q)_d$-$[A]_n]_e$, d, n, and e are each 1, and h ranges from 2 to 4.

In some embodiments, the multi-dye conjugate has the structure:

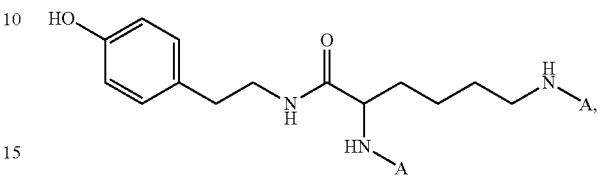

where A is a detectable moiety. In some embodiments, each A group comprises a different detectable moiety.

In some embodiments, the multi-dye conjugate has the structure:

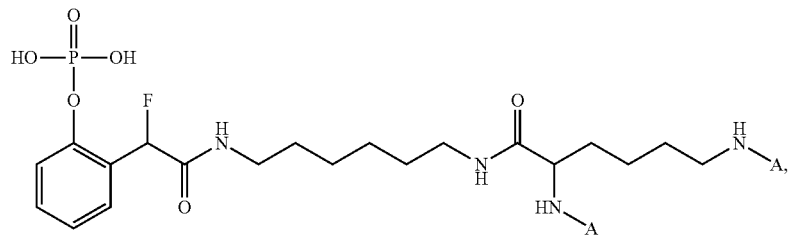

where A is a detectable moiety. In some embodiments, each A group comprises a different detectable moiety.

In some embodiments, the multi-dye conjugate has the structure:

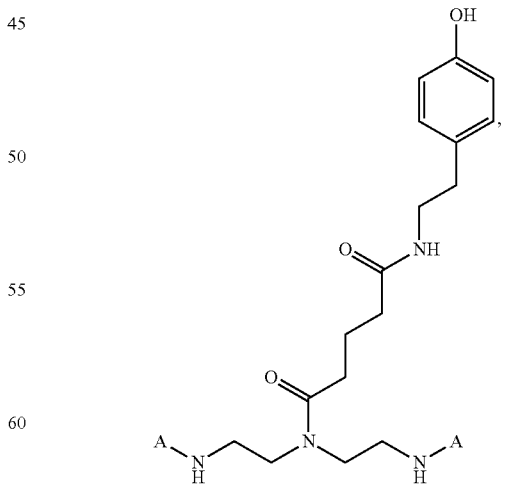

where A is a detectable moiety. In some embodiments, each A group comprises a different detectable moiety.

In some embodiments, the multi-dye conjugate has the structure:
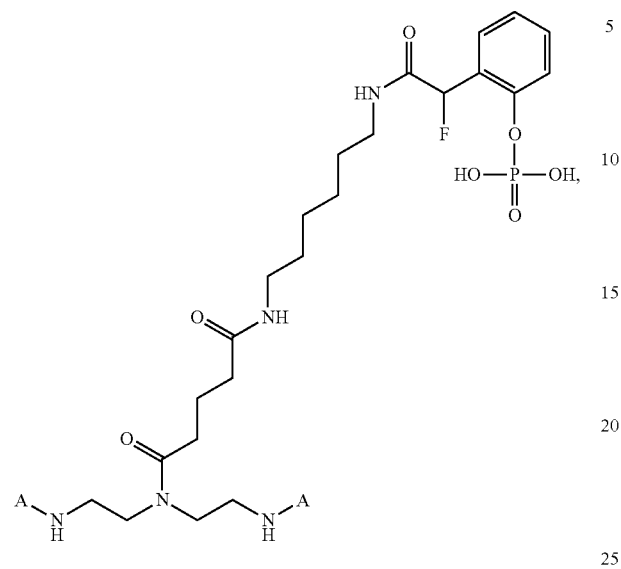
where A is a detectable moiety. In some embodiments, each A group comprises a different detectable moiety.
In some embodiments, the multi-dye conjugate has the structure:
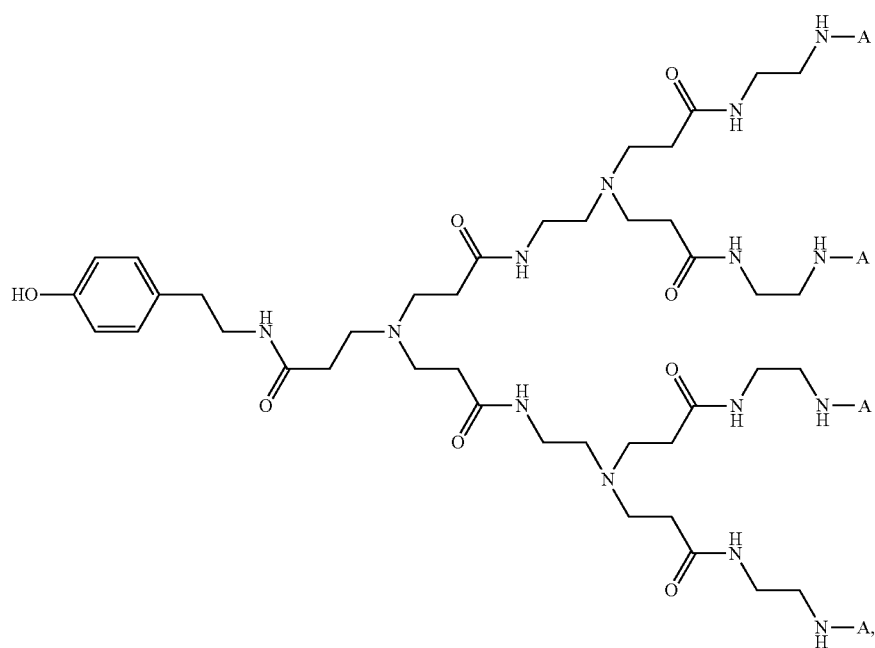
where A is a detectable moiety. In some embodiments, each A group comprises a different detectable moiety.

In some embodiments, the multi-dye conjugate has the structure:
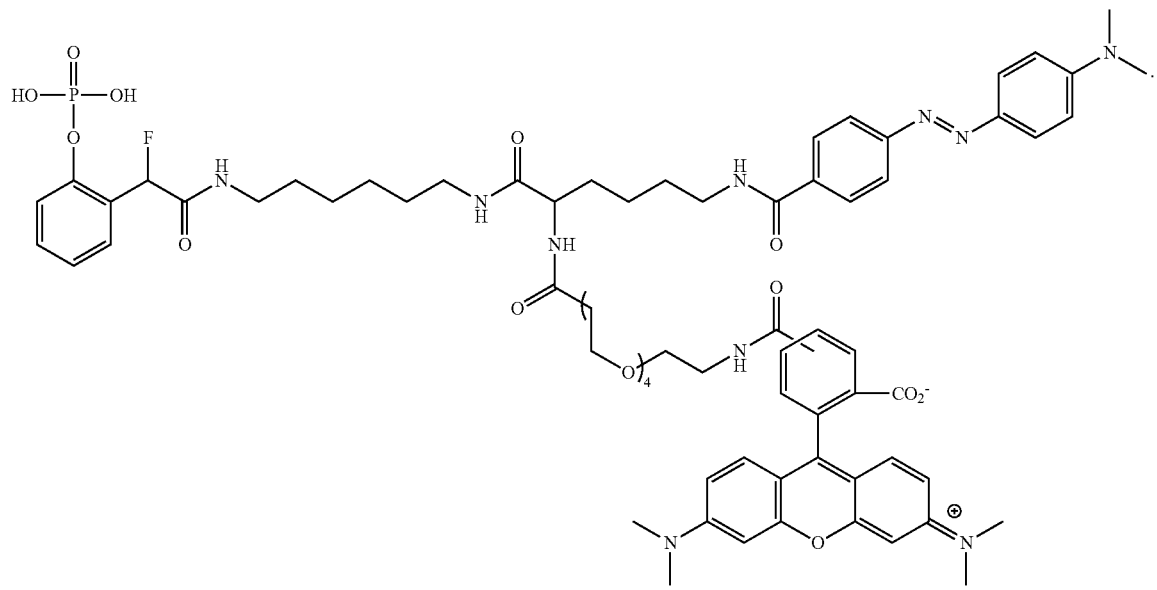
In some embodiments, the multi-dye conjugate has the structure:
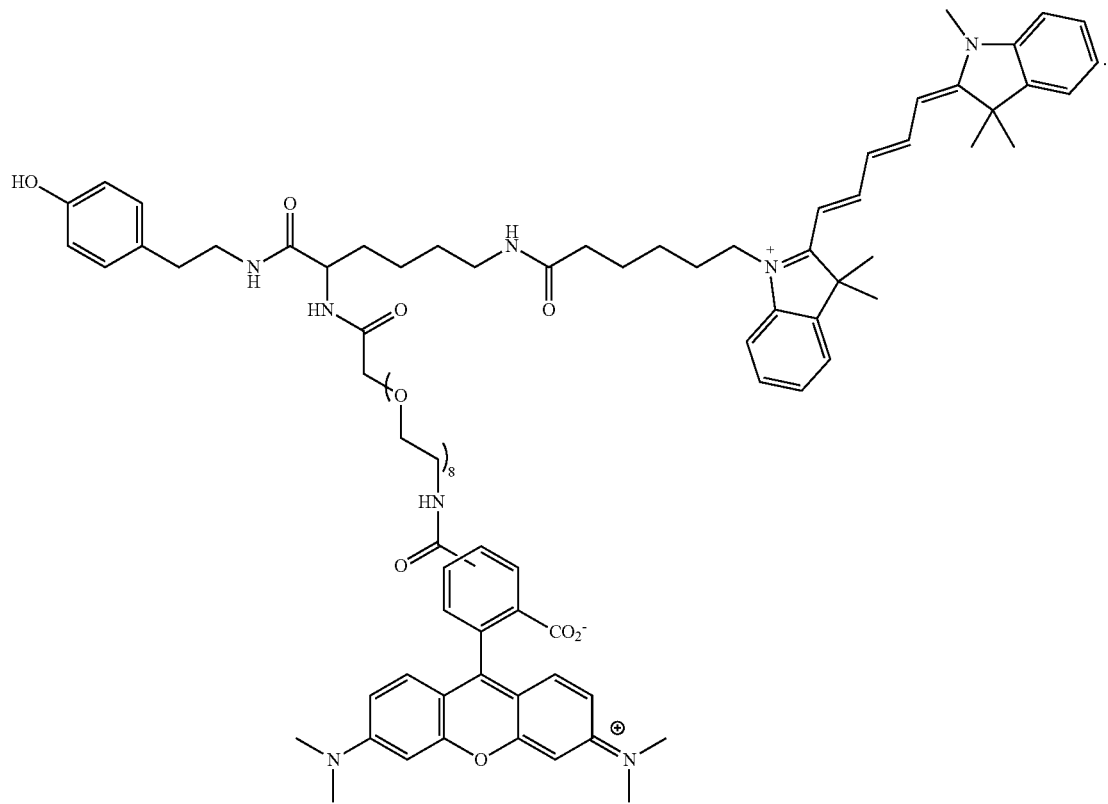

In some embodiments, the multi-dye conjugate has the structure:
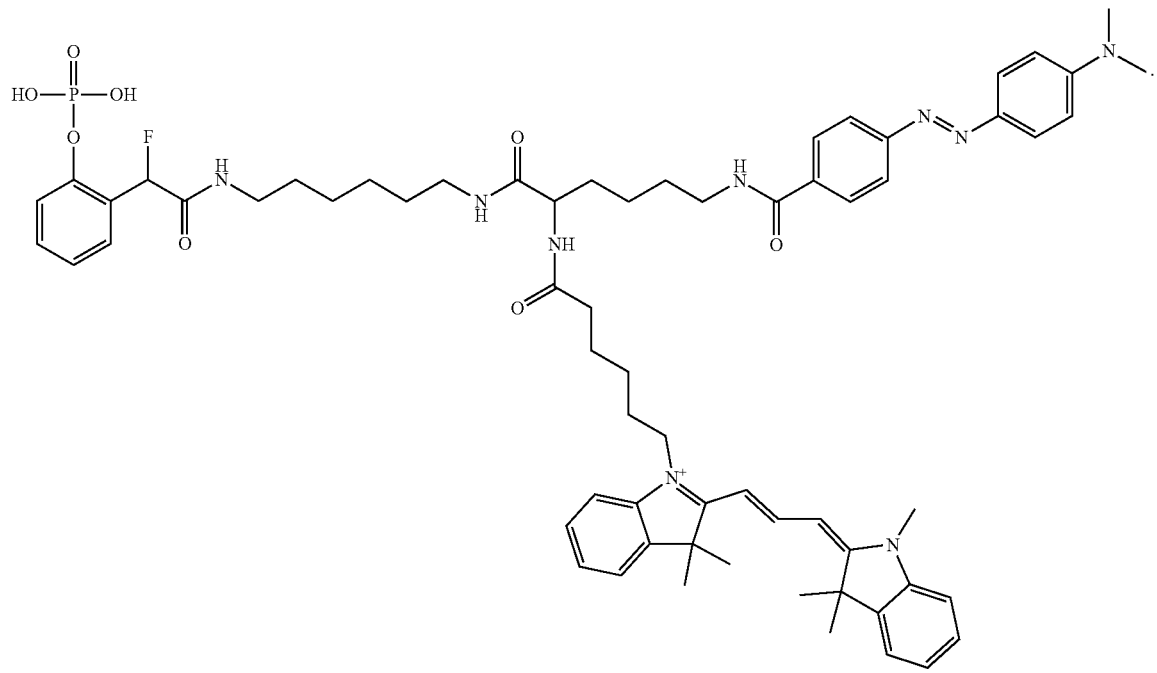 [SMILES: CN(C)c1ccc(/N=N/c2ccc(C(=O)NCCCCC(NC(=O)CCCCC[N+]3=C(/C=C/C=C4/N(C)c5ccccc5C4(C)C)C(C)(C)c4ccccc43)C(=O)NCCCCCCNC(=O)C(F)c3ccccc3OP(=O)(O)O)cc2)cc1]
40
In some embodiments, the multi-dye conjugate has the structure:
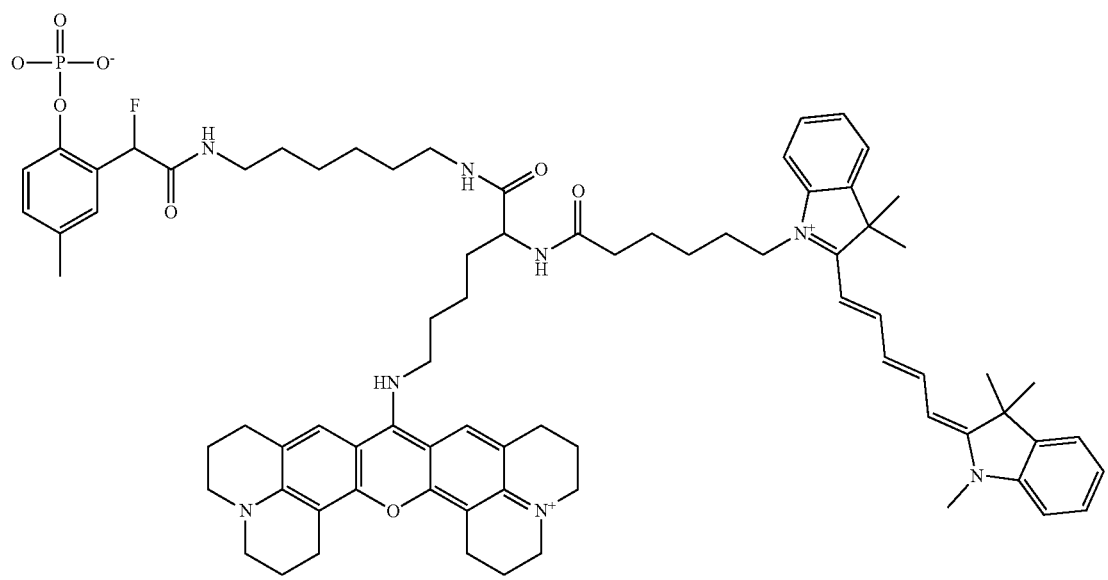 [SMILES: Cc1ccc(OP(=O)([O-])O)c(C(F)C(=O)NCCCCCCNC(=O)C(CCCCNC2=c3cc4c5c(c3Oc3c2cc2c6c3CCCN6CCC2)CCC[N+]=5CCC4)NC(=O)CCCCC[N+]2=C(/C=C/C=C/C=C3/N(C)c4ccccc4C3(C)C)C(C)(C)c3ccccc32)c1]

In some embodiments, the multi-dye conjugate has the structure:

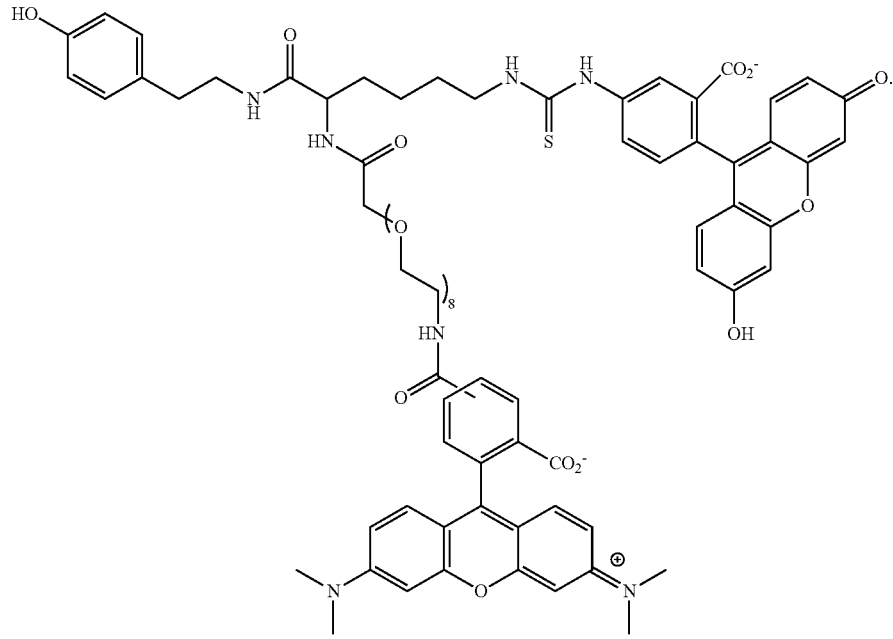

In some embodiments, the multi-dye conjugate has the structure:

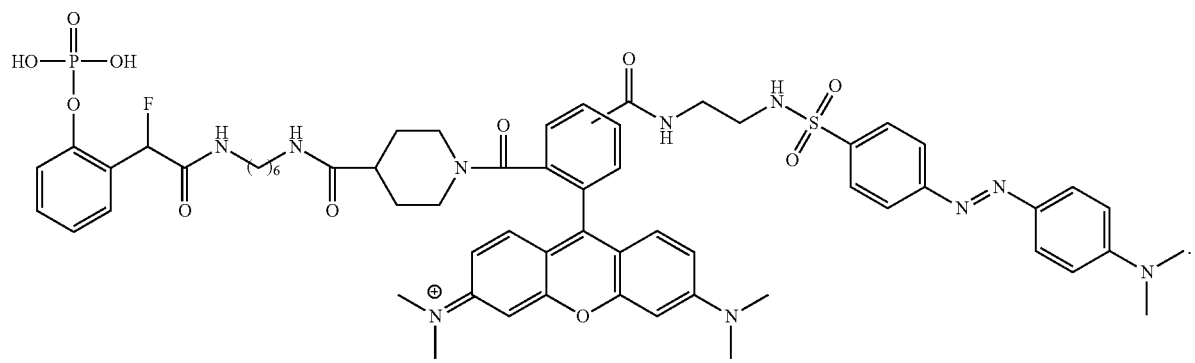

In another aspect of the present disclosure is a method of detecting a first target in a biological sample, comprising contacting the biological sample with a first detection probe specific to the first target to form a first detection probe-target complex; contacting the biological sample with a first labeling conjugate specific for the first detection probe, the first labeling conjugate comprising a first enzyme; and contacting the biological sample with a first multi-dye conjugate, the first multi-dye conjugate comprising a tissue reactive moiety conjugated to at least two chromogens, wherein the first enzyme converts the first multi-dye conjugate to a first reactive intermediate which covalently bonds to the biological sample proximally to or directly on the first target.

In some embodiments, the first detection probe is a first primary antibody and the first labeling conjugate comprises an anti-species antibody conjugated to the first enzyme. In some embodiments, the first detection probe comprises a first nucleic acid probe conjugated to a detectable label, and wherein the first labeling conjugate comprises an anti-label antibody conjugated to the first antibody. In some embodiments, first enzyme is selected from the group consisting of phosphatase, phosphodiesterase, esterase, lipase, amidase, protease, nitroreductase, urease, sulfatase, cytochrome P450, alpha-glucosidase, beta-glucosidase, beta-lactamase, alpha-glucoronidase, beta-glucoronidase, alpha-5 galactosidase, beta-galactosidase, beta-lactamase, neuraminidase, alpha-lactase and beta-lactase. In some embodiments, the first multi-dye conjugate comprises a quinone methide precursor moiety and wherein the first enzyme is alkaline phosphatase. In some embodiments, the first multi-dye conjugate comprises a tyramide or tyramide derivative moiety and wherein the first enzyme is horseradish peroxidase. In some embodiments, the at least two chromophores of the first multi-dye conjugate are selected from the group consisting of TAMRA, Dabsyl, Cy5, Dabcyl, Cy3, rhodamine 800, and fluorescein. In some embodiments, at least two chromophores are conjugated to the tissue reactive moiety through a multi-functional linker. In some embodiments, the multi-functional linker is lysine. In some embodiments, the multi-functional linker is a dendrimer. In some embodiments, a first of the at least two chromophores of the first multi-dye conjugate is conjugated directly or indirectly to the tissue reactive moiety, and a second of the at least two chromophores is conjugated directly or indirectly to the first chromophore.

In some embodiments, the method further comprises contacting the biological sample with a second detection probe specific to a second target to form a second detection probe-target complex; contacting the biological sample with a second labeling conjugate specific for the second detection probe, the second labeling conjugate comprising a second enzyme; and contacting the biological sample with a second multi-dye conjugate, the second multi-dye conjugate comprising a tissue reactive moiety conjugated to at least two chromogens, wherein the second enzyme converts the second multi-dye conjugate to a second reactive intermediate which covalently bonds to the biological sample proximally to or directly on the second target, wherein a color displayed by the first multi-dye conjugate is different from a color displayed by the second multi-dye conjugate.

In some embodiments, the second multi-dye conjugate comprises a tyramide moiety and wherein the first enzyme is a horseradish peroxidase. In some embodiments, the second multi-dye conjugate comprises a quinone methide precursor moiety and wherein the second enzyme is alkaline phosphatase. In some embodiments, the at least two chromophores of the second multi-dye conjugate are selected from the group consisting of TAMRA, Dabsyl, Cy5, Dabcyl, Cy3, rhodamine 800, and fluorescein. In some embodiments, the at least two chromophores of the second multi-dye conjugate are conjugated to the tissue reactive moiety through a multi-functional linker. In some embodiments, the multi-functional linker is lysine. In some embodiments, the multi-functional linker is a dendrimer. In some embodiments, a first of the at least two chromophores of the second multi-dye conjugate is conjugated directly or indirectly to the tissue reactive moiety, and a second of the at least two chromophores is conjugated directly or indirect to the first chromophore.

In some embodiments, the method further comprises contacting the biological sample with a second detection probe specific to a second target to form a second detection probe-target complex; contacting the biological sample with a second labeling conjugate specific for the second detection probe, the second labeling conjugate comprising a second enzyme; and contacting the biological sample with a TSA single chromogen conjugate or QMSA single chromogen conjugate (see, e.g. PCT/EP2015/053556, the disclosure of which is hereby incorporated by reference herein in its entirety), wherein the second enzyme converts the TSA or QMSA single chromogen conjugate to a second reactive intermediate which covalently bonds to the biological sample proximally to or directly on the second target, wherein a color displayed by the first multi-dye conjugate is different from a color displayed by the TSA or QMSA single chromogen conjugate.

In another aspect of the present disclosure is a method of detecting targets within in a biological sample, comprising (i) contacting the biological sample with a first detection probe specific to a first target to form a first detection probe-target complex; (ii) contacting the biological sample with a first labeling conjugate specific for the first detection probe, the first labeling conjugate comprising a first enzyme; (iii) contacting the biological sample with a first conjugate selected from the group consisting of (a) a first multi-dye conjugate, the first multi-dye conjugate comprising a tissue reactive moiety and at least two chromophores, wherein the tissue reactive moiety is selected from the group consisting of a quinone methide precursor or a tyramide or a derivative thereof, (b) a first TSA-single chromogen conjugate, and (c) a first QMSA-single chromogen conjugate; wherein the first enzyme converts the first conjugate conjugate to a first reactive intermediate which covalently bonds to the biological sample proximally to or directly on the first target; (iv) contacting the biological sample with a second detection probe specific to a second target to form a second detection probe-target complex; (v) contacting the biological sample with a second labeling conjugate specific for the second detection probe, the second labeling conjugate comprising a second enzyme; and (vi) contacting the biological sample with a second conjugate selected from the group consisting of (a) a second multi-dye conjugate, the second multi-dye conjugate comprising a tissue reactive moiety and at least two chromophores, wherein the tissue reactive moiety is selected from the group consisting of a quinone methide precursor or a tyramide or a derivative thereof, (b) a second TSA-single chromogen conjugate, and (c) a second QMSA-single chromogen conjugate; wherein the second enzyme converts the second conjugate to a second reactive intermediate which covalently bonds to the biological sample proximally to or directly on the second target; and wherein the first and second conjugates display different colors.

In another aspect of the present disclosure is a method of detecting a first target in a biological sample, comprising contacting the biological sample with a first detection probe specific to the first target to form a first detection probe-target complex; contacting the biological sample with a first labeling conjugate specific for the first detection probe, the first labeling conjugate comprising a first enzyme; and contacting the biological sample with a first multi-dye conjugate of Formula (I),

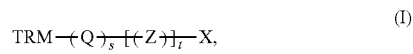

$$\text{TRM}-(Q)_s-[(Z)]_t-X, \quad (I)$$

wherein "TRM" is a tissue reactive moiety; Q is a branched or unbranched, linear or cyclic, substituted or unsubstituted group having between 2 and 40 carbon atoms, and optionally having one or more heteroatoms selected from O, N, or S; Z is a bond or a branched or unbranched, linear or cyclic, substituted or unsubstituted, saturated or unsaturated, group having between 2 and 20 carbon atoms, and optionally having one or more heteroatoms selected from O, N, or S; X is H, -[(Q)$_d$-[A]$_n$]$_e$; —N—([Z]—[X])$_2$; or —C(H)([Z]—[X])$_2$; A is a detectable moiety; d is 0 or 1; e is an integer ranging from 1 to 4; s is 0 or an integer ranging from 1 to 4; and t is 0 or an integer ranging from 1 to 10; provided that the multi-dye conjugate comprises at least two A groups (e.g. at least two chromogens); and wherein the first enzyme converts the first multi-dye conjugate to a first reactive intermediate which covalently bonds to the biological sample proximally to or directly on the first target.

In some embodiments, the method further comprises (i) contacting the biological sample with a second detection probe specific to a second target to form a second detection probe-target complex; (ii) contacting the biological sample with a second labeling conjugate specific for the second detection probe, the second labeling conjugate comprising a second enzyme; and (iii) contacting the biological sample with a second multi-dye conjugate of Formula (I), wherein a color displayed by the first multi-dye conjugate is different from a color displayed by the second multi-dye conjugate.

In some embodiments, Q has the structure of Formula (IVa):

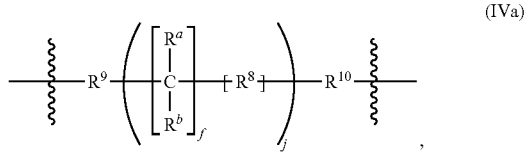

(IVa)

wherein f is 0, 1, or 2; $R^8$ is a bond, O, S, or $N(R^c)(R^d)$; $R^a$ and $R^b$ are independently H, a $C_1$-$C_4$ alkyl group, F, Cl, or —$N(R^c)(R^d)$; $R^c$ and $R^d$ are independently selected from $CH_3$ or H; $R^9$ and $R^{10}$ are independently a bond or a group selected from carbonyl, amide, imide, ester, ether, amine, thione, thiol; and j is an integer ranging from 1 to 8.

In some embodiments, (Q) has the structure of Formula (IVb):

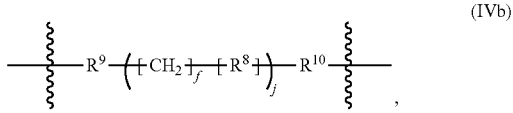

(IVb)

wherein f is 0, 1, or 2; $R^8$ is a bond, O, S, or $N(R^c)(R^d)$; $R^c$ and $R^d$ are independently $CH_3$ or H; $R^9$ and $R^{10}$ are independently a bond or a group selected from carbonyl, amide, imide, ester, ether, amine, or thiol; and j is an integer ranging from 1 to 8.

In some embodiments, Z has the structure of Formula (Va):

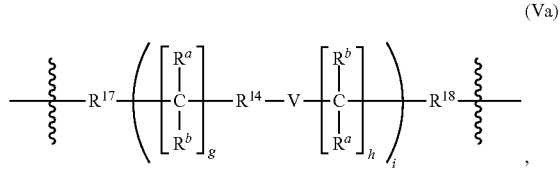

(Va)

wherein $R^{17}$ and $R^{18}$ are independently a bond or a group selected from carbonyl, amide, imide, ester, ether, —NH, —N—, thione, or thiol; $R^{14}$ is a bond, a carbonyl, an imine, or a thione;

V is a bond, —$C(R^{15})(R^{16})$—, —O—, —S—, —$N(R^{16})$—, —N(X)—; —$C(R^{15})(X)$; —$C(X)_2$—, or —$C(R^{15})(N(R^{16})(X))$; X is as defined herein; $R^a$ and $R^b$ are independently H, a $C_1$-$C_4$ alkyl group, F, Cl, or $N(R^{15})(R^{16})$; $R^{15}$ and $R^{16}$ are independently a bond or —$CH_3$ or H; g is 0 or an integer ranging from 1 to 4; h is 0 or an integer ranging from 1 to 8; and i is 1 or 2.

In another aspect of the present disclosure is a kit comprising:

(i) a multi-dye conjugate having Formula (I):

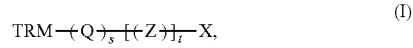

(I)

wherein

"TRM" is a tissue reactive moiety; Q is a branched or unbranched, linear or cyclic, substituted or unsubstituted group having between 2 and 40 carbon atoms, and optionally having one or more heteroatoms selected from O, N, or S; Z is a bond or a branched or unbranched, linear or cyclic, substituted or unsubstituted, saturated or unsaturated, group having between 2 and 20 carbon atoms, and optionally having one or more heteroatoms selected from O, N, or S; X is H, -[(Q)$_d$-[A]$_n$]$_e$; —N—([Z]—[X])$_2$; or —C(H)([Z]—[X])$_2$; A is a detectable moiety; d is 0 or 1; e is an integer ranging from 1 to 4; s is 0 or an integer ranging from 1 to 4; and t is 0 or an integer ranging from 1 to 10; wherein the multi-dye conjugate comprises at least two A groups;

(ii) a detection probe specific to a target; and
(iii) a labeling conjugate specific for the first detection probe.

In some embodiments, the detection probe is a primary antibody. In some embodiments, the detection probe is a nucleic acid probe conjugated to a label. In some embodiments, the labeling conjugate is an anti-antibody antibody, and wherein the anti-antibody antibody is conjugated to an enzyme. In some embodiments, the labeling conjugate is an anti-label antibody, and wherein the anti-label antibody is conjugated to an enzyme.

One limitation of TSA and QMSA is the requirement that the dyes that are conjugated comprise a chemically reactive functional group that the tyramide or quinone methide can couple to (to form the respective TSA or QMSA single-chromogen conjugates). While there exist many compounds that have such chemically reactive groups that allow for the production of TSA or QMSA single-chromogen conjugates having certain colors, there exist other desirable color spaces that are unavailable (e.g. green, red, and violet) due to the lack of dyes having the requisite reactive functional groups.

Applicants have discovered novel chromogenic systems that are able to expand the palette of available colors for chromogenic IHC and ISH staining with both TSA and QMSA technologies. Indeed, the novel chromogenic systems are discrete chemical compounds that exhibit colors currently unattainable with the use of single dye conjugates (e.g. TSA or QMSA single-chromogen conjugates).

Moreover, the use of the novel chromogenic systems is superior to the current approach of generating new colors through conjugate mixing. First, Applicants have found that different dye-tyramide (TSA single-chromogen conjugates) and dye-quinone methide conjugates (QMSA single-chromogen conjugates) react with their cognate enzyme and/or with tissue at varying rates, which can cause color gradients upon staining. For example, in the case of yellow conjugates reacting faster than magenta conjugates, a mixture of magenta and yellow conjugates (to make red) may result in higher expressing tissue regions having a more orange hue, with lower expressing regions appearing more purple. Applicants have found that using a multi-dye conjugate such as described herein, does not have this issue since it is a discrete molecule.

In addition, Applicants have discovered that the new multi-dye conjugates of the present disclosure provide higher overall signal compared to using mixtures of single-dye conjugates (e.g. TSA or QMSA single-chromogen conjugates). Without wishing to be bound by any particular theory, it is believed that this is the case since a limited number of covalent binding sites exist on tissue, and mixing two or more chromogen conjugates effectively reduces the overall staining concentration compared to utilizing discrete compounds. For example, if overall signal saturates at 2 mM, to generate a novel color by mixing chromogen conjugates at a 1:1 ratio, 1 mM of each dye would be used. However, by using 1 mM of the multi-dye conjugate containing both dyes on a single molecule, twice as much dye can be deposited, resulting in significantly higher overall signal.

Finally, Applicants have further discovered that, from a manufacturing standpoint, the requirement to mix multiple conjugates in a specific ratio creates the potential for different lots of material to vary in color. The use of a multi-dye conjugate containing both dyes on a single molecule would eliminate this potential issue. These and other advantages are further described herein.

DETAILED DESCRIPTION

Figure 1:
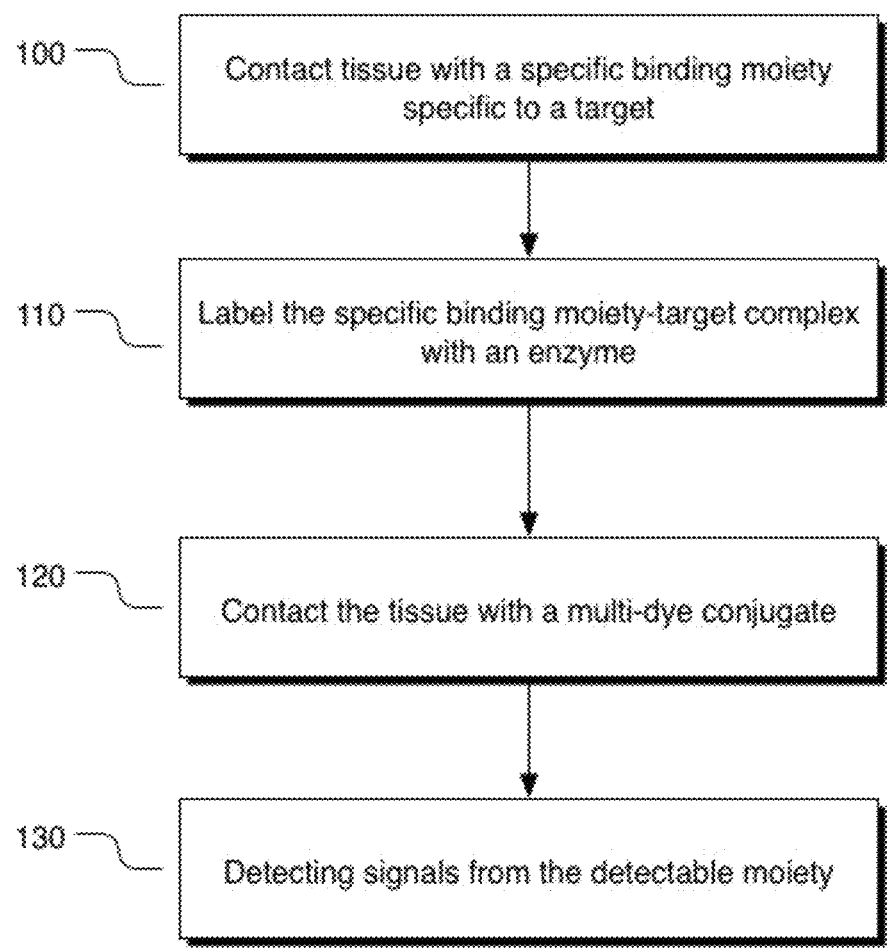
FIG. 1 provides a flowchart illustrating the steps of detecting one or more targets utilizing one or more specific binding moieties and/or multi-dye conjugates.

Disclosed herein are novel conjugates, the conjugates comprising at least two detectable moieties. (referred to herein as "multi-dye conjugates"). The multi-dye conjugates are suitable for use in QMSA and TSA protocols. Also disclosed are methods of using the multi-dye conjugates to enable detection of one or more targets in a biological sample.

Definitions

As used herein, the singular terms "a," "an," and "the" include plural referents unless context clearly indicates otherwise. Similarly, the word "or" is intended to include "and" unless the context clearly indicates otherwise. The term "includes" is defined inclusively, such that "includes A or B" means including A, B, or A and B.

The terms "comprising," "including," "having," and the like are used interchangeably and have the same meaning. Similarly, "comprises," "includes," "has," and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b and c. Similarly, the phrase: "a method involving steps a, b, and c" means that the method includes at least steps a, b, and c. Moreover, while the steps and processes may be outlined herein in a particular order, the skilled artisan will recognize that the ordering steps and processes may vary.

As used herein, alkaline phosphatase (AP) is an enzyme that removes (by hydrolysis) and transfers phosphate group organic esters by breaking the phosphate-oxygen bond, and temporarily forming an intermediate enzyme-substrate bond. For example, AP hydrolyzes naphthol phosphate esters (a substrate) to phenolic compounds and phosphates. The phenols couple to colorless diazonium salts (chromogen) to produce insoluble, colored azo dyes.

As used herein, the term "antibody," occasionally abbreviated "Ab," refers to immunoglobulins or immunoglobulin-like molecules, including by way of example and without limitation, IgA, IgD, IgE, IgG and IgM, combinations thereof, and similar molecules produced during an immune response in any vertebrate, (e.g., in mammals such as humans, goats, rabbits and mice) and antibody fragments that specifically bind to a molecule of interest (or a group of highly similar molecules of interest) to the substantial exclusion of binding to other molecules. Antibody further refers to a polypeptide ligand comprising at least a light chain or heavy chain immunoglobulin variable region which specifically recognizes and binds an epitope of an antigen. Antibodies may be composed of a heavy and a light chain, each of which has a variable region, termed the variable heavy (VH) region and the variable light (VL) region. Together, the VH region and the VL region are responsible for binding the antigen recognized by the antibody. The term antibody also includes intact immunoglobulins and the variants and portions of them well known in the art.

As used herein, the phrase "antibody conjugates," refers to those antibodies conjugated (either directly or indirectly) to one or more labels, where the antibody conjugate is specific to a particular target and where the label is capable of being detected (directly or indirectly), such as with a secondary antibody (an anti-label antibody). For example, an antibody conjugate may be coupled to a hapten such as through a polymeric linker and/or spacer, and the antibody conjugate, by means of the hapten, may be indirectly detected. As an alternative example, an antibody conjugate may be coupled to a fluorophore, such as through a polymeric linker and/or spacer, and the antibody conjugate may be detected directly. Antibody conjugates are described further in US Publication No. 2014/0147906 and U.S. Pat. Nos. 8,658,389; 8,686,122; 8,618,265; 8,846,320; and 8,445,191. By way of a further example, the term "antibody conjugates" includes those antibodies conjugated to an enzyme, e.g. HRP or AP.

As used herein, the term "antigen" refers to a compound, composition, or substance that may be specifically bound by the products of specific humoral or cellular immunity, such as an antibody molecule or T-cell receptor. Antigens can be any type of molecule including, for example, haptens, simple intermediary metabolites, sugars (e.g., oligosaccharides), lipids, and hormones as well as macromolecules such as complex carbohydrates (e.g., polysaccharides), phospholipids, nucleic acids and proteins.

As used herein, the term a "biological sample" can be any solid or fluid sample obtained from, excreted by or secreted by any living organism, including without limitation, single celled organisms, such as bacteria, yeast, protozoans, and amoebas among others, multicellular organisms (such as plants or animals, including samples from a healthy or apparently healthy human subject or a human patient affected by a condition or disease to be diagnosed or investigated, such as cancer). For example, a biological sample can be a biological fluid obtained from, for example, blood, plasma, serum, urine, bile, ascites, saliva, cerebrospinal fluid, aqueous or vitreous humor, or any bodily secretion, a transudate, an exudate (for example, fluid obtained from an abscess or any other site of infection or inflammation), or fluid obtained from a joint (for example, a normal joint or a joint affected by disease). A biological sample can also be a sample obtained from any organ or tissue (including a biopsy or autopsy specimen, such as a tumor biopsy) or can include a cell (whether a primary cell or cultured cell) or medium conditioned by any cell, tissue or organ. In some examples, a biological sample is a nuclear extract. In certain examples, a sample is a quality control sample, such as one of the disclosed cell pellet section samples. In other examples, a sample is a test sample. Samples can be prepared using any method known in the art by of one of ordinary skill. The samples can be obtained from a subject for routine screening or from a subject that is suspected of having a disorder, such as a genetic abnormality, infection, or a neoplasia. The described embodiments of the disclosed method can also be applied to samples that do not have genetic abnormalities, diseases, disorders, etc., referred to as "normal" samples. Samples can include multiple targets that can be specifically bound by one or more detection probes.

As used herein, the term "chromophore" refers to a molecule or a part of a molecule responsible for its color. Color arises when a molecule absorbs certain wavelengths of visible light and transmits or reflects others. A molecule having an energy difference between two different molecular orbitals falling within the range of the visible spectrum may absorb visible light and thus be aptly characterized as a chromophore. Visible light incident on a chromophore may be absorbed thus exciting an electron from a ground state molecular orbital into an excited state molecular orbital.

As used herein, the term "conjugate" refers to two or more molecules or moieties (including macromolecules or supramolecular molecules) that are covalently linked into a larger construct. In some embodiments, a conjugate includes one or more biomolecules (such as peptides, proteins, enzymes, sugars, polysaccharides, lipids, glycoproteins, and lipoproteins) covalently linked to one or more other molecules moieties.

As used herein, the terms "couple" or "coupling" refers to the joining, bonding (e.g. covalent bonding), or linking of one molecule or atom to another molecule or atom.

As used herein, the term "detectable moiety" refers to a molecule or material that can produce a detectable (such as visually, electronically or otherwise) signal that indicates the presence (i.e. qualitative analysis) and/or concentration (i.e. quantitative analysis) of the label in a sample. A detectable signal can be generated by any known or yet to be discovered mechanism including absorption, emission and/or scattering of a photon (including radio frequency, microwave frequency, infrared frequency, visible frequency and ultraviolet frequency photons). Examples of detectable moieties include chromogenic, fluorescent, phosphorescent and luminescent molecules and materials.

As used herein, "haptens" are small molecules that can combine specifically with an antibody, but typically are substantially incapable of being immunogenic except in combination with a carrier molecule. In some embodiments, haptens include, but are not limited to, pyrazoles (e.g. nitropyrazoles); nitrophenyl compounds; benzofurazans; triterpenes; ureas (e.g. phenyl ureas); thioureas (e.g. phenyl thioureas); rotenone and rotenone derivatives; oxazole (e.g. oxazole sulfonamides); thiazoles (e.g. thiazole sulfonamides); coumarin and coumarin derivatives; and cyclolignans. Additional non-limiting examples of haptens include thiazoles; nitroaryls; benzofurans; triperpenes; and cyclolignans. Specific examples of haptens include di-nitrophenyl, biotin, digoxigenin, and fluorescein, and any derivatives or analogs thereof. Other haptens are described in U.S. Pat. Nos. 8,846,320; 8,618,265; 7,695,929; 8,481,270; and 9,017,954, the disclosures of which are incorporated herein by reference in their entirety. The haptens themselves may be suitable for direct detection, i.e. they may give off a suitable signal for detection.

As used herein, horseradish peroxidase (HRP) is an enzyme that can be conjugated to a labeled molecule. It produces a colored, fluorimetric, or luminescent derivative of the labeled molecule when incubated with a proper substrate, allowing it to be detected and quantified. HRP acts in the presence of an electron donor to first form an enzyme substrate complex and then subsequently acts to oxidize an electronic donor. For example, HRP may act on 3,3'-diaminobenzidinetrahydrochloride (DAB) to produce a detectable color. HRP may also act upon a labeled tyramide conjugate, or tyramide like reactive conjugates (i.e. ferulate, coumaric, caffeic, cinnamate, dopamine, etc.), to deposit a colored or fluorescent or colorless reporter moiety for tyramide signal amplification (TSA).

As used herein, the terms "multiplex," "multiplexed," or "multiplexing" refer to detecting multiple targets in a sample concurrently, substantially simultaneously, or sequentially. Multiplexing can include identifying and/or quantifying multiple distinct nucleic acids (e.g., DNA, RNA, mRNA, miRNA) and polypeptides (e.g., proteins) both individually and in any and all combinations.

As used herein, the term "primary antibody" refers to an antibody which binds specifically to the target protein antigen in a tissue sample. A primary antibody is generally the first antibody used in an immunohistochemical procedure.

As used herein, a "quinone methide" is a quinone analog where one of the carbonyl oxygens on the corresponding quinone is replaced by a methylene group ($CH_2$) to form an alkene.

As used herein, the term "secondary antibody" herein refers to an antibody which binds specifically to a primary antibody, thereby forming a bridge between the primary antibody and a subsequent reagent (e.g. a label, an enzyme, etc.), if any. The secondary antibody is generally the second antibody used in an immunohistochemical procedure.

As used herein, the term "specific binding entity" refers to a member of a specific-binding pair. Specific binding pairs are pairs of molecules that are characterized in that they bind each other to the substantial exclusion of binding to other molecules (for example, specific binding pairs can have a binding constant that is at least $10^{-3}$ M greater, $10^{-4}$ M greater or $10^{-5}$ M greater than a binding constant for either of the two members of the binding pair with other molecules in a biological sample). Particular examples of specific binding moieties include specific binding proteins (for example, antibodies, lectins, avidins such as streptavidins, and protein A). Specific binding moieties can also include the molecules (or portions thereof) that are specifically bound by such specific binding proteins.

As used herein, the term "target" refers to any molecule for which the presence, location and/or concentration is or can be determined. Examples of target molecules include proteins, nucleic acid sequences, and haptens, such as haptens covalently bonded to proteins. Target molecules are typically detected using one or more conjugates of a specific binding molecule and a detectable label.

Conjugates

The present disclosure provides novel conjugates comprising a plurality of detectable moieties (e.g. chromogens). The plurality of detectable moieties of the multi-dye conjugates may be the same or different. In some embodiments, at least two of the detectable moieties of the multi-dye conjugates are different. For example, the multi-dye conjugate may comprise a TAMRA chromogen and a Cy5 chromogen. In other embodiments, at least two of the detectable moieties of the multi-dye conjugates are selected such that the individual detectable moieties individually display different signals. For example, the multi-dye conjugate may comprise a TAMRA chromogen and a Dabsyl chromogen, where each of TAMRA and Dabsyl display different colors. In other embodiments, the multi-dye conjugates comprise a plurality of detectable moieties, where at least two of the detectable moieties are the same and where at least a third detectable moiety is different.

In some embodiments, the multi-dye conjugates are designed such that they provide a means for generating new colors for chromogenic IHC and ISH staining with both tyramide and quinone methide signal amplification technologies. Again, as noted herein, certain color spaces are not available since chromogens suitable for producing those colors are not able to be coupled to a tyramide or a quinone methide precursor (e.g. resorufin, nile blue, and malachite green). By coupling a plurality of different colored chromogens, the multi-dye conjugates are able to directly provide, for example, red, violet, and green colors, without resorting to mixing of different combinations of TSA or QMSA single-chromogen conjugates. Superior results are thus able to be achieved as comparing with simply mixing dyes (as described herein).

The ability to create new, distinct colors is based on the principle of subtractive color mixing (Berns, R. S., Billmeyer, F. W., Saltzman, M., and Billmeyer, F. W. (2000) Billmeyer and Saltzman's Principles of Color Technology, Wiley, New York.) Briefly, this concept creates new colors as a result of partially or completely absorbing some wavelengths of light. Without wishing to be bound by any particular theory, is believed that the color of the multi-dye conjugates depends on the wavelengths of light that are still able to pass through after subtraction of each dye. The dyes utilized here are believed to be "narrowly absorbing," meaning they absorb only a relatively narrow part of the visible spectrum while allowing the majority of light to pass through. The use of "narrowly absorbing" dyes is believed to allow for the dyes to mix and form new, distinct colors, because some amount of light can still pass through. If broadly absorbing dyes were used it is believed that they would end up subtracting too much of the spectrum, leaving dark reds, browns, and blacks that are not easily distinguished from one another. FIGS. 13A-13D provide spectra for certain dual-dye conjugates, and specifically illustrate dual dye color, as compared with individual single dye colors.

Figure 10:
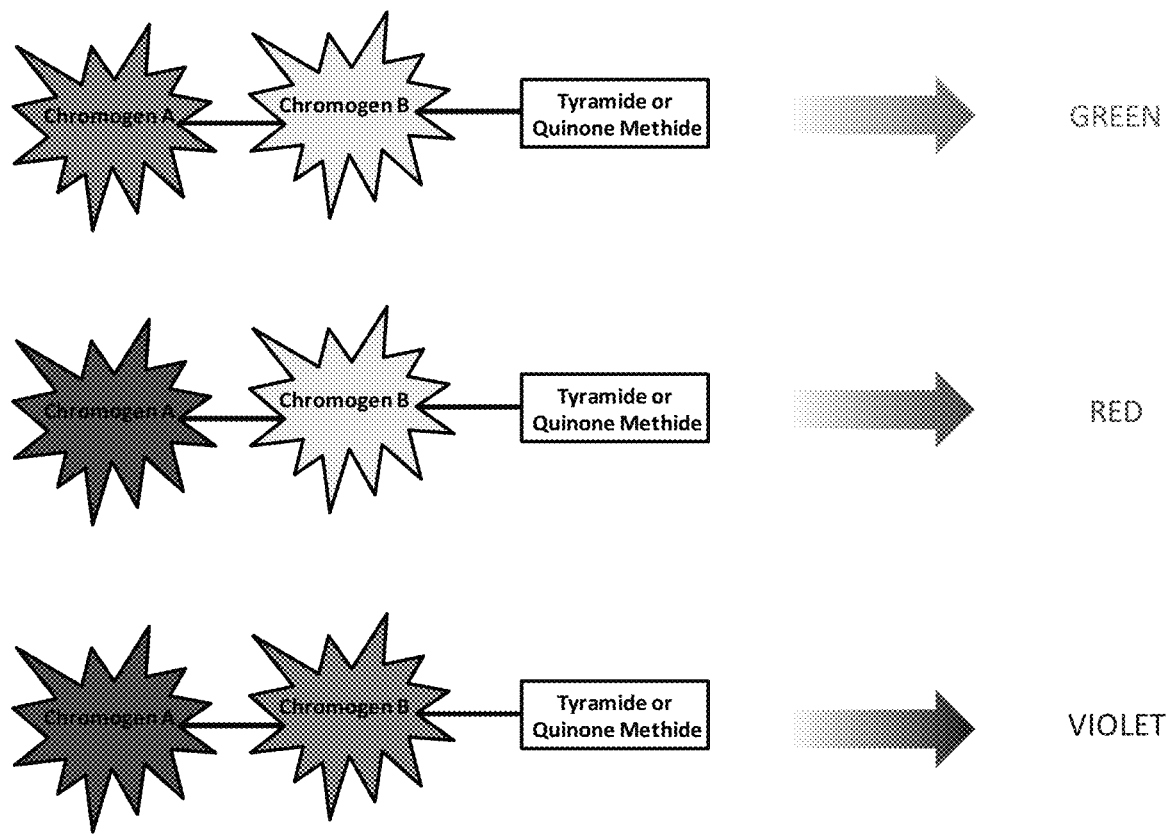
FIG. 10 illustrates the combination of two different chromogens and the resulting color after the two different chromogens are coupled.

In some embodiments, the multi-dye conjugates are arranged in a "linear" configuration. By arranged in a "linear" configuration, it is meant that a detectable moiety of the multi-dye conjugate comprises multiple conjugation sites that enable it to (i) directly or indirectly couple to another detectable moiety (which itself may allow coupling to another detectable moiety), and (ii) directly or indirectly couple to a tissue reactive moiety (as that term is defined herein). Multi-dye conjugates comprising such as linear arrangement are depicted in FIG. 10. For example, linking a yellow chromogen to a cyan chromogen and a tissue reactive moiety provides for a multi-dye conjugate which provides a green color. Likewise, linking a yellow chromogen with a purple chromogen and a tissue reactive moiety process for a multi-dye conjugate which provides a red color. Similarly, linking a cyan chromogen to a violet chromogen and a tissue reactive moiety provides for an indigo color. While each of these examples illustrate the coupling in series of multiple chromogens to a tissue reactive moiety, the skilled artisan will appreciate that any multi-dye conjugate may comprise more than two chromogens, to provide yet further colors, hues, or intensities. While FIG. 10 depicts examples comprising two detectable moieties, the skilled artisan will appreciate that any number of detectable moieties may be directly or indirectly coupled to each other.

In some embodiments, the multi-dye conjugates are arranged in a "branched" configuration. By arranged in a "branched" configuration, it is meant that a linker or multi-functional linker comprising a plurality of conjugation sites is used to couple directly or indirectly (i) a plurality of detectable moieties to (ii) a tissue reactive moiety, as depicted in the schematic below and as further illustrated in FIG. 11. In some embodiments, the multi-functional linker comprises at least three sites for conjugation. In other embodiments, the multi-functional linker comprises four or more sites for conjugation. While the schematic which follows indicates that the multi-functional linker is conjugated to two chromogens, any number of detectable moieties may be conjugated to the tissue reactive moiety provided that the multi-functional linker comprises sufficient sites for conjugation.

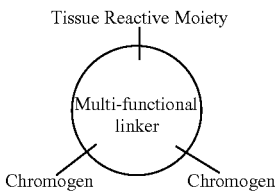

In some embodiments, the multi-functional linker provides at least three functional groups capable of coupling directly or indirectly to (i) at least two chromogens and (ii) a tissue reactive moiety. In some embodiments, the multi-functional linker comprises a plurality of amine, carboxyl, maleimide, or thiol groups to effect conjugation. In some embodiments, the multi-functional linker is selected from one which may be orthogonally protected and deprotected, allowing the skilled artisan to conjugate one chromogen at a time to the multi-functional linker, thus preventing unwanted side reactions or side products.

In some embodiments, the multi-functional linker has a molecular weight ranging from about 1 g/mol to about 300 g/mol. In other embodiments, the multi-functional linker has a molecular weight ranging from about 20 g/mol to about 250 g/mol. In some embodiments, the multi-functional linker comprises solubilizing groups, such as polyethylene glycol (PEG) groups, to increase the water solubility of the multi-dye conjugate. In some embodiments, the multi-functional linker comprises between about 2 and about 8 PEG groups. In other embodiments, the multi-functional linker comprises between about 2 and about 6 PEG groups.

In some embodiments, the multi-functional linker is a polyamine. In some embodiments, the polyamine comprises between 2 and 20 amine groups. In other embodiments, the polyamine comprises between 2 and 10 amine groups. In yet other embodiments, the polyamine comprises between 2 and 6 amine groups. Examples of polyamines include norspermidine, spermine, and derivatives or analogs thereof.

In some embodiments, the multi-functional linker is a hetero-bifunctional linker, i.e. one comprising at least two different reactive functional groups. For example, a hetero-bifunctional linker may comprise a carboxylic acid group and two amine groups. In some embodiments, the multi-functional linker is lysine or a derivative of lysine.

In other embodiments, the multi-functional linker is a polymer having a repeat group comprising at least one conjugation site for coupling to a chromogen. In other embodiments, the multi-functional linker is a dendrimer, the dendrimer comprising a plurality of branched groups, each branched group comprising at least one conjugation site. In some embodiments, suitable dendrimers include, polyamidoamine (PAMAM) dendrimers, Janus dendrimers (i.e. dendrimers constituted of two dendrimeric wedges and terminated by two different functionalities), and bis-MPA dendrimers and derivatives thereof.

Figure 11:
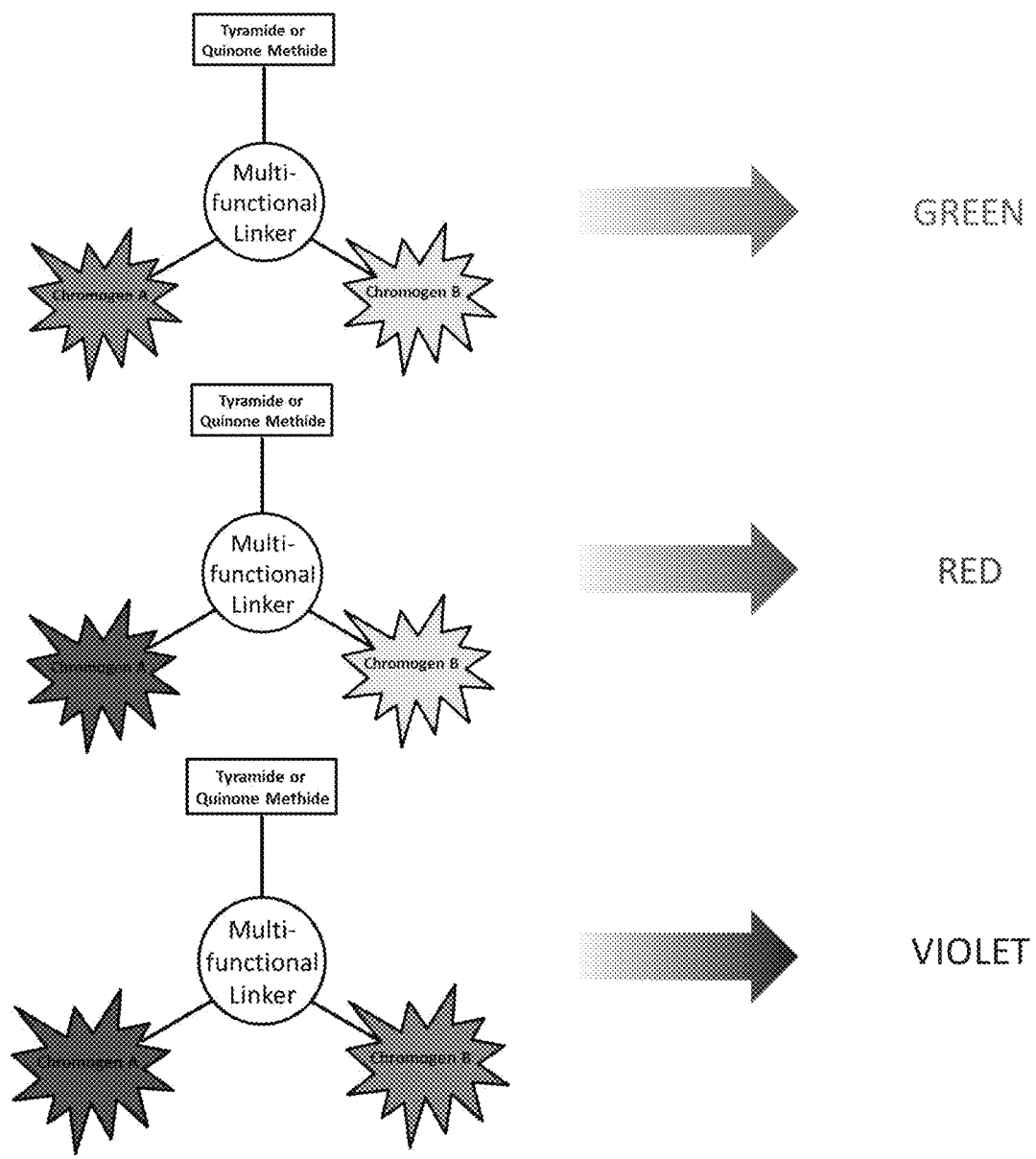
FIG. 11 illustrates the combination of two different chromogens and the resulting color after the two different chromogens are coupled.
Figure 12:
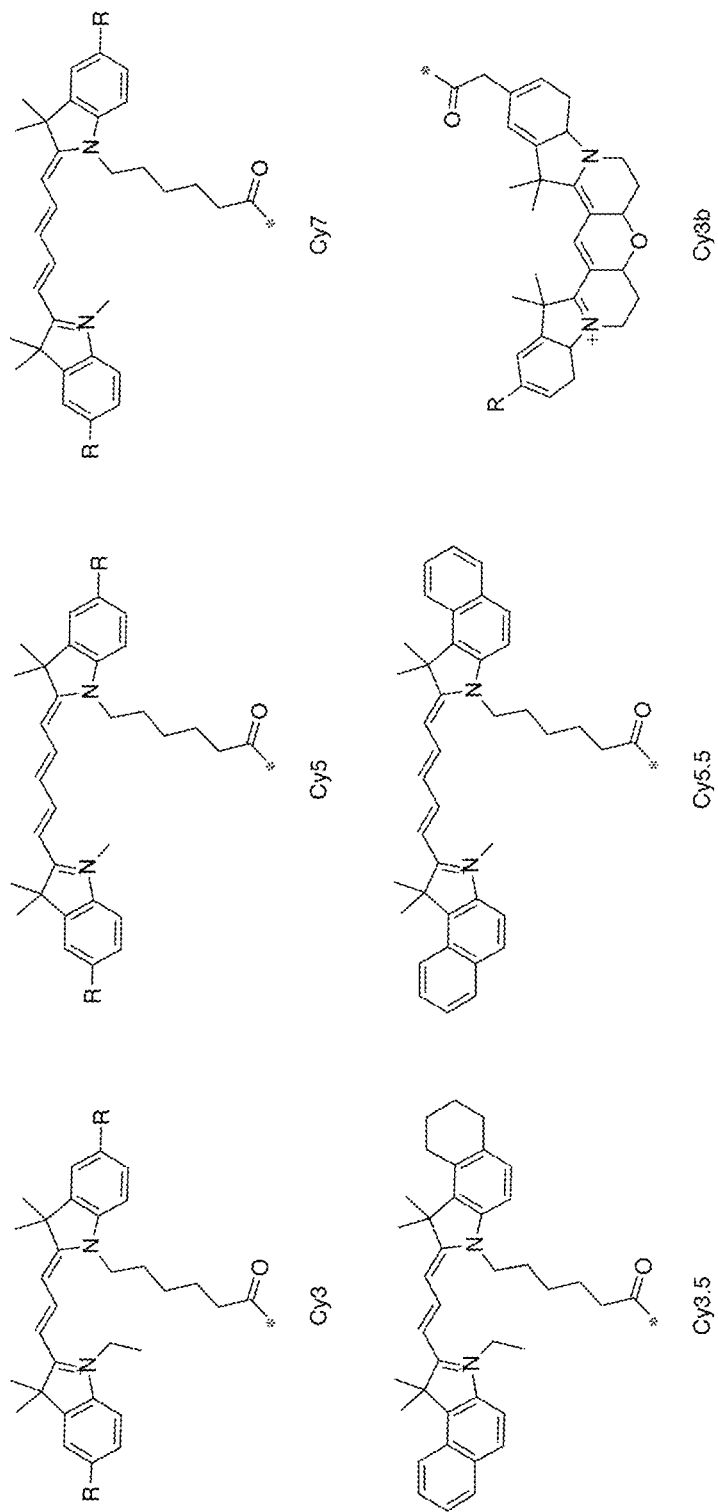
FIG. 12 sets forth variants of different "Cy" chromogens.
Figure 13A:
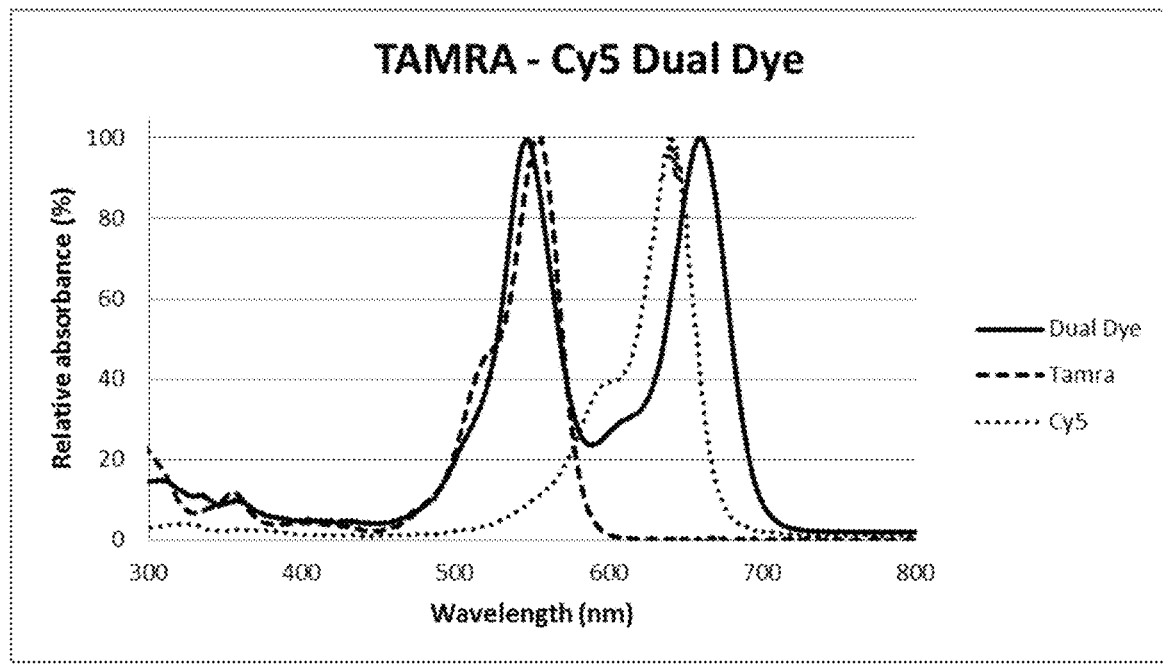
FIG. 13A provides spectra for a TAMRA-Cy5 duel dye conjugate as compared to single dye color spectra.
Figure 13B:
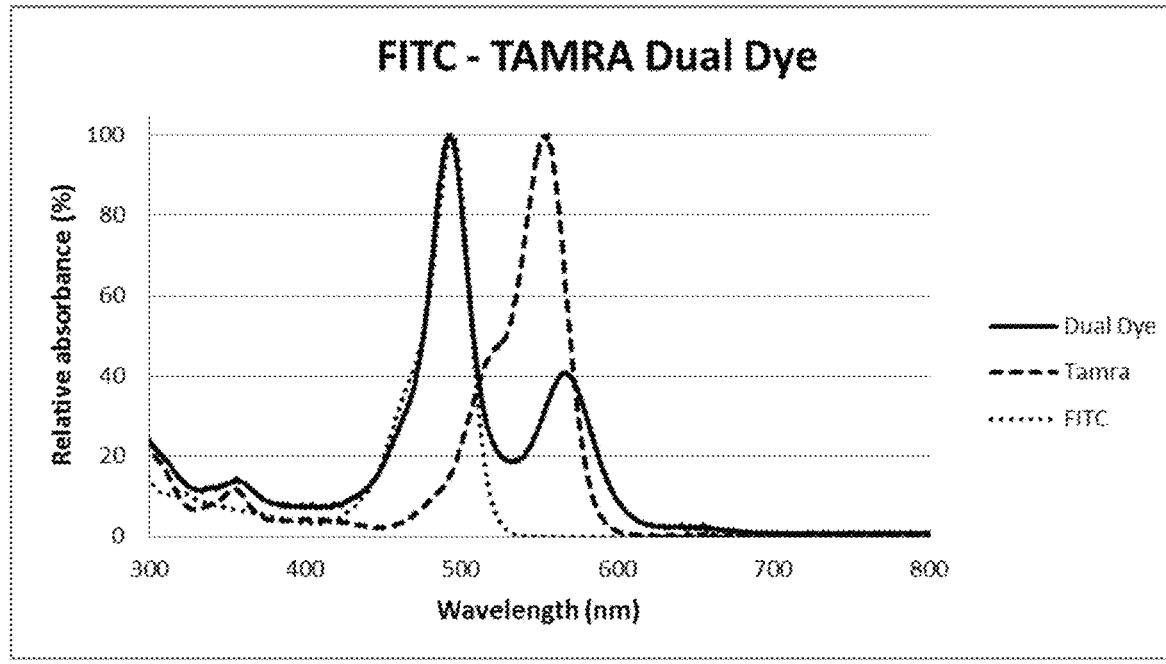
FIG. 13B provides spectra for a FITC-TAMRA duel dye conjugate as compared to single dye color spectra.
Figure 13C:
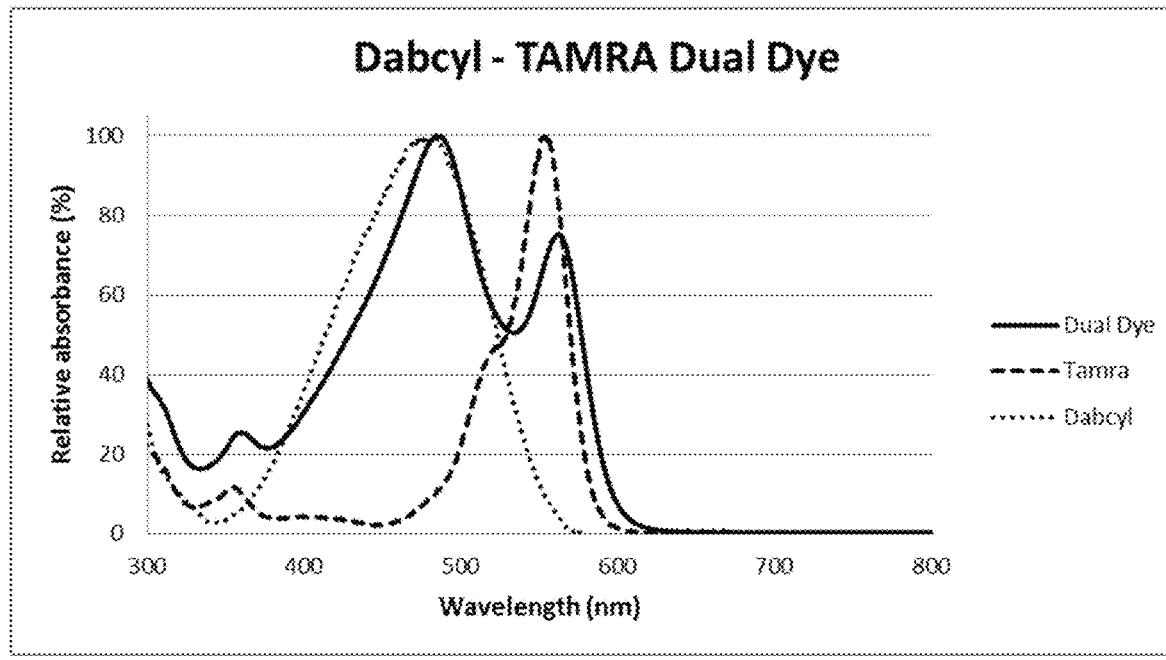
FIG. 13C provides spectra for a Dabcyl-TANARA duel dye conjugate as compared to single dye color spectra.
Figure 13D:
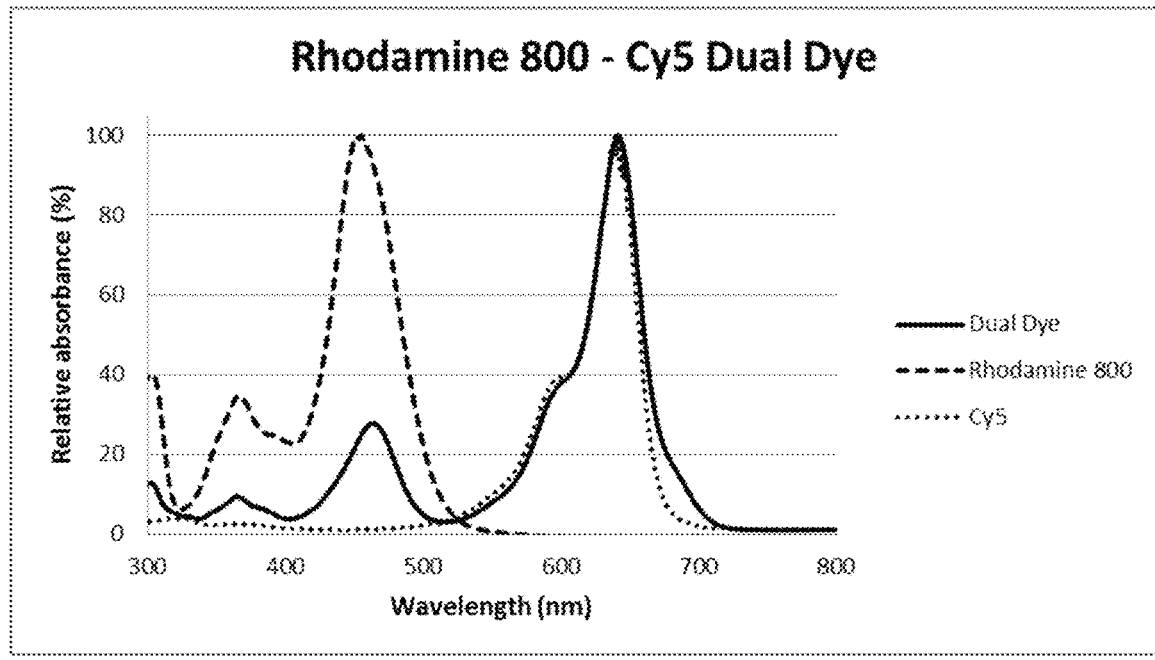
FIG. 13D provides spectra for a Rhodamine 800-Cy5 duel dye conjugate as compared to single dye color spectra.

By way of example and with reference to FIG. 11, linking a yellow chromogen and a cyan chromogen to a tissue reactive moiety through a multi-functional linker provides for a multi-dye conjugate which provides a green color. Likewise, linking a yellow chromogen and a purple chromogen to a tissue reactive moiety through a multi-functional linker provides for a multi-dye conjugate which provides a red color. Similarly, linking a cyan chromogen and a violet chromogen to a tissue reactive moiety through a multi-functional linker provides for an indigo color. While the schematic above and the illustrations in FIG. 11 depict two chromogens coupled to a tissue reactive moiety, the skilled artisan will appreciate that more than two chromogens may be coupled to any tissue reactive moiety, provided that the multi-functional linker comprises sufficient sites for conjugation.

Yet other arrangements are contemplated. In some arrangements, the multi-dye conjugates are a hybrid of "linear" and "branched" arrangements, such as depicted in the schematics which follow. While the schematics which follow indicate that the multi-functional linkers are conjugated to chromogens, any detectable moiety may be utilized. Moreover, the skilled artisan will appreciate that the multi-functional linker or chromogens may be directly or indirectly coupled to each other.

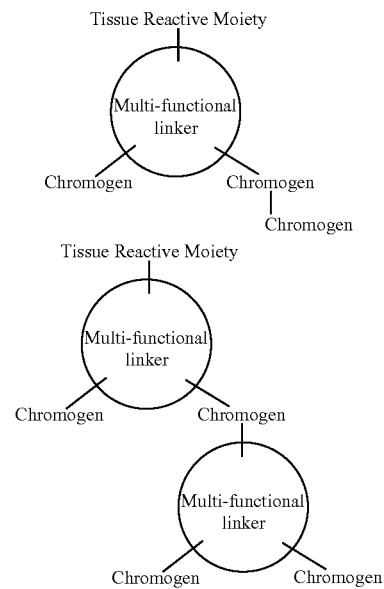

-continued

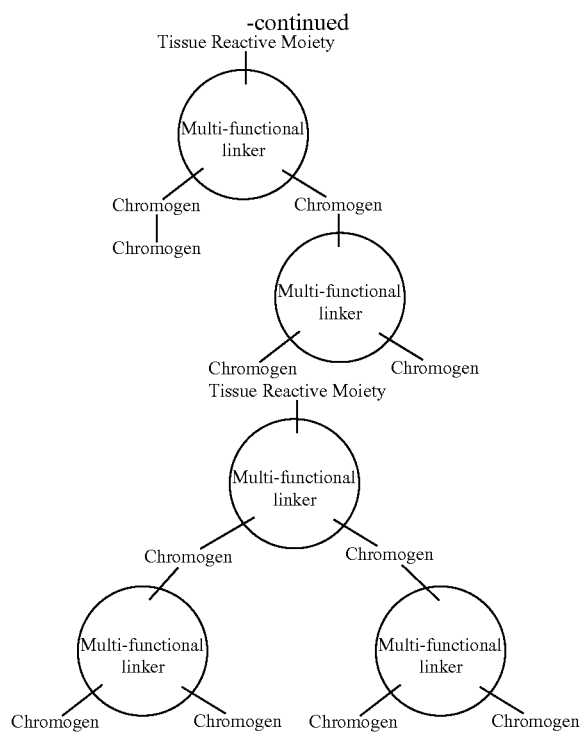

Yet other arrangements include a "highly branched" configuration, where multiple multi-functional linkers are coupled to form branched conjugates, such as in the schemes illustrated below. In these "highly branched" configurations, the multi-functional linker may be a dendrimer or a polymer. While the schematics which follow indicate that the multi-functional linkers are conjugated to chromogens, any detectable moiety may be utilized. Moreover, the skilled artisan will appreciate that the multi-functional linker or chromogens may be directly or indirectly coupled to each other.

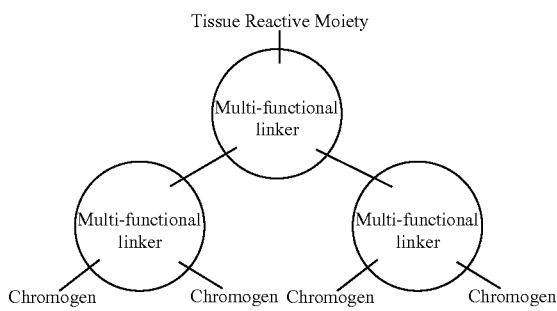

In some embodiments, the multi-dye conjugates of the present disclosure have the structure of Formula (I):

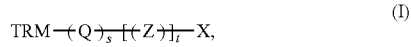

where "TRM" is a tissue reactive moiety;

Q is a branched or unbranched, linear or cyclic, substituted or unsubstituted group having between 2 and 40 carbon atoms, and optionally having one or more heteroatoms selected from O, N, or S;

Z is a bond or a branched or unbranched, linear or cyclic, substituted or unsubstituted, saturated or unsaturated, group having between 2 and 20 carbon atoms, and optionally having one or more heteroatoms selected from O, N, or S;

X is H, -[(Q)$_d$-[A]$_n$]$_e$; —N—([Z]—[X])$_2$; or —C(H)([Z]—[X])$_2$;

A is a detectable moiety;

d is 0 or 1;

e is an integer ranging from 1 to 4;

s is 0 or an integer ranging from 1 to 4; and t is 0 or an integer ranging from 1 to 10;

provided that the multi-dye conjugates of Formula (I) comprise at least two A groups.

As used herein, the term "tissue reactive" refers to a moiety that is capable of reacting with an enzyme. As such, when a conjugate comprising a tissue reactive moiety is reacted with an appropriate enzyme, the tissue reactive moiety portion of the multi-dye conjugate undergoes a structural, conformational, and/or electronic change, thereby providing a tissue reactive species (an intermediate) suitable for bonding directly or indirectly onto (or, to the extent possible, within) a biological sample. For example, where the tissue reactive moiety is a tyramide or derivative thereof, when the tyramide reacts with an appropriate enzyme (e.g. an HRP), a tyramide radical species is formed. This highly reactive tyramide radical species is capable of bonding to tyrosine residues in biological samples. In a similar manner, where the tissue reactive moiety is a quinone methide precursor or derivative thereof, upon reaction with an appropriate enzyme (e.g. AP), the quinone methide precursor is converted to a quinone methide (or respective derivative thereof), which is believed to be highly reactive with nucleophiles in a biological sample. The role of the tissue reactive moiety portion of any conjugate, its interaction with a suitable enzyme, and the formation of an immobilized tissue-conjugate complex suitable for detection is described further herein.

In some embodiments, the tissue reactive moiety is a quinone methide precursor or a derivative thereof. In some embodiments, a quinone methide precursor moiety has the structure provided by Formula (II):

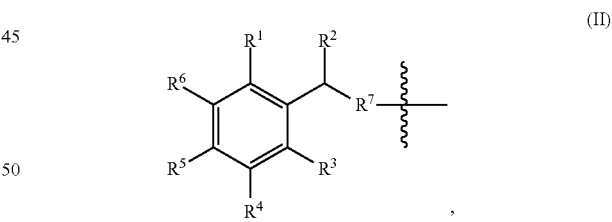

$R^1$ is a group selected from phosphate, amide, nitro, urea, sulfate, methyl, ester, beta-lactam, or a sugar;

$R^2$ is a halide;

$R^3$, $R^4$, $R^5$, and $R^6$ are independently selected from hydrogen or an aliphatic group having between 1 and 4 carbon atoms; and $R^7$ is —(CH$_2$)$_w$NH—, —O(CH$_2$)$_w$NH—, —N(H)C(O)(CH$_2$)$_w$NH—, —C(O)N(H)(CH$_2$)$_w$NH—, —(CH$_2$)$_w$O—, —O(CH$_2$)$_w$O—, —O(CH$_2$CH$_2$O)$_w$—, —N(H)C(O)(CH$_2$)$_w$O—, —C(O)N(H)(CH$_2$)$_w$O—, —C(o)N(H)(CH$_2$CH$_2$O)$_w$—, —(CH$_2$)$_w$S—, —O(CH$_2$)$_w$S—, —N(H)C(O)(CH$_2$)$_w$S—, —C(O)N(H)(CH$_2$)$_w$S—, —(CH$_2$)$_w$NH—, —C(O)N(H)(CH$_2$CH$_2$O)$_w$CH$_2$CH$_2$NH, —C(O)(CH$_2$CH$_2$O)$_w$CH$_2$CH$_2$NH—, —C(O)N(H)(CH$_2$)NHC(O)

CH(CH₃)(CH₂)$_w$NH—, or —N(H)(CH₂)$_w$NH—, where w is an integer ranging from 1 to 12.

In other embodiments, the quinone methide precursor moiety has the structure provided by Formula (IIa):

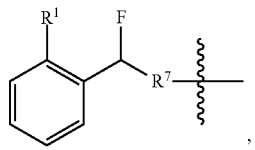

(IIa)

In other embodiments, the quinone methide precursor moiety has the structure provided by Formula (IIb):

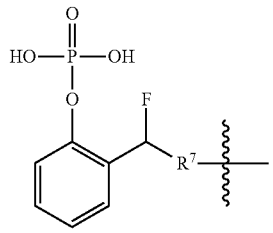

(IIb)

where R⁷ —(CH₂)$_w$NH—, —O(CH₂)$_w$NH—, —N(H)C(O)(CH₂)$_w$NH—, C(O)N(H)(CH₂)$_w$NH—, —(CH₂)$_w$O—, —O(CH₂)$_w$O—, —O(CH₂CH₂O)$_w$—, —N(H)C(O)(CH₂)$_w$O—, —C(O)N(H)(CH₂)$_w$O—, —C(o)N(H)(CH₂CH₂O)$_w$—, —(CH₂)$_w$S—, —O(CH₂)$_w$S—, —N(H)C(O)(CH₂)$_w$S—, —C(O)N(H)(CH₂)$_w$S—, —(CH₂)$_w$NH—, —C(O)N(H)(CH₂CH₂O)$_w$CH₂CH₂NH, —C(O)(CH₂CH₂O)$_w$CH₂CH₂NH—, —C(O)N(H)(CH₂)NHC(O)CH(CH₃)(CH₂)$_w$NH—, or —N(H)(CH₂)$_w$NH—, where w is independently an integer ranging from 1 to 12. In some embodiments, R⁷ is C(O)N(H)(CH₂)$_w$NH and w is as defined above. In other embodiments, R⁷ is C(O)N(H)(CH₂)$_w$NH and w ranges from 2 to 6.

In other embodiments, the quinone methide precursor moiety has the structure provided by Formula (IIc):

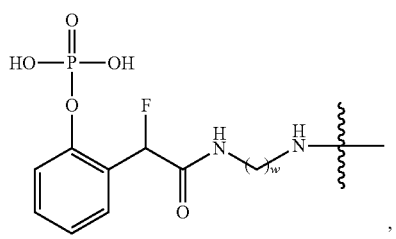

(IIc)

where w ranges from 1 to 12. In some embodiments w ranges from 1 to 8. In other embodiments, w ranges from 2 to 8. In yet other embodiments, w ranges from 2 to 6. In further embodiments, w is 6.

In some embodiments, the quinone methide precursor moiety portion of any multi-dye conjugate is derived from one of the derivatives which follow. The skilled artisan will appreciate that the derivatives which follow are suitable starting materials for coupling to a multi-functional linker, detectable moiety, or other component of the multi-dye conjugate.

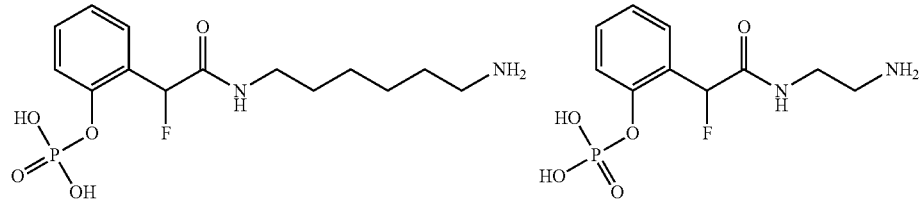

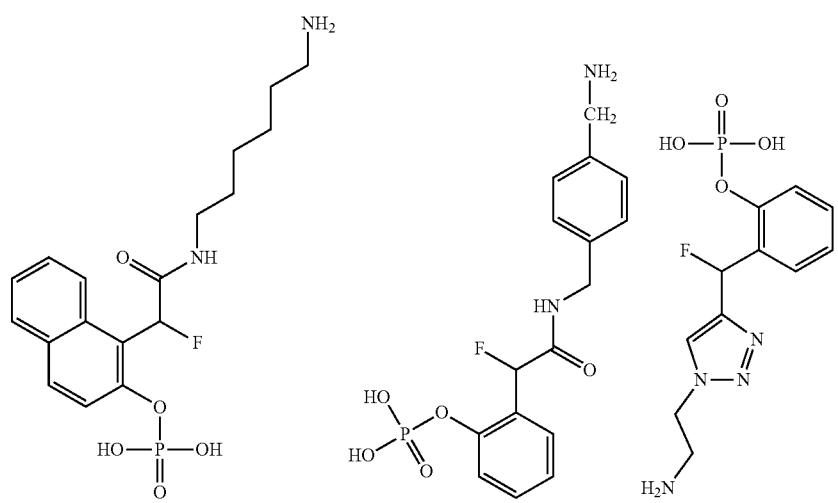

-continued

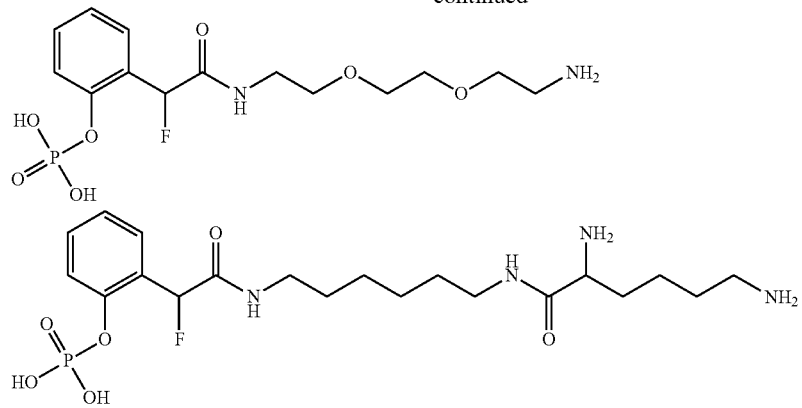

In some embodiments, the tissue reactive moiety is a tyramide or a derivative thereof. In some embodiments, the tyramide has the structure provided by Formula (III):

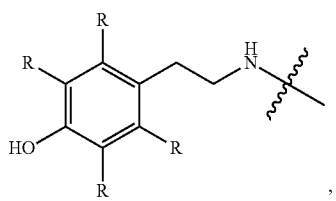

(III)

wherein each R group is independently selected from hydrogen or lower alkyl group having between 1 and 4 carbon atoms.

In other embodiments, the tyramide moiety has the structure provided by Formula (IIIa):

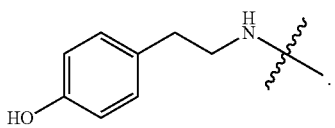

(IIIa)

The skilled artisan will appreciate that tyramine or derivatives of Formulas (III) and (IIIa) are suitable starting materials for coupling to a multi-functional linker, detectable moiety, or other component of the multi-dye conjugate.

In some embodiments, A is a chromogen. Non-limiting examples of chromogens are include TAMRA, Dabsyl, Dabcyl, Cy3, CyB, Cy3.5, Cy5, Cy5.5, Cy7, rhodamine 800 and fluorescein. In some embodiments, the chromogens are selected from chromogenic compounds having at least one conjugation site capable of coupling directly or indirectly (such as through a group Q) to a tissue reactive moiety, a group Z, or another chromogen. Non-limiting examples of chromogens having multiple conjugation sites include TAMRA, 5,6-carboxyfluorescein, FITC, 5,6-carboxyrhodamine 110, 5,6-carboxyrhodamine 6G, 5,6-carboxy-X-rhodamine, and rhodamine B isothiocyanate. Other rhodamine and fluorescein derivatives that are substituted at the 5,6-position may also be utilized.

As noted herein, Q may be a branched or unbranched, linear or cyclic, substituted or unsubstituted group having between 2 and 40 carbon atoms, and optionally having one or more heteroatoms selected from O, N, or S. In some embodiments, Q may comprise carbonyl, amine, ester, ether, amide, imine, thione or thiol groups. In some embodiments, Q is a branched or unbranched linear group having between 2 and 20 carbon atoms, optionally having one or more heteroatoms selected from O, N, or S, and one or more terminal groups selected from an amine, a carbonyl, ester, ether, amide, imine, thione, or thiol. In other embodiments, Q is a branched or unbranched linear group having between 2 and 20 carbon atoms, optionally having one or more oxygen heteroatoms. In yet other embodiments, the group Q comprises components intended to increase the water-solubility of the molecule.

In some embodiments, the group Q is designed to act as a "spacer" separating nearby multi-dye conjugate components (e.g. to mitigate steric interactions between adjacent chromogens). In other embodiments, the group Q is designed to increase the water solubility of the multi-dye conjugates or to couple two multi-dye conjugate components together.

In some embodiments, Q has the structure depicted in Formula (IVa):

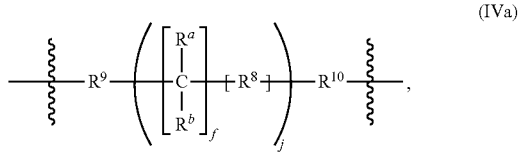

(IVa)

wherein f is 0, 1, or 2;

$R^8$ is a bond, O, S, or $N(R^c)(R^d)$;

$R^a$ and $R^b$ are independently H, a $C_1$-$C_4$ alkyl group, F, Cl, or —$N(R^c)(R^d)$;

$R^c$ and $R^d$ are independently selected from $CH_3$ or H;

$R^9$ and $R^{10}$ are independently a bond or a group selected from carbonyl, amide, imide, ester, ether, amine, thione, thiol; and j is an integer ranging from 1 to 8.

In some embodiments, at least one of $R^a$ or $R^b$ is H. In some embodiments, at least one of $R^a$ or $R^b$ is H and f is 1. In some embodiments, at least one of $R^a$ or $R^b$ is H, f is 1 and s is at least 2.

In some embodiments, Q has the structure depicted in Formula (IVb):

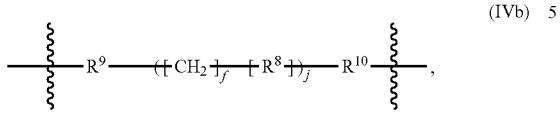
(IVb)

wherein f is 0, 1, or 2;

$R^8$ is a bond, O, S, or $N(R^c)(R^d)$;

$R^c$ and $R^d$ are independently $CH_3$ or H;

$R^9$ and $R^{10}$ are independently a bond or a group selected from carbonyl, amide, imide, ester, ether, amine, or thiol; and j is an integer ranging from 1 to 8.

In some embodiments, f is 1 and s is at least 2. In some embodiments, $R^8$ is a bond; f is 1; s is 2 to 10; and $R^9$ and $R^{10}$ are as defined above. In other embodiments, $R^8$ is a bond; f is 1; s is 2 to 6; and $R^9$ and $R^{10}$ are as defined above. In other embodiments, $R^8$ is a bond; f is 1; s is 2 to 4; and $R^9$ and $R^{10}$ are both amines.

In some embodiments, Q has the structure depicted in Formula (IVc):

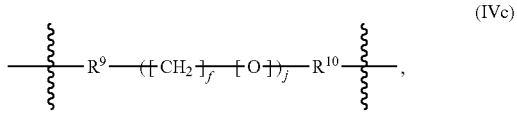
(IVc)

wherein f is 0, 1, or 2; and j is an integer ranging from 1 to 8.

In some embodiments, f is 1; $R^9$ and $R^{10}$ are independently a bond or a group selected from carbonyl, amide, imide, ester, ether, amine, or thiol; and s is at least 2. In some embodiments, f is 1 and s is 2. In some embodiments, f is 1 and s is 3. In some embodiments, f is 1 and s is 4.

The alkylene oxide based Q groups of Formulas (IVa), (IVb), and (IVc), are represented herein by reference to glycols, such as ethylene glycols. In some embodiments, the incorporation of such alkylene oxide linkers is believed to increase the hydrophilicity of the multi-dye conjugate. A person of ordinary skill in the art will appreciate that, as the number alkylene oxide repeat units in the linker increases, the hydrophilicity of the conjugate also may increase. Additional heterobifunctional polyalkyleneglycol spacers useful for practicing certain disclosed embodiments of the present disclosure are described in assignee's co-pending applications, including "Nanoparticle Conjugates," U.S. patent application Ser. No. 11/413,778, filed Apr. 28, 2006; "Antibody Conjugates," U.S. application Ser. No. 11/413,415, filed Apr. 27, 2006; and "Molecular Conjugate," U.S. Provisional Patent Application No. 60/739,794, filed Nov. 23, 2005; all of which applications are incorporated herein by reference.

In some embodiments of Formula (IVa), the groups $C(R^a)(R^b)$ and $R^8$ form a cyclic aliphatic group. In some embodiments, Q has the structure depicted in Formula (IVd):

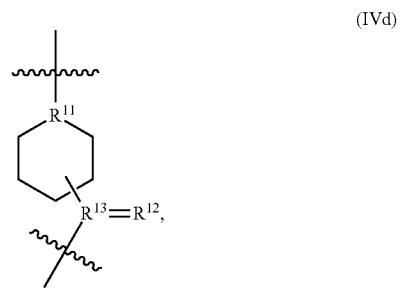
(IVd)

wherein $R^{11}$ is N or S;

$R^{12}$ is O, N, or S; and $R^{13}$ is C or N;

with the proviso that when $R^{12}$ is N or S, $R^{13}$ is C; and with the proviso that when $R^{13}$ is N, $R^{12}$ is C. In some embodiments, Q is derived from 4-piperidinecarboxylic acid.

As noted herein, Z may be a bond or a branched or unbranched, linear or cyclic, substituted or unsubstituted group having between 2 and 20 carbon atoms, and optionally having one or more heteroatoms selected from O, N, or S. In some embodiments, Z may comprise carbonyl, amine, ester, ether, amide, imine, thione, or thiol groups. In some embodiments, the group Z is representative of the multifunctional linkers or hetero-bifunctional linker described herein, and the compounds so represented are designed to allow for branched or highly branched multi-dye conjugates. The skilled artisan will appreciate that, when taken together, groups Q and Z allow for the coupling of different spacers, PEG groups, linkers, etc.

In some embodiments, Z has the structure of Formula (Va):

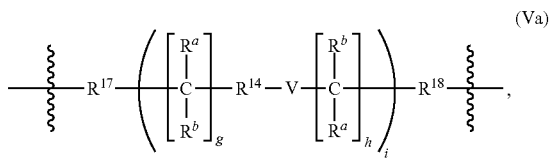
(Va)

wherein $R^{17}$ and $R^{18}$ are independently a bond or a group selected from carbonyl, amide, imide, ester, ether, —NH, —N—, thione, or thiol;

$R^{14}$ is a bond, a carbonyl, an imine, or a thione;

V is a bond, —$C(R^{15})(R^{16})$—, —O—, —S—, —$N(R^{16})$—, —N(X)—; —$C(R^{15})(X)$; —$C(X)_2$—, or —$C(R^{15})(N(R^{16})(X))$;

X is as defined herein;

$R^a$ and $R^b$ are independently H, a $C_1$-$C_4$ alkyl group, F, Cl, or $N(R^{15})(R^{16})$;

$R^{15}$ and $R^{16}$ are independently a bond or —$CH_3$ or H;

g is 0 or an integer ranging from 1 to 4;

h is 0 or an integer ranging from 1 to 8; and i is 1 or 2.

In some embodiments of Formula (Va), g is 0, $R^{14}$ is a carbonyl, V is —$C(R^{15})(N(R^{16})(X))$, $R^{15}$ is H, $R^{16}$ is H, and h ranges from 2 to 6. In other embodiments of Formula (Va), g is 0, $R^{14}$ is a carbonyl, V is —$C(R^{15})(N(R^{16})(X))$, $R^{15}$ is H, $R^{16}$ is H, and h ranges from 2 to 4. In yet other embodiments of Formula (Va), g is 0, $R^{14}$ is a carbonyl, V is —$C(R^{15})(N(R^{16})(X))$, $R^{15}$ is H, $R^{16}$ is H, and h is 4. In further embodiments of Formula (Va), g is 0, $R^{14}$ is a carbonyl, V is —$C(R^{15})(N(R^{16})(X))$, $R^{15}$ is H, $R^{16}$ is H, $R^a$ and $R^b$ are H, and h ranges from 2 to 4. In yet further embodiments of Formula (Va), g is 0, $R^{14}$ is a carbonyl, V is —$C(R^{15})(N(R^{16})(X))$, $R^{15}$ is H, $R^{16}$ is H, $R^a$ and $R^b$ are H, $R^9$ is a bond, $R^{10}$ is an amine; and h ranges from 2 to 4. In even further embodiments of Formula (Va), g is 0, $R^{14}$ is a carbonyl, V is —$C(R^{15})(N(R^{16})(X))$, $R^{15}$ is H, $R^{16}$ is H, $R^a$ and $R^b$ are H, $R^9$ is a bond, $R^{10}$ is an amine; X is -$[(Q)_d$-$[A]_n]_e$, d, n, and e are each 1, and h ranges from 2 to 4.

In some embodiments, Z has the structure of Formula (Vb):

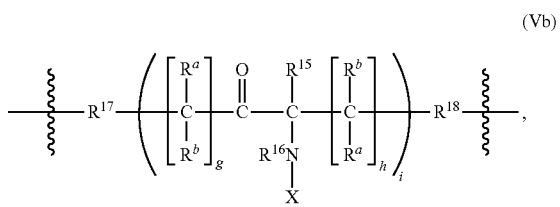

(Vb)

wherein $R^{17}$ and $R^{18}$ are independently a bond or a group selected from carbonyl, amide, imide, ester, ether, —NH, —N—, thione, or thiol;

X is as defined herein;

$R^a$ and $R^b$ are independently H, a $C_1$-$C_4$ alkyl group, F, Cl, or $N(R^{15})(R^{16})$;

$R^{15}$ and $R^{16}$ are independently a bond or —$CH_3$ or H;

g is 0 or an integer ranging from 1 to 4;

h is 0 or an integer ranging from 1 to 8; and i is 1 or 2.

In some embodiments of Formula (Vb), g is 0, $R^{15}$ is H, $R^{16}$ is H, and h ranges from 2 to 6. In other embodiments of Formula (Va), g is 0, $R^{15}$ is H, $R^{16}$ is H, and h ranges from 2 to 4. In yet other embodiments of Formula (Va), g is 0, $R^{15}$ is H, $R^{16}$ is H, and h is 4. In further embodiments of Formula (Va), g is 0, $R^{15}$ is H, $R^{16}$ is H, $R^a$ and $R^b$ are H, and h ranges from 2 to 4. In yet further embodiments of Formula (Va), g is 0, $R^{15}$ is H, $R^{16}$ is H, $R^a$ and $R^b$ are H, $R^9$ is a bond, $R^{10}$ is an amine; and h ranges from 2 to 4. In even further embodiments of Formula (Va), g is 0, $R^{15}$ is H, $R^{16}$ is H, $R^a$ and $R^b$ are H, $R^9$ is a bond, $R^{10}$ is an amine; X is -$[(Q)_d$-$[A]_n]_e$, d, n, and e are each 1, and h ranges from 2 to 4.

In some embodiments, Z has the structure of Formula (Vc):

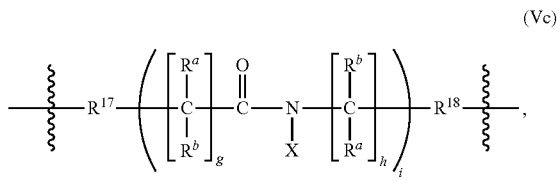

(Vc)

wherein $R^{17}$ and $R^{18}$ are independently a bond or a group selected from carbonyl, amide, imide, ester, ether, —NH, —N—, thione, or thiol;

X is as defined herein;

$R^a$ and $R^b$ are independently H, a $C_1$-$C_4$ alkyl group, F, Cl, or $N(R^{15})(R^{16})$;

g is 0 or an integer ranging from 1 to 4;

h is 0 or an integer ranging from 1 to 8; and i is 1 or 2.

In some embodiments of Formula (Vc), g is 2 to 4, and h is 2 to 4. In other embodiments of Formula (Vc), g is 2, h is 2, and $R^{18}$ is a bond. In yet other embodiments of Formula (Vc), g is 2, h is 2, $R^{18}$ is a bond, and X is -$[(Q)_d$-$[A]_n]_e$.

In some embodiments, Z has the structure of Formula (Vd):

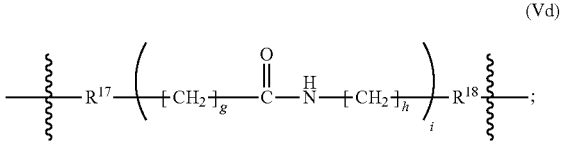

(Vd)

wherein $R^{17}$ and $R^{18}$ are independently a bond or a group selected from carbonyl, amide, imide, ester, ether, —NH, —N— or thiol;

g is 0 or an integer ranging from 1 to 4;

h is 0 or an integer ranging from 1 to 8; and i is 1 or 2.

In some embodiments of Formula (Vd), g is 2 to 4, and h is 2 to 4.

In other embodiments of Formula (Vd), g is 2, h is 2, and $R^{18}$ is a bond.

Examples of the multi-dye conjugates according to Formula (I) include those provided below, where A is a detectable moiety:

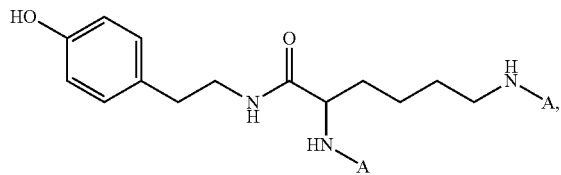

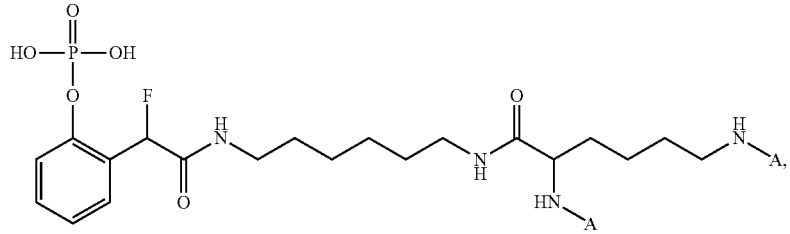

-continued
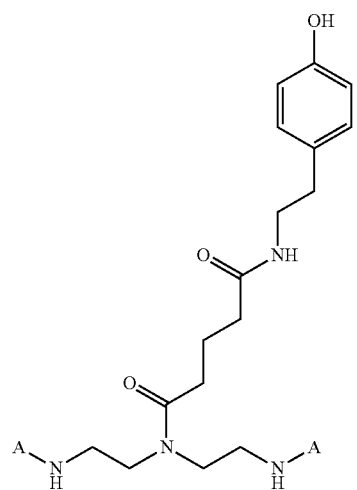
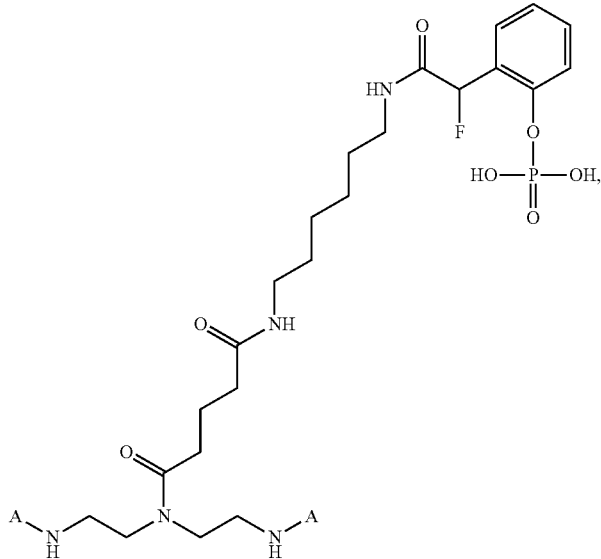
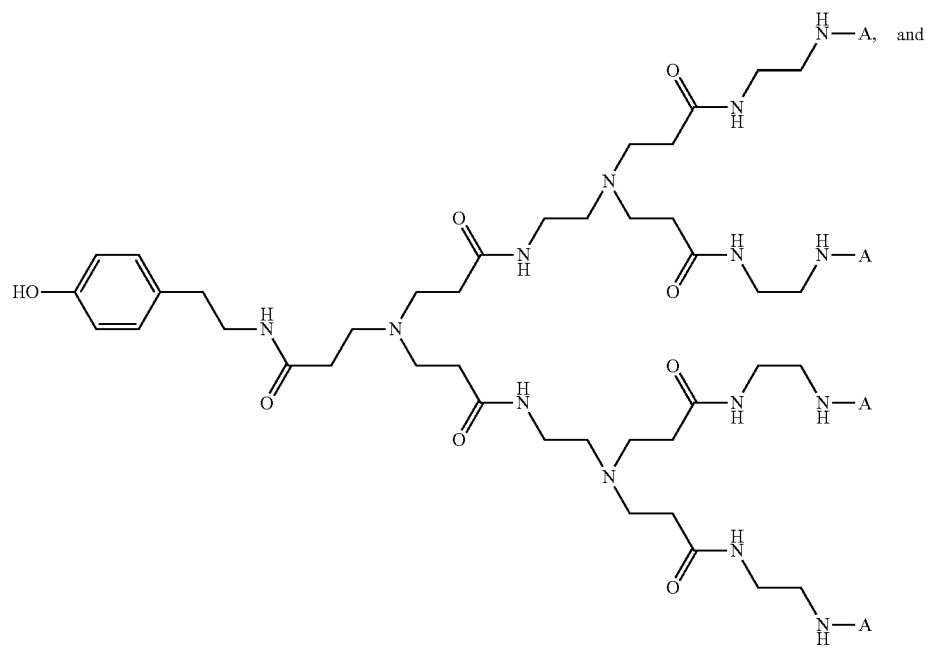

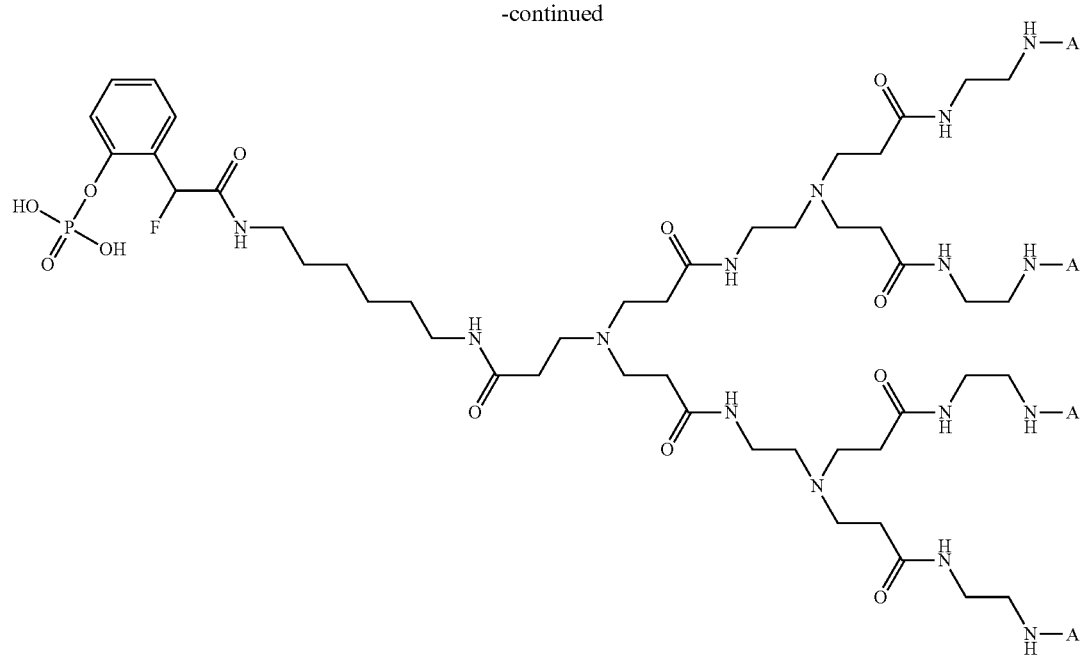
Specific examples of multi-dye conjugates according to Formula (I) are set forth below:
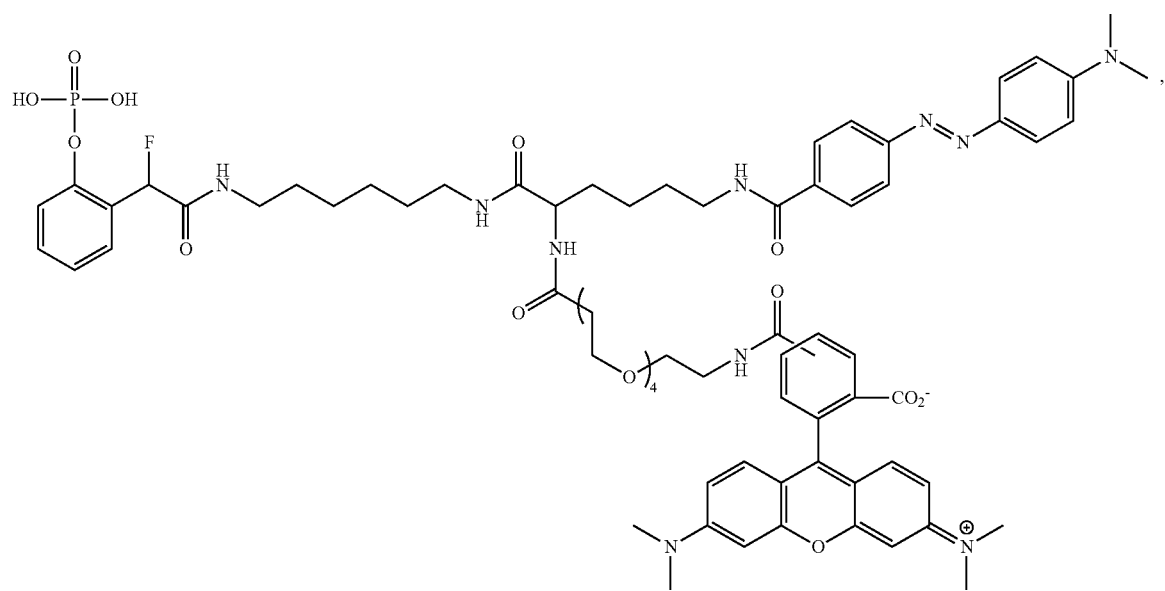

-continued
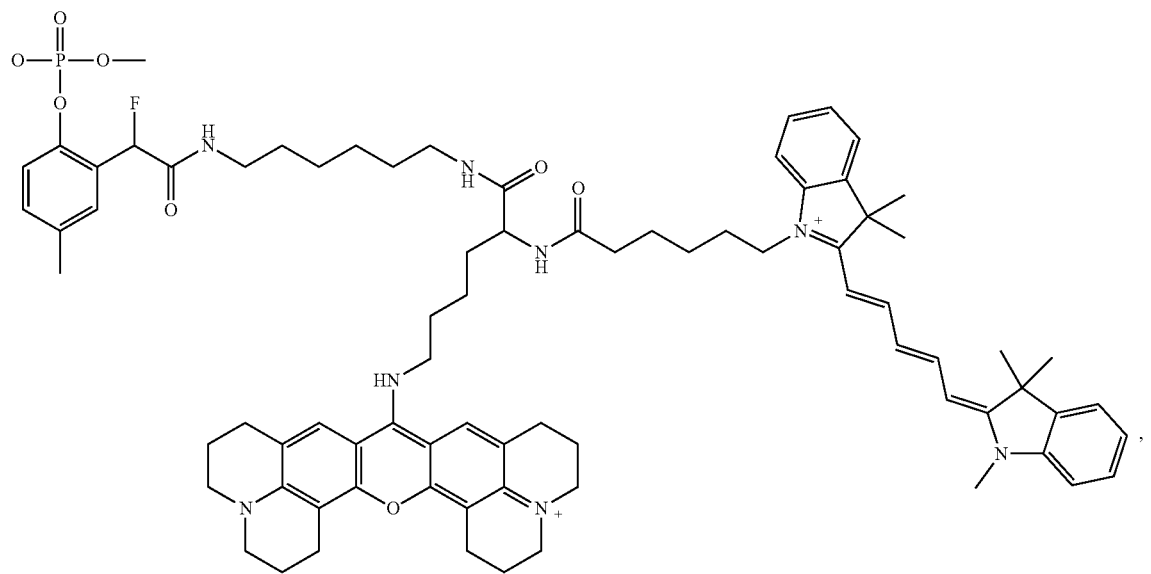
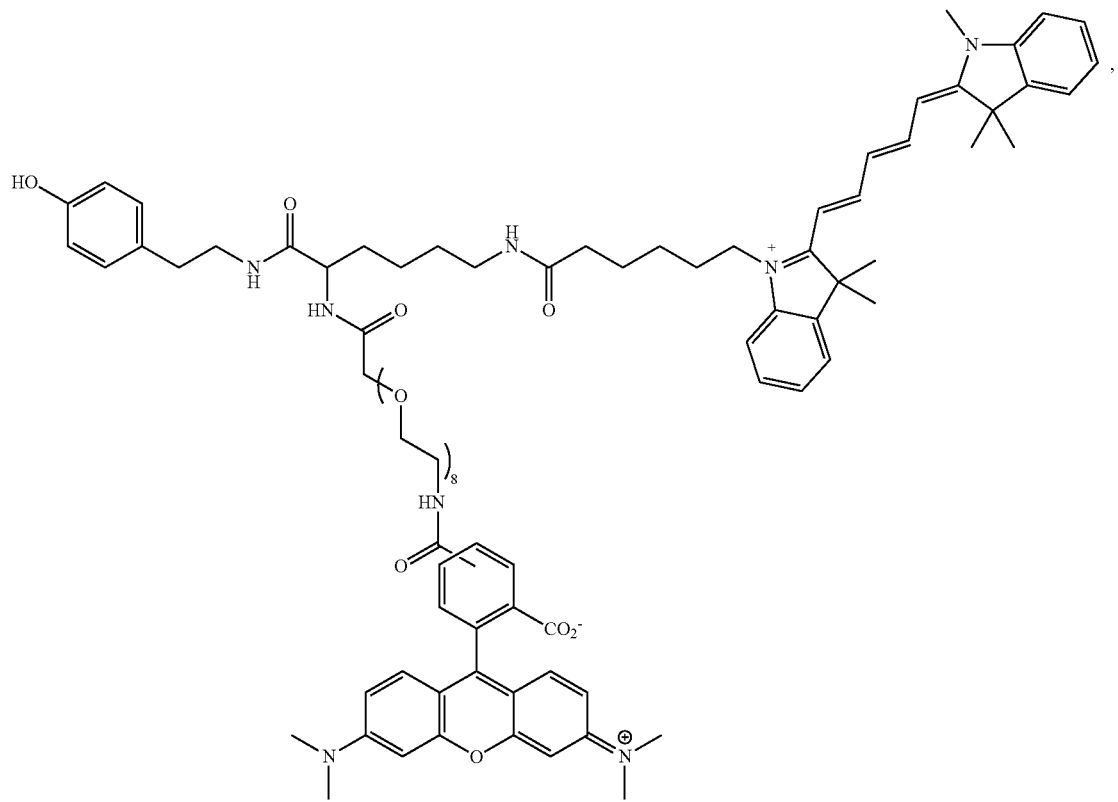

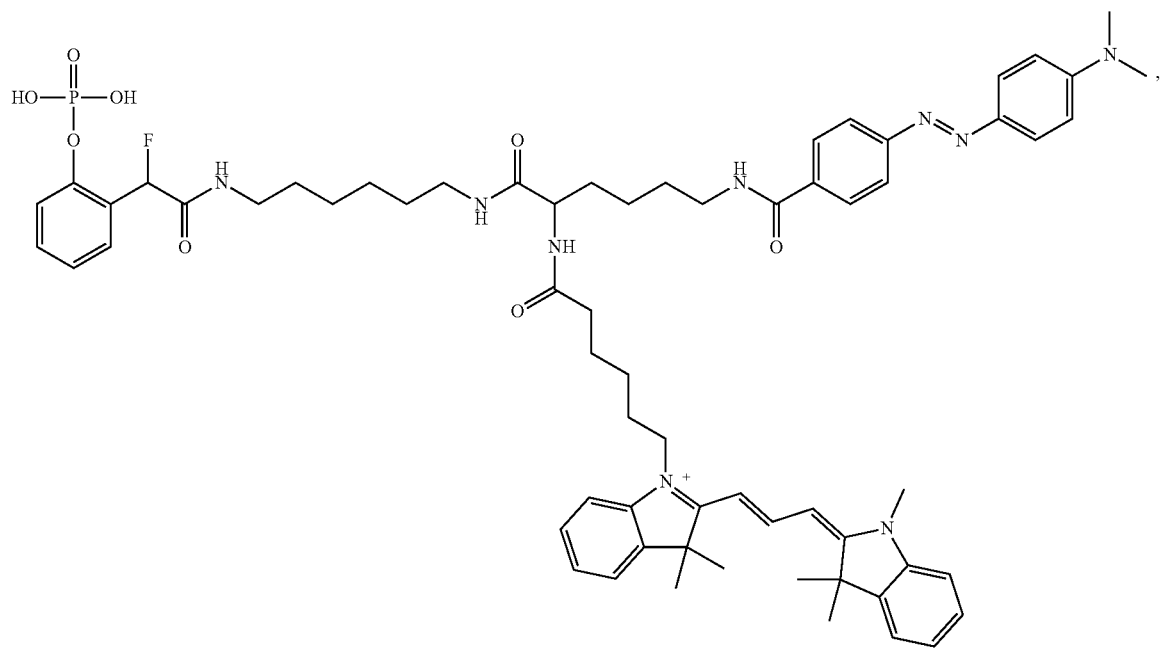
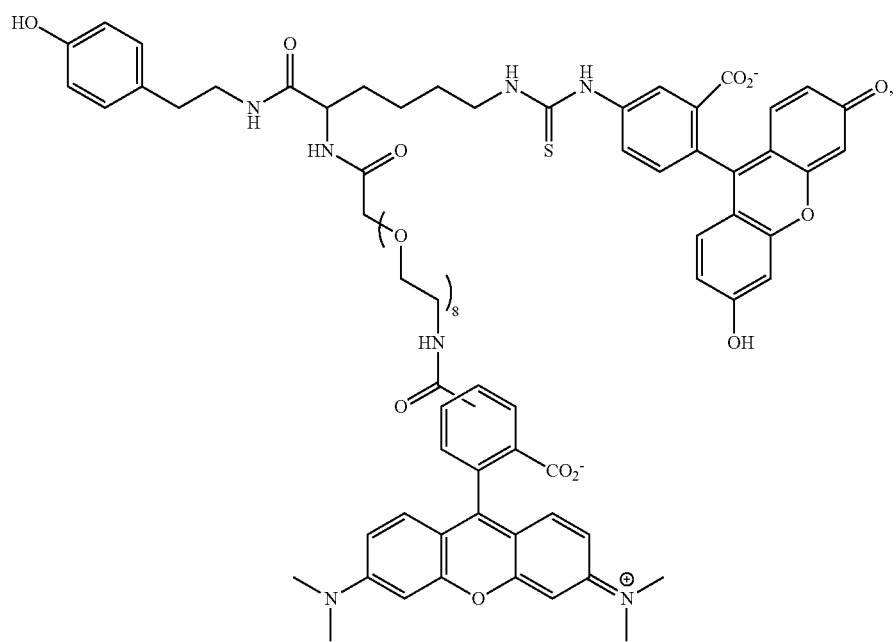

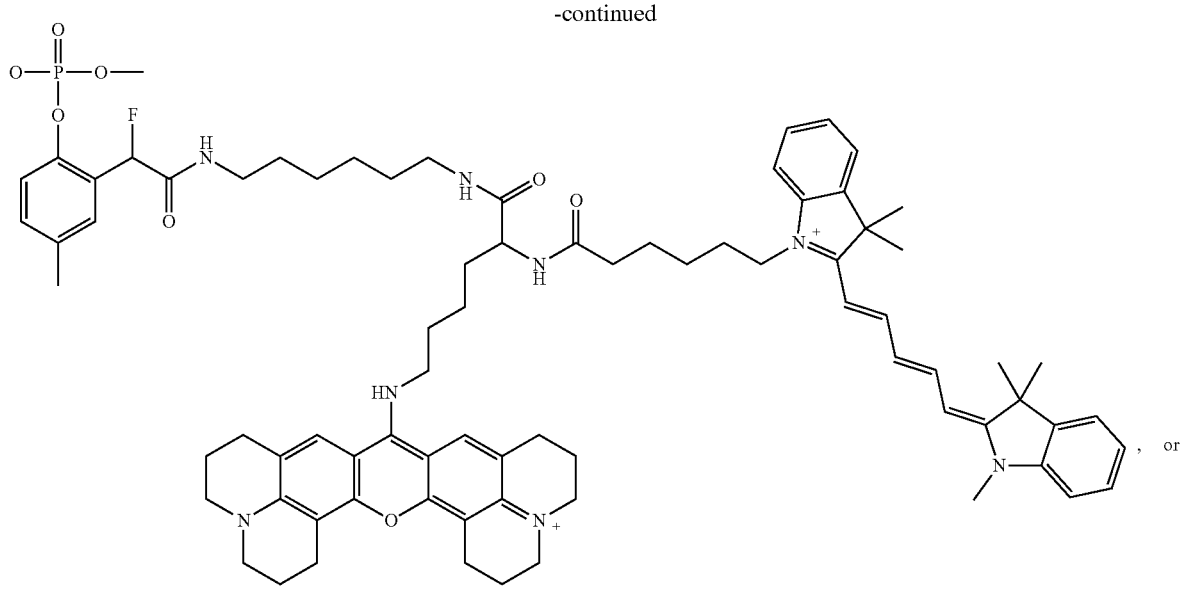

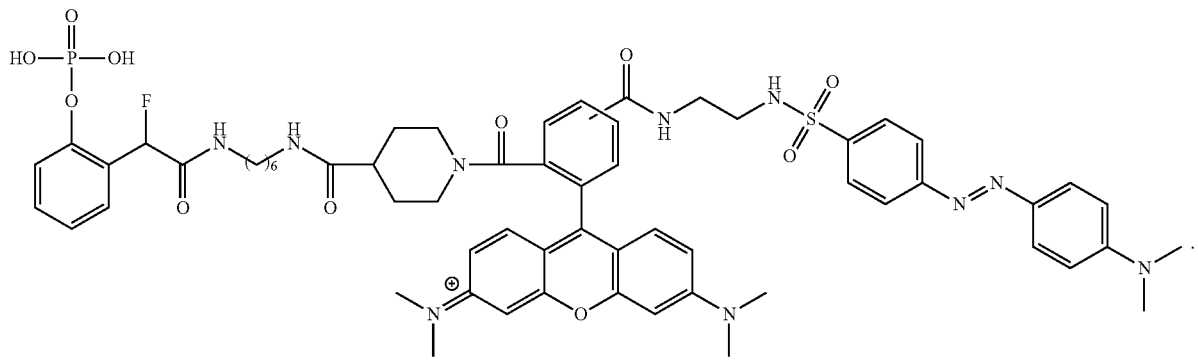

Synthesis of Multi-Dye Conjugations

The multi-dye conjugates of the present disclosure may be synthesized according to any means known to those of ordinary skill in the art. In general, the multi-dye conjugates of the present disclosure may be synthesized by coupling multi-functional linkers or spacers to either detectable moieties and/or tissue reactive moieties. The skilled artisan will be able to select appropriate starting materials that comprise functional groups that are able to react with each other. For example, if a multi-functional linker comprises an unprotected amine, the skilled artisan will be able to select a chromophore having a functional group capable of reacting with an amine (e.g. and NHS-ester). Likewise, if a multi-functional linker comprises a carboxylic acid group, the skilled artisan will be able to select a moiety having a functional group capable of reacting with the carboxylic acid (e.g. an amine).

In some embodiments, a chromogen already comprising a protected multi-functional linker moiety is first coupled with a quinone methide precursor for form a quinone-methide precursor moiety-first chromogen conjugate. The quinone-methide precursor moiety-first chromogen conjugate is then reacted with a second chromogen to form the respective multi-dye conjugate as provided in the schematic below. In this particular example, the multi-functional linker is lysine.

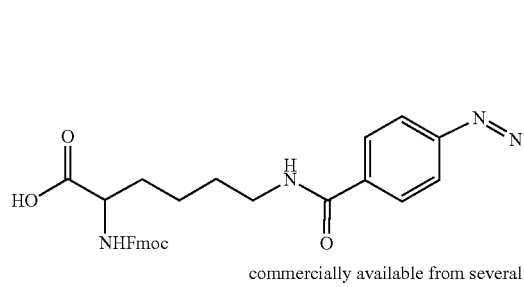
commercially available from several

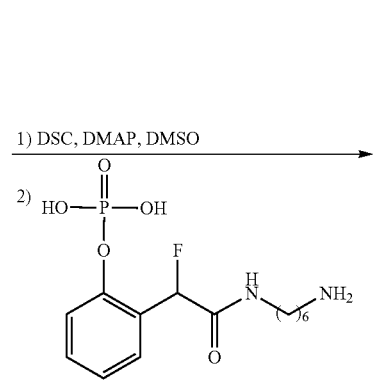

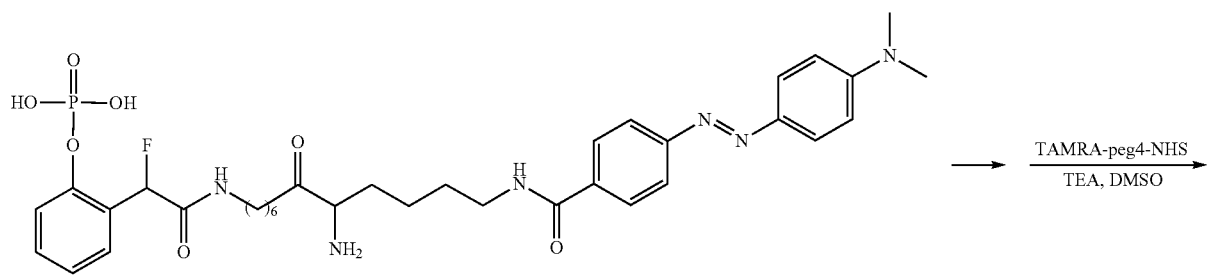

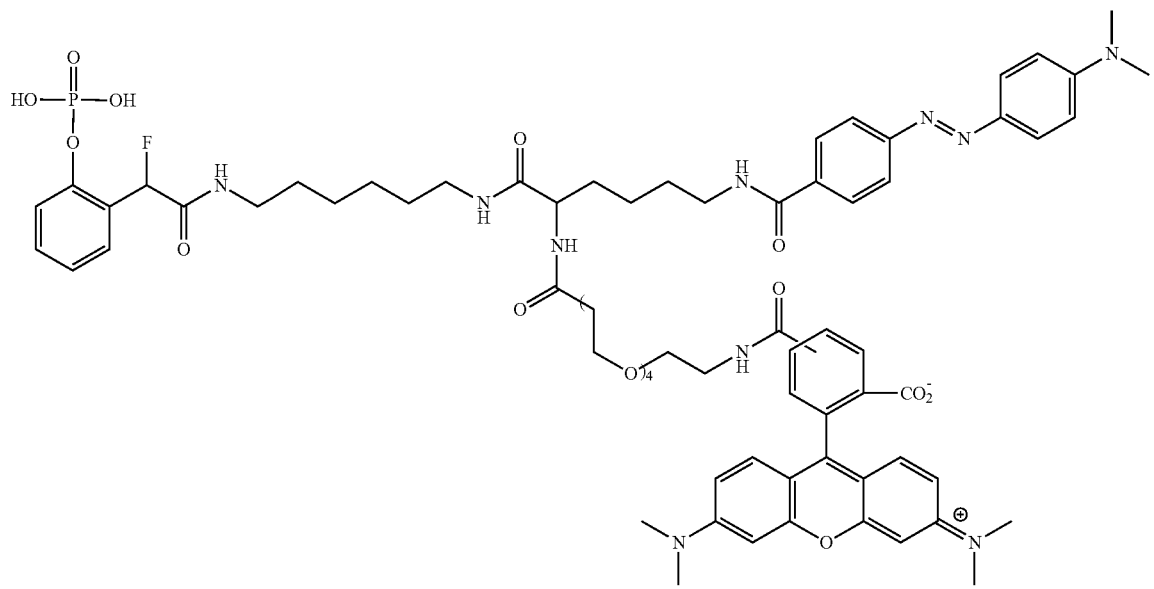

Quinone Methide - Lysine - Dabcyl - TAMRA (RED)

Alternatively, a multi-functional linker having one reactive group protected is first reacted with an appropriately functional chromogen to form a first chromogen-linker conjugate. The first chromogen-linker conjugate may then be reacted with an appropriately functionalized tissue reactive moiety to form a tissue reactive moiety-first chromogen-linker conjugate. The tissue reactive moiety-first chromogen-linker conjugate may then be deprotected, followed by reaction with an appropriately functionalized second chromogen to provide a multi-dye conjugate as illustrated in the schematic which follows. In this particular example, the multi-functional linker is a protected lysine and the tissue reactive moiety is tyramine. The skilled artisan will appreciate that the same reaction conditions may be used to coupled alternative multi-functional linkers to chromogens. The skilled artisan will also appreciate a quinone methide precursor derivative may be substituted for tyramine.

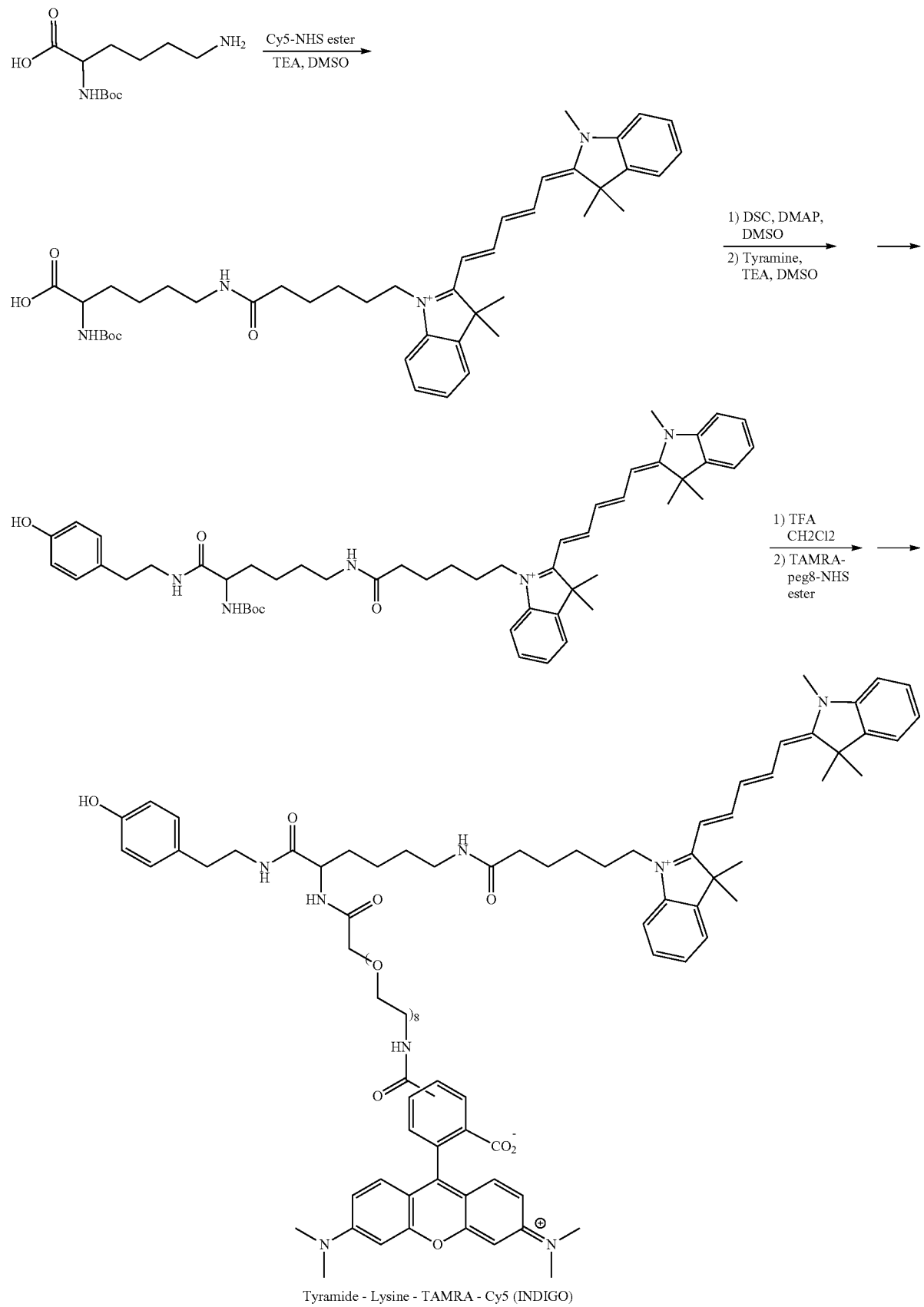
Tyramide - Lysine - TAMRA - Cy5 (INDIGO)

In another alternative synthetic method, a first chromogenic compound is coupled to a protected spacer compound, such as $NH_2CH_2CH_2NHBoc$, to form a conjugate of the chromogen and a spacer. The conjugate of the chromogen and protected spacer is then deprotected and coupled to a second chromogen to form a first two-chromogen conjugate. The two-chromogen conjugate is then reacted with 4-piperidinecarboxylic acid to form a second two-chromogen conjugate. The second two-chromogen conjugate is then reacted with an appropriately functionalized tissue reactive moiety to form the respective multi-dye conjugate, as illustrated in the schematic which follows.

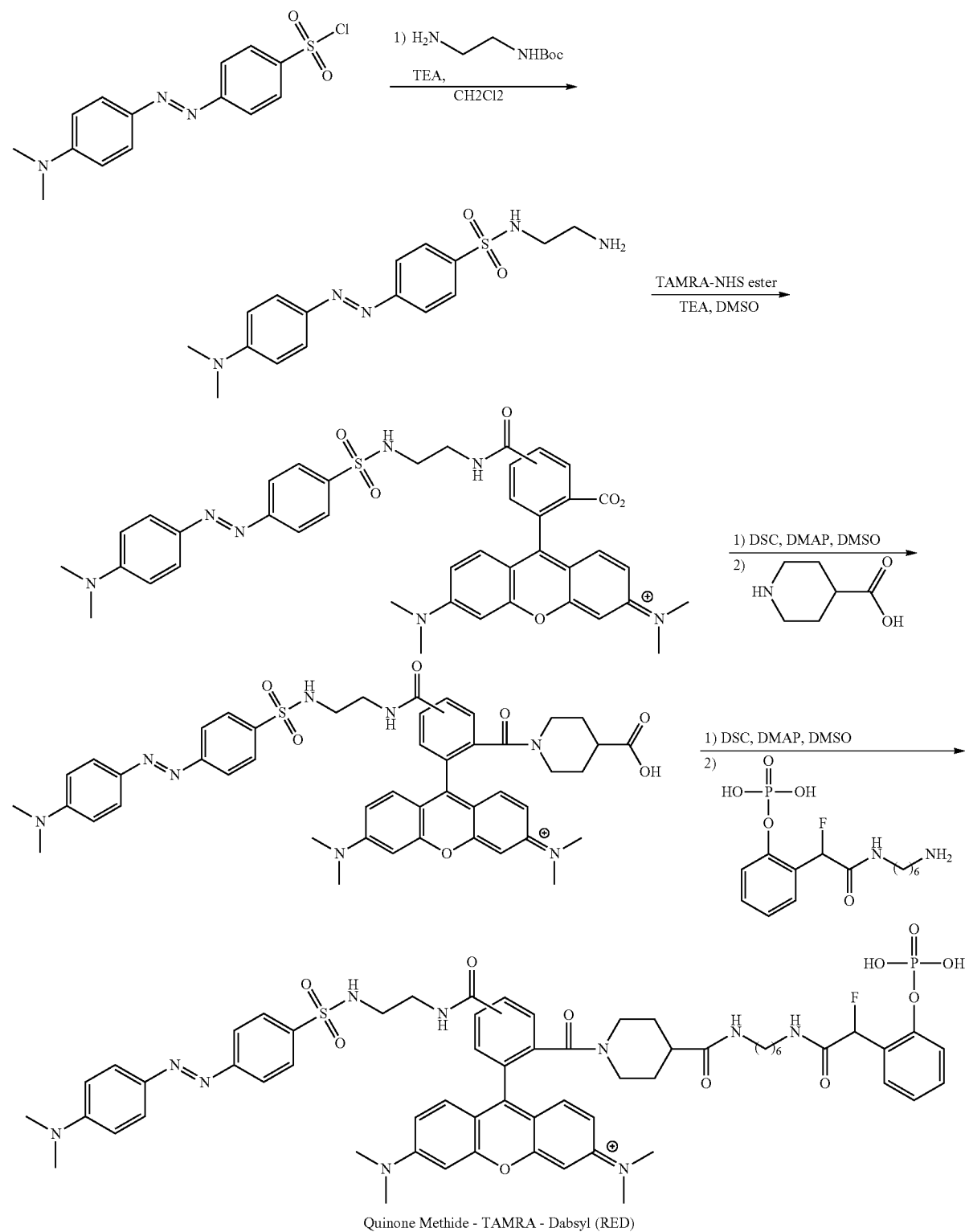

Quinone Methide - TAMRA - Dabsyl (RED)

The synthetic methodology which follows provides an example of coupling more than two chromogens to a tissue reactive moiety, and is illustrated as a convergent synthesis taking place in two stages. In a first stage, a protected multi-functional linker is reacted with an appropriately functionalized chromogen to form a first chromogen-linker conjugate (as illustrated in the above examples). The first chromogen-linker conjugate may then be reacted with an appropriately functionalized tissue reactive moiety to form a tissue reactive moiety-first chromogen-linker conjugate. In a second stage, two equivalents of the same chromogen (or one equivalent of each of two different chromogens) are coupled to a multi-functional linker (e.g. lysine) to form a two-chromogen conjugate. The two-chromogen conjugate is then reacted with the first chromogen-linker conjugate from the first stage to provide a multi-dye conjugate comprising three chromogens.

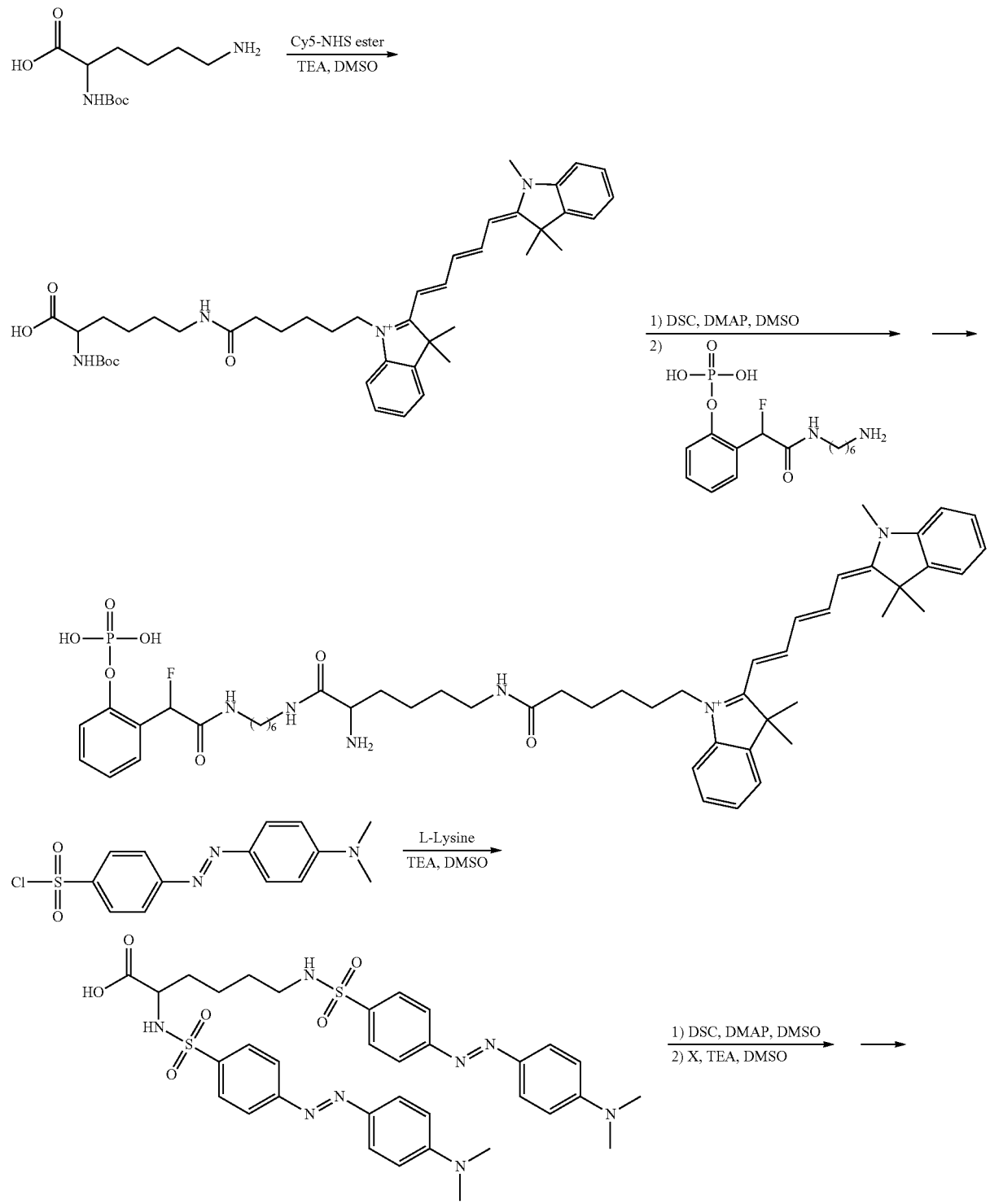

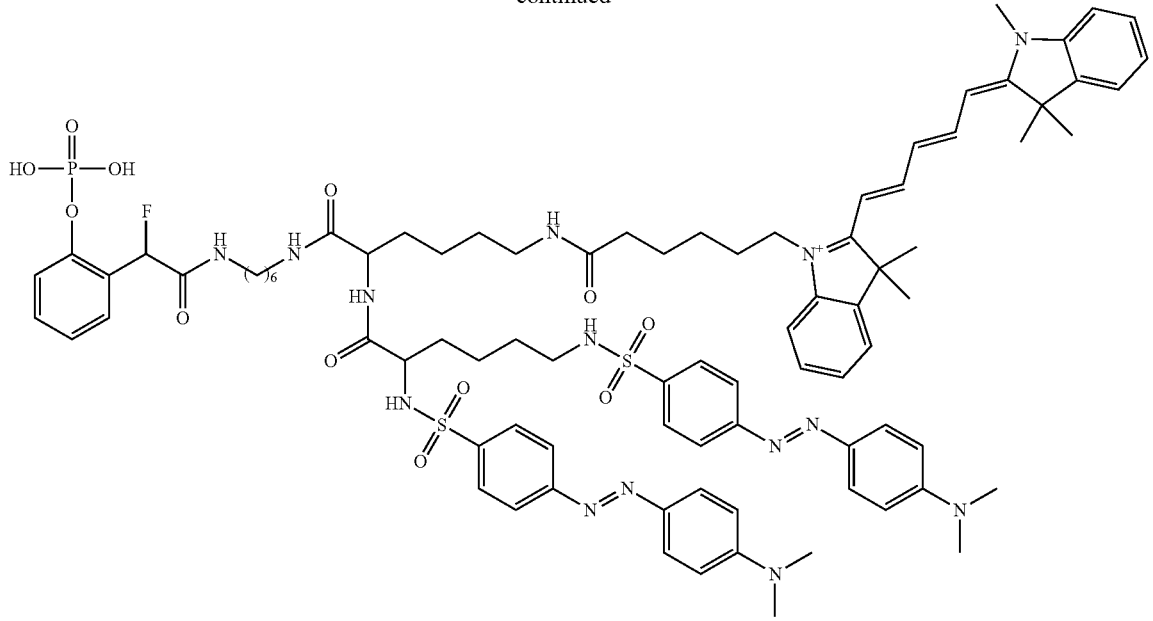

Methods

The present disclosure also provides methods of detecting one or more targets within a biological sample using the multi-dye conjugates disclosed herein. While certain disclosed embodiments, examples, or figures herein may refer to the use of the multi-dye conjugates in conjunction in an IHC assay, the skilled artisan will appreciate that the multi-dye conjugates may also be used in situ hybridization (ISH) assays, or any combination of IHC and ISH assays. The skilled artisan will also appreciate that the multi-dye conjugates may be used in both simplex assays and multiplex assays (for both IHC and ISH).

In the embodiments described herein, detection reagents or detection kits are utilized to label (e.g. with an enzyme) one or more targets in a biological sample. For example, detection kits may include a first composition comprising a specific binding moiety (e.g. an antibody conjugate) and a second composition comprising detection reagents specific to that first composition, such that a target may be labeled. In some embodiments, the detection kit includes more than one conjugates for detecting different targets, where each kit also includes detection reagents specific for each of the conjugates included within the kit.

In some embodiments, the detection reagents are specific binding moieties specific to a particular target (such as those targets enumerated further herein). In some embodiments, the specific binding moieties are primary antibodies or primary antibody conjugates. In some embodiments, the primary antibody is conjugated to a detectable label, such as a hapten. In other embodiments, the specific binding moieties are nucleic acid probes, where the nucleic acid probes are conjugated to a detectable label, such as a hapten. The detection reagents may also include secondary antibodies specific to the specific binding moieties, and which are themselves conjugated to an enzyme. Suitable enzymes include, but are not limited to, horseradish peroxidase (HRP), alkaline phosphatase (AP), acid phosphatase, glucose oxidase, β-galactosidase, β-glucuronidase or β-lactamase. In other embodiments, enzymes include oxidoreductases or peroxidases (e.g. HRP). The secondary antibodies may be anti-antibody antibodies (e.g. specific to a particular primary antibody) or anti-label antibodies (e.g. specific to a particular label conjugated to a primary antibody or a nucleic acid probe). In some embodiments, the secondary antibodies are anti-hapten antibodies. The primary antibodies, primary antibody conjugates, secondary antibodies and/or nucleic acid probes may be introduced to a sample according to procedures known to those of ordinary skill in the art to effect labeling of one or more targets in a biological sample with an enzyme and as illustrated herein.

Referring to FIG. 1, a tissue sample containing one or more targets is contacted with a first specific binding moiety specific to a first target to provide a first specific binding moiety-target complex (step 100). In some embodiments, the first specific binding moiety is a primary antibody or antibody conjugate (e.g. an unmodified antibody or an antibody conjugated to a detectable label, such as a hapten). In other embodiments, the first specific binding moiety is a nucleic acid probe (i.e. an oligonucleotide probe) conjugated to a detectable label, such as a hapten. The first specific binding moiety-target complex is subsequently labeled with a first enzyme through the first specific binding moiety (step 110). In some embodiments, the labeling of the target complex may be achieved with a secondary antibody, the secondary antibody being an anti-antibody antibody (e.g. one that is specific to a primary antibody, namely an anti-antibody antibody) or an anti-label antibody (e.g. an anti-label antibody or an anti-hapten antibody), the secondary antibody being conjugated to an enzyme (e.g. HRP, AP, etc.). The tissue sample is then contacted with a first multi-dye conjugate (step 120), the first multi-dye conjugate comprising a tissue reactive moiety and at least two detectable moieties (e.g. at least two chromogens). Upon interaction of the first enzyme with the tissue reactive moiety portion of the first multi-dye conjugate, a first detectable multi-dye complex is deposited proximal to or onto the first target. Finally, signals from the first detectable multi-dye complex are detected (e.g. brightfield microscopy) (step 130).

The aforementioned process may be repeated for any number of targets within the sample. In some embodiments, an enzyme inactivation composition may be introduced to substantially or completely inactivate any enzymes from any upstream steps. Then, the tissue sample may be contacted with a second specific binding moiety specific to a second target to provide a second specific binding moiety target complex (step 100). The second specific binding moiety target complex is subsequently labeled with a second enzyme through the second specific binding moiety (step 110). The tissue sample is then contacted with a second multi-dye conjugate (step 120), the second multi-dye conjugate comprising a tissue reactive moiety and at least two detectable moieties (e.g. at least two chromogens). In some embodiments, a sum of the wavelengths from the at least two detectable moieties of the second multi-dye conjugate is different than a sum of the wavelengths from the at least two detectable moieties of the first multi-dye conjugate. In other embodiments, the color of the second multi-dye conjugate is different than the color of the first multi-dye conjugate. Upon interaction of the second enzyme with the tissue reactive moiety portion of the second multi-dye conjugate, a second detectable multi-dye complex is deposited proximal to or onto the second target. Finally, signals from the second detectable multi-dye complex are detected (e.g. brightfield microscopy) (step 130).

The above-identified steps may be repeated for the detection of third, fourth, or nth targets within the biological sample, where each of the third, fourth, or nth multi-dye conjugates comprises a different color. The skilled artisan will also appreciate that while the above-identified steps make use of multi-dye conjugates, TSA or QMSA conjugates coupled to only a single detectable moiety may be utilized interchangeably. For example, a first target may be stained with a first TSA-conjugate having a single chromogen or a first QMSA-conjugate having a single chromogen; a second target may be stained with a multi-dye conjugate of Formula (I); and a third target may be stained with a second TSA-conjugate having a single chromogen or a second QMSA-conjugate having a single chromogen.

Advantageously, for the method just described, the first enzyme and the second enzyme are different enzymes. For example, the first enzyme can be a phosphatase or phosphodiesterase, and the second enzyme can be a peroxidase. In certain embodiments, the first enzyme is alkaline phosphatase and the second enzyme is horseradish peroxidase. Also advantageously, the first enzyme does not interact with the second multi-dye conjugate to form a second detectable multi-dye complex proximal to the first target, and likewise the second enzyme does not interact with the first multi-dye conjugate to form a first detectable multi-dye complex proximal to the second target.

The skilled artisan will appreciate that the steps illustrated in FIG. 1 may be performed sequentially (or serially) or substantially simultaneously. For example, the tissue sample may be contacted simultaneously at step 100 with two specific binding moieties (where each specific binding moiety is specific to a particular target); and then each specific binding moiety-target complex simultaneously labeled with different enzymes at step 110. In these embodiments, either the reagents used at either step 100 or 110 may be supplied as a "pool" or "cocktail" of reagents. Alternatively, a first specific binding moiety may be deposited (step 100) followed by labeling of that first specific binding moiety-target complex (step 110). Steps 100 and 110 may be serially repeated any number of times prior to the introduction of any multi-dye conjugates. Subsequently, a tissue sample having a plurality of enzyme labeled target complexes may then be contacted with a plurality of multi-dye conjugates.

Figure 2:
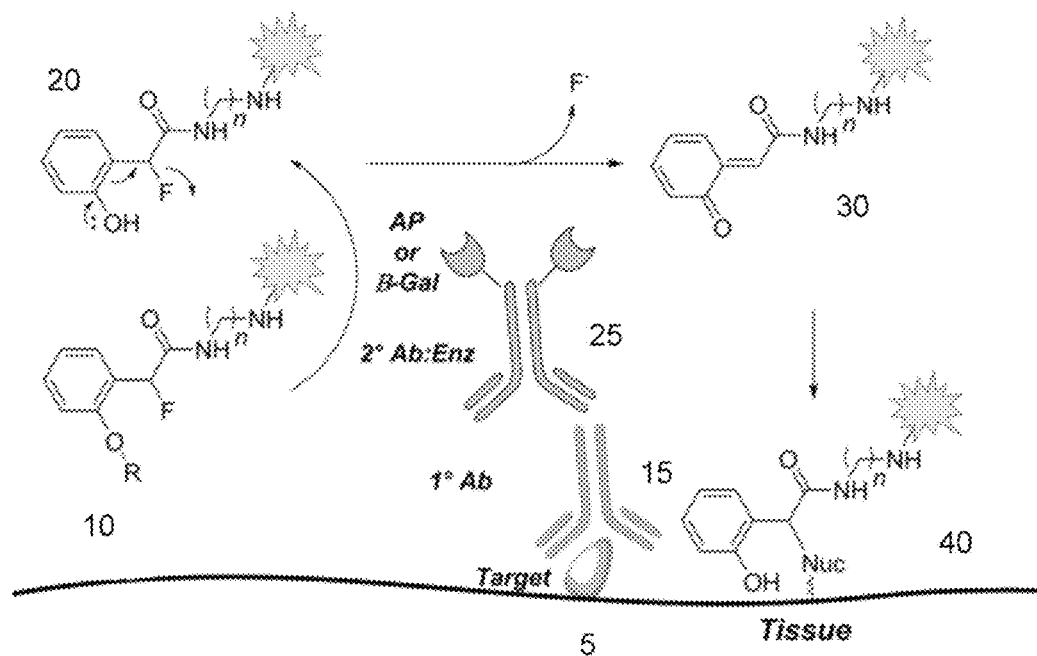
FIG. 2 illustrates the reaction between a multi-dye conjugate and an enzyme deposited on a target, the multi-dye conjugate comprising a quinone methide precursor moiety portion.

With reference to FIG. 2, a detection probe 15 is first introduced to a tissue sample having a target 5 to form a target-detection probe complex. In some embodiments, the detection probe 15 is a primary antibody. Subsequently, a labeling conjugate 25 is introduced to the tissue sample, the labeling conjugate 25 comprising at least one enzyme conjugated thereto. In the embodiment depicted, the labeling conjugate is a secondary antibody, where the secondary antibody is an anti-species antibody conjugated to an enzyme. Next, a multi-dye conjugate 10 is introduced. Upon interaction of the enzyme with the multi-dye conjugate 10, the multi-dye conjugate undergoes a structural, conformational, or electronic change 20 to form a tissue reactive intermediate 30. In this particular embodiment, the multi-dye conjugate comprises a quinone methide precursor moiety that, upon interaction with the alkaline phosphatase enzyme, causes a fluorine leaving group to be ejected, resulting in the respective quinone methide intermediate 30. The quinone methide intermediate 30 then forms a covalent bond with the tissue proximal or directly on the tissue to form a detectable multi-dye complex 40. Signals from the conjugated chromophores of the multi-dye complex 40 may then be detected according to methods known to those of ordinary skill in the art.

Figure 3:
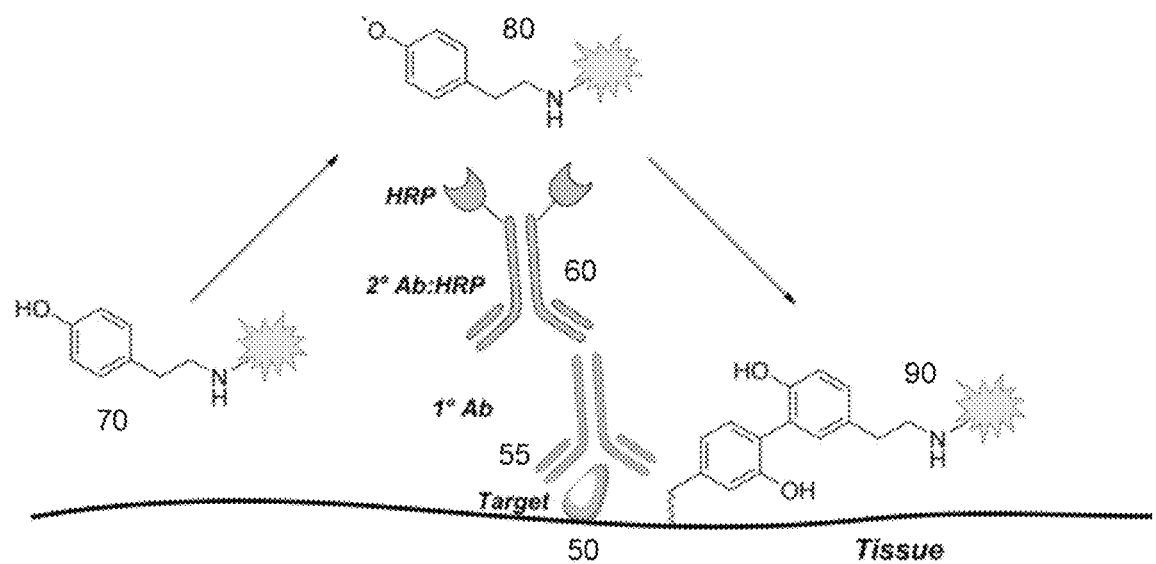
FIG. 3 illustrates the reaction between a multi-dye conjugate and an enzyme deposited on a target, the multi-dye conjugate comprising a tyramide moiety portion.

With reference to FIG. 3, a detection probe 55 is first introduced to a tissue sample having a target 50 to form a target-detection probe complex. In some embodiments, the detection probe 55 is a primary antibody. Subsequently, a labeling conjugate 60 is introduced to the tissue sample, the labeling conjugate 60 comprising at least one enzyme conjugated thereto. In the embodiment depicted, the labeling conjugate is a secondary antibody, where the secondary antibody is an anti-species antibody conjugated to an enzyme. Next, a multi-dye conjugate 70 is introduced. Upon interaction of the enzyme with the multi-dye conjugate 70, a tissue reactive intermediate 80 is formed. In this particular embodiment, the multi-dye conjugate 70 comprises a tyramide moiety that, upon interaction with horseradish peroxidase enzyme, causes formation of the radical species 80. The radical intermediate 80 then forms a covalent bond with the tissue proximal or directly on the tissue to form a detectable multi-dye complex 90. Signals from the conjugated chromophores of the multi-dye complex 90 may then be detected according to methods known to those of ordinary skill in the art.

In some embodiments, the biological samples are pre-treated with an enzyme inactivation composition to substantially or completely inactivate endogenous peroxidase activity. For example, some cells or tissues contain endogenous peroxidase. Using an HRP conjugated antibody may result in high, non-specific background staining. This non-specific background can be reduced by pre-treatment of the sample with an enzyme inactivation composition as disclosed herein. In some embodiments, the samples are pre-treated with hydrogen peroxide only (about 1% to about 3% by weight of an appropriate pre-treatment solution) to reduce endogenous peroxidase activity. Once the endogenous peroxidase activity has been reduced or inactivated, detection kits may be added, followed by inactivation of the enzymes present in the detection kits, as provided above. The disclosed enzyme inactivation composition and methods can also be used as a method to inactivate endogenous enzyme peroxidase activity.

In some embodiments if the specimen is a sample embedded in paraffin, the sample can be deparaffinized using appropriate deparaffinizing fluid(s). After a waste remover removes the deparaffinizing fluid(s), any number of substances can be successively applied to the specimen. The substances can be for pretreatment (e.g., protein-crosslinking, expose nucleic acids, etc.), denaturation, hybridization, washing (e.g., stringency wash), detection (e.g., link a visual or marker molecule to a probe), amplifying (e.g., amplifying proteins, genes, etc.), counterstaining, coverslipping, or the like.

Automation

The assays and methods of the present disclosure may be automated and may be combined with a specimen processing apparatus. The specimen processing apparatus can be an automated apparatus, such as the BENCHMARK XT instrument and DISCOVERY XT instrument sold by Ventana Medical Systems, Inc. Ventana Medical Systems, Inc. is the assignee of a number of United States patents disclosing systems and methods for performing automated analyses, including U.S. Pat. Nos. 5,650,327, 5,654,200, 6,296,809, 6,352,861, 6,827,901 and 6,943,029, and U.S. Published Patent Application Nos. 20030211630 and 20040052685, each of which is incorporated herein by reference in its entirety. Alternatively, specimens can be manually processed.

The specimen processing apparatus can apply fixatives to the specimen. Fixatives can include cross-linking agents (such as aldehydes, e.g., formaldehyde, paraformaldehyde, and glutaraldehyde, as well as non-aldehyde cross-linking agents), oxidizing agents (e.g., metallic ions and complexes, such as osmium tetroxide and chromic acid), protein-denaturing agents (e.g., acetic acid, methanol, and ethanol), fixatives of unknown mechanism (e.g., mercuric chloride, acetone, and picric acid), combination reagents (e.g., Carnoy's fixative, methacarn, Bouin's fluid, B5 fixative, Rossman's fluid, and Gendre's fluid), microwaves, and miscellaneous fixatives (e.g., excluded volume fixation and vapor fixation).

If the specimen is a sample embedded in paraffin, the sample can be deparaffinized with the specimen processing apparatus using appropriate deparaffinizing fluid(s). After the waste remover removes the deparaffinizing fluid(s), any number of substances can be successively applied to the specimen. The substances can be for pretreatment (e.g., protein-crosslinking, expose nucleic acids, etc.), denaturation, hybridization, washing (e.g., stringency wash), detection (e.g., link a visual or marker molecule to a probe), amplifying (e.g., amplifying proteins, genes, etc.), counterstaining, coverslipping, or the like.

The specimen processing apparatus can apply a wide range of substances to the specimen. The substances include, without limitation, stains, probes, reagents, rinses, and/or conditioners. The substances can be fluids (e.g., gases, liquids, or gas/liquid mixtures), or the like. The fluids can be solvents (e.g., polar solvents, non-polar solvents, etc.), solutions (e.g., aqueous solutions or other types of solutions), or the like. Reagents can include, without limitation, stains, wetting agents, antibodies (e.g., monoclonal antibodies, polyclonal antibodies, etc.), antigen recovering fluids (e.g., aqueous- or non-aqueous-based antigen retrieval solutions, antigen recovering buffers, etc.), or the like. Probes can be an isolated nucleic acid or an isolated synthetic oligonucleotide, attached to a detectable label. Labels can include radioactive isotopes, enzyme substrates, co-factors, ligands, chemiluminescent or fluorescent agents, haptens, and enzymes.

After the specimens are processed, a user can transport specimen-bearing slides to the imaging apparatus. The imaging apparatus used here is a brightfield imager slide scanner. One brightfield imager is the iScan Coreo™ brightfield scanner sold by Ventana Medical Systems, Inc. In automated embodiments, the imaging apparatus is a digital pathology device as disclosed in International Patent Application No.: PCT/US2010/002772 (Patent Publication No.: WO/2011/049608) entitled IMAGING SYSTEM AND TECHNIQUES or disclosed in U.S. Patent Application Publication No. 2014/0178169, filed on Feb. 3, 2014, entitled IMAGING SYSTEMS, CASSETTES, AND METHODS OF USING THE SAME. International Patent Application No. PCT/US2010/002772 and U.S. Patent Application Publication No. 2014/0178169 are incorporated by reference in their entities. In other embodiments, the imaging apparatus includes a digital camera coupled to a microscope.

Counterstaining

Counterstaining is a method of post-treating the samples after they have already been stained with agents to detect one or more targets, such that their structures can be more readily visualized under a microscope. For example, a counterstain is optionally used prior to coverslipping to render the immunohistochemical stain more distinct. Counterstains differ in color from a primary stain. Numerous counterstains are well known, such as hematoxylin, eosin, methyl green, methylene blue, Giemsa, Alcian blue, and Nuclear Fast Red. DAPI (4',6-diamidino-2-phenylindole) is a fluorescent stain that may be used.

In some examples, more than one stain can be mixed together to produce the counterstain. This provides flexibility and the ability to choose stains. For example, a first stain, can be selected for the mixture that has a particular attribute, but yet does not have a different desired attribute. A second stain can be added to the mixture that displays the missing desired attribute. For example, toluidine blue, DAPI, and pontamine sky blue can be mixed together to form a counterstain.

Detection and/or Imaging

Certain aspects, or all, of the disclosed embodiments can be automated, and facilitated by computer analysis and/or image analysis system. In some applications, precise color or fluorescence ratios are measured. In some embodiments, light microscopy is utilized for image analysis. Certain disclosed embodiments involve acquiring digital images. This can be done by coupling a digital camera to a microscope. Digital images obtained of stained samples are analyzed using image analysis software. Color or fluorescence can be measured in several different ways. For example, color can be measured as red, blue, and green values; hue, saturation, and intensity values; and/or by measuring a specific wavelength or range of wavelengths using a spectral imaging camera. The samples also can be evaluated qualitatively and semi-quantitatively. Qualitative assessment includes assessing the staining intensity, identifying the positively-staining cells and the intracellular compartments involved in staining, and evaluating the overall sample or slide quality. Separate evaluations are performed on the test samples and this analysis can include a comparison to known average values to determine if the samples represent an abnormal state.

Kits

In some embodiments is a kit or composition comprising (1) a multi-dye conjugate comprising a tissue reactive moiety and at least two chromophores, wherein the tissue reactive moiety is selected from the group consisting of a quinone methide precursor or a tyramide, and wherein the at least two chromophores are different; and (2) a specific binding moiety specific for a particular target. In some embodiments, the specific binding moiety is a primary antibody specific for a target. In other embodiments, the specific binding moiety is a nucleic acid probe specific for a target. In some embodiments, the kit further comprises an anti-antibody antibody (an anti-species antibody) or an anti-label antibody, where the anti-antibody antibody or the anti-label antibody is conjugated to an enzyme, and where the anti-antibody antibody or the anti-label antibody is specific for the primary antibody of the kit/composition or a label conjugated to the primary antibody or the nucleic acid probe of the kit/composition.

Of course, any kit may include other agents, including buffers; counterstaining agents; enzyme inactivation compositions; deparraffinization solutions, etc. as needed for manual or automated target detection. The kit may also include instructions for using any of the components of the kit, including methods of applying the kit components to a tissue sample to effect detection of one or more targets therein.

Samples and Targets

Samples include biological components and generally are suspected of including one or more target molecules of interest. Target molecules can be on the surface of cells and the cells can be in a suspension, or in a tissue section. Target molecules can also be intracellular and detected upon cell lysis or penetration of the cell by a probe. One of ordinary skill in the art will appreciate that the method of detecting target molecules in a sample will vary depending upon the type of sample and probe being used. Methods of collecting and preparing samples are known in the art.

Samples for use in the embodiments of the method and with the composition disclosed herein, such as a tissue or other biological sample, can be prepared using any method known in the art by of one of ordinary skill. The samples can be obtained from a subject for routine screening or from a subject that is suspected of having a disorder, such as a genetic abnormality, infection, or a neoplasia. The described embodiments of the disclosed method can also be applied to samples that do not have genetic abnormalities, diseases, disorders, etc., referred to as "normal" samples. Such normal samples are useful, among other things, as controls for comparison to other samples. The samples can be analyzed for many different purposes. For example, the samples can be used in a scientific study or for the diagnosis of a suspected malady, or as prognostic indicators for treatment success, survival, etc.

Samples can include multiple targets that can be specifically bound by a probe or reporter molecule. The targets can be nucleic acid sequences or proteins. Throughout this disclosure when reference is made to a target protein it is understood that the nucleic acid sequences associated with that protein can also be used as a target. In some examples, the target is a protein or nucleic acid molecule from a pathogen, such as a virus, bacteria, or intracellular parasite, such as from a viral genome. For example, a target protein may be produced from a target nucleic acid sequence associated with (e.g., correlated with, causally implicated in, etc.) a disease.

A target nucleic acid sequence can vary substantially in size. Without limitation, the nucleic acid sequence can have a variable number of nucleic acid residues. For example, a target nucleic acid sequence can have at least about 10 nucleic acid residues, or at least about 20, 30, 50, 100, 150, 500, 1000 residues. Similarly, a target polypeptide can vary substantially in size. Without limitation, the target polypeptide will include at least one epitope that binds to a peptide specific antibody, or fragment thereof. In some embodiments that polypeptide can include at least two epitopes that bind to a peptide specific antibody, or fragment thereof.

In specific, non-limiting examples, a target protein is produced by a target nucleic acid sequence (e.g., genomic target nucleic acid sequence) associated with a neoplasm (for example, a cancer). Numerous chromosome abnormalities (including translocations and other rearrangements, amplification or deletion) have been identified in neoplastic cells, especially in cancer cells, such as B cell and T cell leukemias, lymphomas, breast cancer, colon cancer, neurological cancers and the like. Therefore, in some examples, at least a portion of the target molecule is produced by a nucleic acid sequence (e.g., genomic target nucleic acid sequence) amplified or deleted in at least a subset of cells in a sample.

Oncogenes are known to be responsible for several human malignancies. For example, chromosomal rearrangements involving the SYT gene located in the breakpoint region of chromosome 18q11.2 are common among synovial sarcoma soft tissue tumors. The t(18q11.2) translocation can be identified, for example, using probes with different labels: the first probe includes FPC nucleic acid molecules generated from a target nucleic acid sequence that extends distally from the SYT gene, and the second probe includes FPC nucleic acid generated from a target nucleic acid sequence that extends 3' or proximal to the SYT gene. When probes corresponding to these target nucleic acid sequences (e.g., genomic target nucleic acid sequences) are used in an in situ hybridization procedure, normal cells, which lack a t(18q11.2) in the SYT gene region, exhibit two fusions (generated by the two labels in close proximity) signals, reflecting the two intact copies of SYT. Abnormal cells with a t(18q11.2) exhibit a single fusion signal.

In other examples, a target protein produced from a nucleic acid sequence (e.g., genomic target nucleic acid sequence) is selected that is a tumor suppressor gene that is deleted (lost) in malignant cells. For example, the p16 region (including D9S1749, D9S1747, p16(INK4A), p14(ARF), D9S1748, p15(INK4B), and D9S1752) located on chromosome 9p21 is deleted in certain bladder cancers. Chromosomal deletions involving the distal region of the short arm of chromosome 1 (that encompasses, for example, SHGC57243, TP73, EGFL3, ABL2, ANGPTL1, and SHGC-1322), and the pericentromeric region (e.g., 19p13-19q13) of chromosome 19 (that encompasses, for example, MAN2B1, ZNF443, ZNF44, CRX, GLTSCR2, and GLTSCR1) are characteristic molecular features of certain types of solid tumors of the central nervous system.

The aforementioned examples are provided solely for purpose of illustration and are not intended to be limiting. Numerous other cytogenetic abnormalities that correlate with neoplastic transformation and/or growth are known to those of ordinary skill in the art. Target proteins that are produced by nucleic acid sequences (e.g., genomic target nucleic acid sequences), which have been correlated with neoplastic transformation and which are useful in the disclosed methods, also include the EGFR gene (7p12; e.g., GENBANK™ Accession No. NC-000007, nucleotides 55054219-55242525), the C-MYC gene (8q24.21; e.g., GENBANK™ Accession No. NC-000008, nucleotides 128817498-128822856), D5S271 (5p15.2), lipoprotein lipase (LPL) gene (8p22; e.g., GENBANK™ Accession No. NC-000008, nucleotides 19841058-19869049), RB1 (13q14; e.g., GENBANK™ Accession No. NC-000013, nucleotides 47775912-47954023), p53 (17p13.1; e.g., GENBANK™ Accession No. NC-000017, complement, nucleotides 7512464-7531642)), N-MYC (2p24; e.g., GENBANK™ Accession No. NC-000002, complement, nucleotides 151835231-151854620), CHOP (12q13; e.g., GENBANK™ Accession No. NC-000012, complement, nucleotides 56196638-56200567), FUS (16p11.2; e.g., GENBANK™ Accession No. NC-000016, nucleotides 31098954-31110601), FKHR (13p14; e.g., GENBANK™ Accession No. NC-000013, complement, nucleotides 40027817-40138734), as well as, for example: ALK (2p23; e.g., GENBANK™ Accession No. NC-000002, complement, nucleotides 29269144-29997936), Ig heavy chain, CCND1 (11q13; e.g., GENBANK™ Accession No. NC-000011, nucleotides 69165054.69178423), BCL2 (18q21.3; e.g., GENBANK™ Accession No. NC-000018, complement, nucleotides 58941559-59137593), BCL6 (3q27; e.g., GENBANK™ Accession No. NC-000003, complement, nucleotides 188921859-188946169), MALF1, AP1 (1p32-p31; e.g., GENBANK™ Accession No. NC 000001, complement, nucleotides 59019051-59022373), TOP2A (17q21-q22; e.g., GENBANK™ Accession No. NC-000017, complement, nucleotides 35798321-35827695), TMPRSS (21q22.3; e.g., GENBANK™ Accession No. NC-000021, complement, nucleotides 41758351-41801948), ERG (21q22.3; e.g., GENBANK™ Accession No. NC-000021, complement, nucleotides 38675671-38955488); ETV1 (7p21.3; e.g., GENBANK™ Accession No. NC-000007, complement, nucleotides 13897379-13995289), EWS (22q12.2; e.g., GENBANK™ Accession No. NC-000022, nucleotides 27994271-28026505); FLI1 (11q24.1-q24.3; e.g., GENBANK™ Accession No. NC-000011, nucleotides 128069199-128187521), PAX3 (2q35-q37; e.g., GENBANK™ Accession No. NC-000002, complement, nucleotides 222772851-222871944), PAX7 (1p36.2-p36.12; e.g., GENBANK™ Accession No. NC 000001, nucleotides 18830087-18935219), PTEN (10q23.3; e.g., GENBANK™ Accession No. NC-000010, nucleotides 89613175-89716382), AKT2 (19q13.1-q13.2; e.g., GENBANK™ Accession No. NC-000019, complement, nucleotides 45431556-45483036), MYCL1 (1p34.2; e.g., GENBANK™ Accession No. NC 000001, complement, nucleotides 40133685-40140274), REL (2p13-p12; e.g., GENBANK™ Accession No. NC 000002, nucleotides 60962256-61003682) and CSF1R (5q33-q35; e.g., GENBANK™ Accession No. NC-000005, complement, nucleotides 149413051-149473128).

In other examples, a target protein is selected from a virus or other microorganism associated with a disease or condition. Detection of the virus- or microorganism-derived target nucleic acid sequence (e.g., genomic target nucleic acid sequence) in a cell or tissue sample is indicative of the presence of the organism. For example, the target peptide, polypeptide or protein can be selected from the genome of an oncogenic or pathogenic virus, a bacterium or an intracellular parasite (such as *Plasmodium falciparum* and other *Plasmodium* species, *Leishmania* (sp.), *Cryptosporidium parvum*, *Entamoeba histolytica*, and *Giardia lamblia*, as well as *Toxoplasma, Eimeria, Theileria*, and *Babesia* species).

In some examples, the target protein is produced from a nucleic acid sequence (e.g., genomic target nucleic acid sequence) from a viral genome. Exemplary viruses and corresponding genomic sequences (GENBANK™ RefSeq Accession No. in parentheses) include human adenovirus A (NC-001460), human adenovirus B (NC-004001), human adenovirus C(NC-001405), human adenovirus D (NC-002067), human adenovirus E (NC-003266), human adenovirus F (NC-001454), human astrovirus (NC-001943), human BK polyomavirus (V01109; GI:60851) human bocavirus (NC-007455), human coronavirus 229E (NC-002645), human coronavirus HKU1 (NC-006577), human coronavirus NL63 (NC-005831), human coronavirus OC43 (NC-005147), human enterovirus A (NC 001612), human enterovirus B (NC-001472), human enterovirus C(NC-001428), human enterovirus D (NC-001430), human erythrovirus V9 (NC-004295), human foamy virus (NC-001736), human herpesvirus 1 (Herpes simplex virus type 1) (NC-001806), human herpesvirus 2 (Herpes simplex virus type 2) (NC-001798), human herpesvirus 3 (Varicella zoster virus) (NC-001348), human herpesvirus 4 type 1 (Epstein-Barr virus type 1) (NC-007605), human herpesvirus 4 type 2 (Epstein-Barr virus type 2) (NC-009334), human herpesvirus 5 strain AD 169 (NC-001347), human herpesvirus 5 strain Merlin Strain (NC-006273), human herpesvirus 6A (NC-001664), human herpesvirus 6B (NC-000898), human herpesvirus 7 (NC-001716), human herpesvirus 8 type M (NC-003409), human herpesvirus 8 type P (NC-009333), human immunodeficiency virus 1 (NC-001802), human immunodeficiency virus 2 (NC-001722), human metapneumovirus (NC-004148), human papillomavirus-1 (NC-001356), human papillomavirus-18 (NC-001357), human papillomavirus-2 (NC-001352), human papillomavirus-54 (NC-001676), human papillomavirus-61 (NC-001694), human papillomavirus-cand90 (NC-004104), human papillomavirus RTRX7 (NC-004761), human papillomavirus type 10 (NC-001576), human papillomavirus type 101 (NC-008189), human papillomavirus type 103 (NC-008188), human papillomavirus type 107 (NC-009239), human papillomavirus type 16 (NC-001526), human papillomavirus type 24 (NC-001683), human papillomavirus type 26 (NC-001583), human papillomavirus type 32 (NC-001586), human papillomavirus type 34 (NC-001587), human papillomavirus type 4 (NC-001457), human papillomavirus type 41 (NC-001354), human papillomavirus type 48 (NC-001690), human papillomavirus type 49 (NC-001591), human papillomavirus type 5 (NC-001531), human papillomavirus type 50 (NC-001691), human papillomavirus type 53 (NC-001593), human papillomavirus type 60 (NC-001693), human papillomavirus type 63 (NC-001458), human papillomavirus type 6b (NC-001355), human papillomavirus type 7 (NC-001595), human papillomavirus type 71 (NC-002644), human papillomavirus type 9 (NC-001596), human papillomavirus type 92 (NC-004500), human papillomavirus type 96 (NC-005134), human parainfluenza virus 1 (NC-003461), human parainfluenza virus 2 (NC-003443), human parainfluenza virus 3 (NC-001796), human parechovirus (NC-001897), human parvovirus 4 (NC-007018), human parvovirus B19 (NC-000883), human respiratory syncytial virus (NC-001781), human rhinovirus A (NC-001617), human rhinovirus B (NC-001490), human spumaretrovirus (NC-001795), human T-lymphotropic virus 1 (NC-001436), human T-lymphotropic virus 2 (NC-001488).

In certain examples, the target protein is produced from a nucleic acid sequence (e.g., genomic target nucleic acid sequence) from an oncogenic virus, such as Epstein-Barr Virus (EBV) or a Human Papilloma Virus (HPV, e.g., HPV16, HPV18). In other examples, the target protein produced from a nucleic acid sequence (e.g., genomic target nucleic acid sequence) is from a pathogenic virus, such as a Respiratory Syncytial Virus, a Hepatitis Virus (e.g., Hepatitis C Virus), a Coronavirus (e.g., SARS virus), an Adenovirus, a Polyomavirus, a Cytomegalovirus (CMV), or a Herpes Simplex Virus (HSV).

EXAMPLES

The palette of chromogens accessible by using dual dye conjugates is believed to facilitate high contrast multiplex assays. In some embodiments, the generated colors are easily distinguishable from each other and the counterstain. These dual dye chromogens can be applied in multiplex IHC assays such as: PD-L1/CD8, PD1/CD8, CD3/CD8, CD4/CD8, PD-L1/CD8/FoxP3 (immune profiling across multiple tissue types); TTF1 & P40 (stratification of squamous and adenocarcinomas in lung); E-Cadherin & P-120 (identifying lobular versus ductal lesions in breast); and P540s/high molecular weight cytokeratin (identification of adenocarcinoma & normal glands in prostate). The dual dye chromogens can be applied in multiplex ISH assays for the identification of gene fusions, deletions and/or translocations (via break-apart or split signal ISH assays). Examples include ALK, ROS1, RET rearrangements in lung; TMPRSS2-ERG fusion in lung; and BCL2 translocation in lymphoma.

Example 1—Quinone Methide-TAMRA-Dabsyl Multi-Dye Conjugate

The Quinone Methide-TAMRA-Dabsyl Multi-Dye Conjugate comprises two chromophores, namely a TAMRA chromophore and a Dabsyl chromophore. While TAMRA alone produces a magenta color and Dabsyl alone produces a yellow color, the multi-dye conjugate produces a red color.

Figure 4:
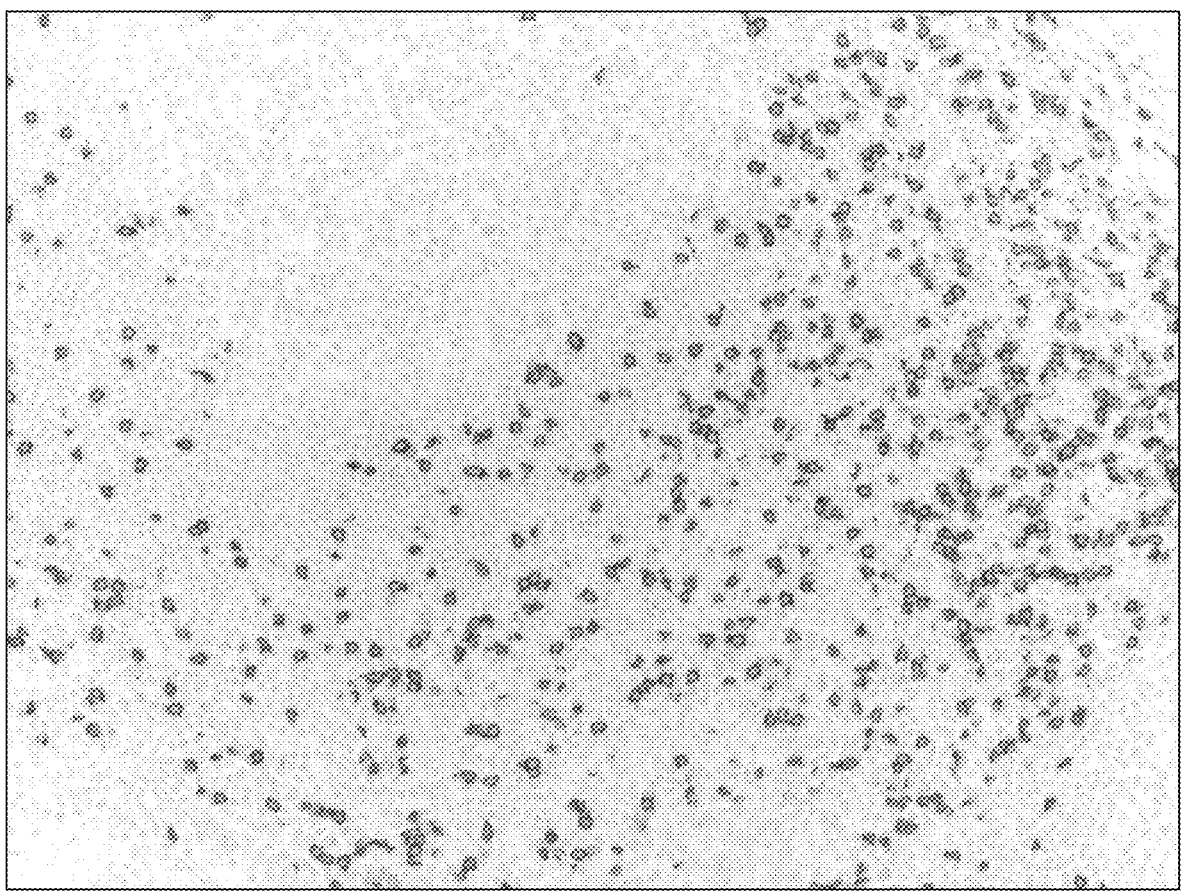
FIG. 4 illustrates a tissue sample stained with a Quinone Methide-TAMRA-Dabsyl Multi-Dye Conjugate, where the CD8 target is stained red (visible as black and dark grey areas in the black and white drawing).

The Quinone Methide-TAMRA-Dabsyl Multi-Dye Conjugate was used in an assay to stain the CD8 marker in tonsil tissue. The tissue was first deparaffinized and antigen retrieved (Cell Conditioning 1, CC1, VMSI #950-124) for about 64 minutes. Then rabbit-anti-Ki-67 antibody was applied and incubated (37° C., about 16 minutes). Subsequent washes were followed by incubation with a secondary goat polyclonal anti-rabbit, alkaline phosphatase conjugate (37° C.; about 12 minutes). After incubation with the AP conjugate the slides were washed with saline sodium citrate buffer (SSC, VMSI #950-110). Co-incubation of 200 μL of a 0.5 M tris solution (pH 10.0) and 100 μL of a 100 to 500 μM Quinone Methide-TAMRA-Dabsyl Multi-Dye Conjugate dissolved in 10 mM glycine buffer (pH 2.0) proceeded for about 32 minutes. The stained tissue sections were counterstained with modified Mayer's hematoxylin (37° C.; about 4 minutes) and then incubated with Bluing Reagent (37° C.; about 4 minutes). The slides were then dehydrated through a graded ethanol series, cleared with xylene, and manually cover-slipped. As illustrated in FIG. 4, the Quinone Methide-TAMRA-Dabsyl Multi-Dye Conjugate stained the CD8 target red.

The Quinone Methide-TAMRA-Dabsyl Multi-Dye Conjugate of this example comprised a quinone methide precursor moiety coupled to the two chromogens. Here, the two chromogens were provided in a linear arrangement, namely TAMRA served as a scaffold to couple the Dabsyl to the conjugate. The Quinone Methide-TAMRA-Dabsyl Multi-Dye Conjugate was formed by the method which follows (the numbering of intermediates is illustrated in Scheme 1):

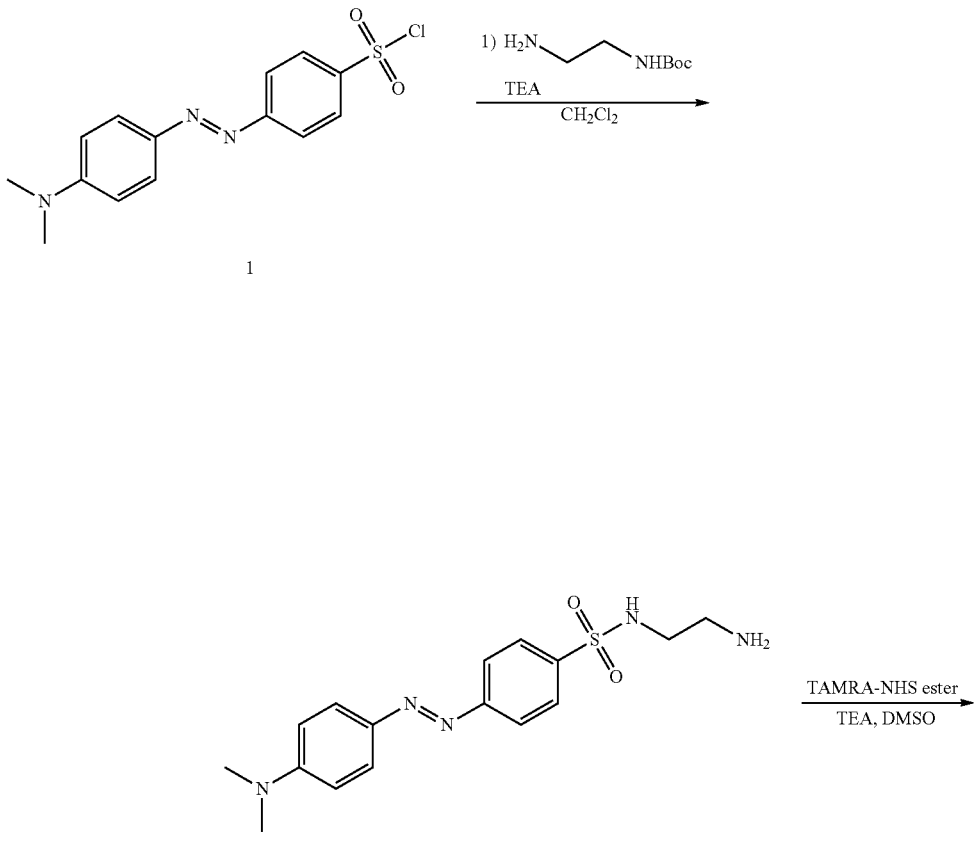

Scheme 1-Synthesis of Quinone Methide-TAMRA-Dabsyl Multi-Dye Conjugate

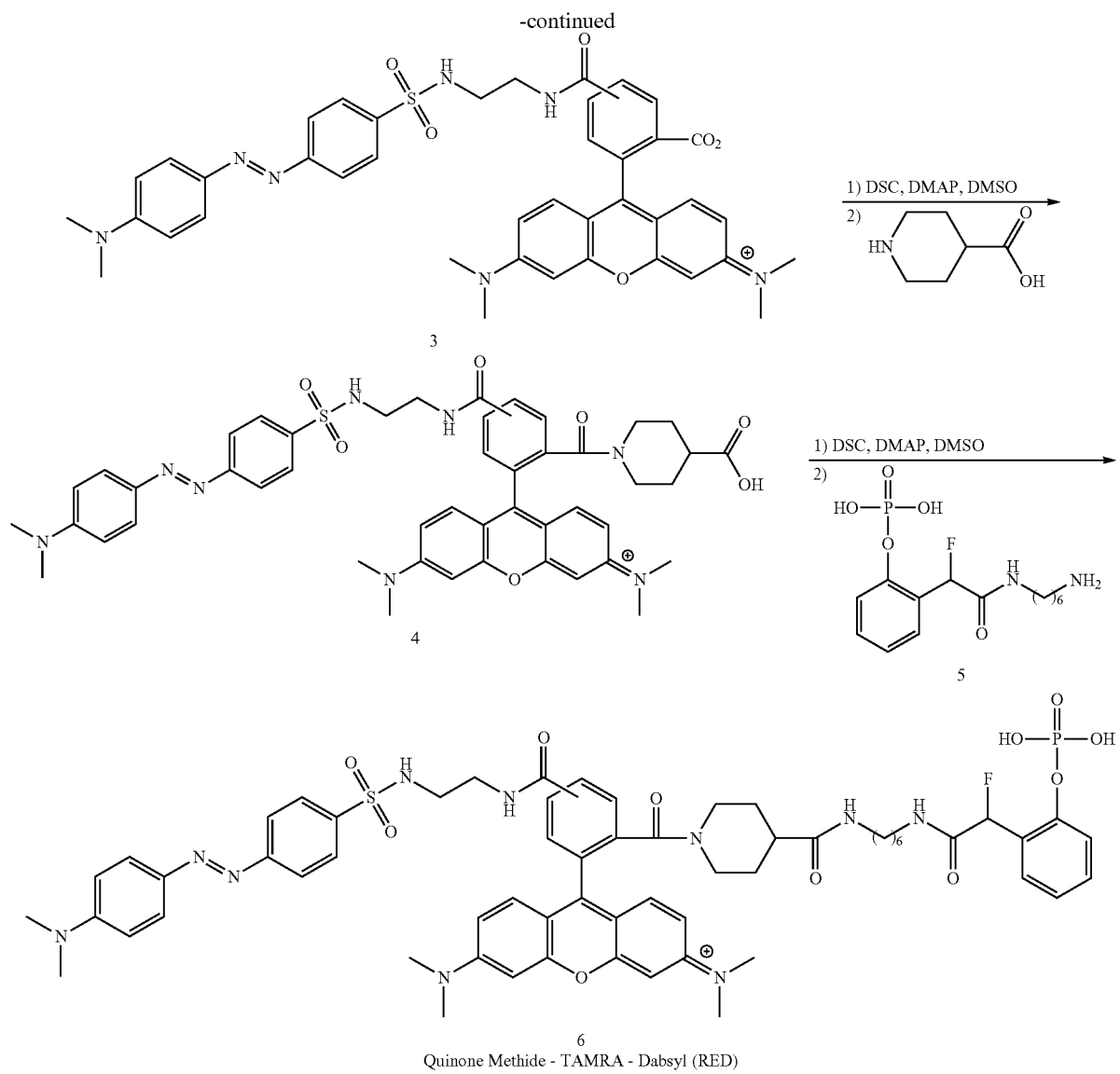

6
Quinone Methide - TAMRA - Dabsyl (RED)

To a stirred solution of N-boc-ethylenediamine (49 mg, 0.46 mmol) and triethylamine (47 mg, 0.46 mmol) in dry $CH_2Cl_2$ (5 mL) was added dabsyl chloride 1 (100 mg, 0.31 mmol). The reaction mixture was stirred at rt for 2 h, at which point the reaction appeared complete by HPLC. The solvents were removed under reduced pressure, and the resulting viscous oil was azeotroped with toluene (3×5 mL). A 1:1 mixture of $TFA:CH_2Cl_2$ (5 mL) was added, and the reaction mixture was stirred at rt for 1 h, followed by removal of solvents under reduced pressure. The resulting viscous oil was azeotroped with toluene (3×5 mL). Then, the resulting viscous oil, comprising intermediate 2, was dissolved in DMSO (3 mL) and triethylamine (49 mg, 0.46 mmol) was added. TAMRA-NHS ester (179 mg, 0.34 mmol) was then added, and the resulting mixture stirred at room temperature for about 2 h. The reaction mixture was diluted with MeOH (2 mL) and the mixture directly purified by prep HPLC (C18, 40 mL/min, 0.05% TFA in $H_2O:ACN$ 95:5 to 5:95 over about 40 min) to give the dabsyl-TAMRA conjugate 3 as a red solid (145 mg, 62% yield). MS (ESI) m/z $(M+H)^+$ calculated for $C_{41}H_{42}N_7O_6S^+$ 760.3, found 760.1.

Conjugate 3 (145 mg, 0.19 mmol) was dissolved in DMSO (3 mL), followed by addition of DMAP (23 mg, 0.19 mmol) and DSC (49 mg, 0.19 mmol). The reaction mixture was stirred at rt for 1 h, followed by a second addition of DMAP (23 mg, 0.19 mmol) and DSC (49 mg, 0.19 mmol). The reaction mixture was stirred at rt for 1 h, followed by a third addition of DMAP (23 mg, 0.19 mmol) and DSC (49 mg, 0.19 mmol). The reaction mixture was stirred at rt for 1 h, followed by addition of 4-piperidinecarboxylic acid (123 mg, 0.96 mmol) and triethylamine (97 mg, 0.96 mmol). The reaction mixture was stirred at rt for 1 h, followed by dilution with MeOH (2 mL) and direct purification by prep HPLC (C18, 40 mL/min, 0.05% TFA in $H_2O:ACN$ 95:5 to 5:95 over 40 min) to give the dabsyl-TAMRA conjugate 4 as a red solid (90 mg, 54% yield). MS (ESI) m/z $(M+H)^+$ calcd for $C_{47}H_{51}N_8O_7S^+$ 871.4, found 871.2.

Compound 4 (90 mg, 0.10 mmol) was dissolved in DMSO (3 mL), followed by addition of DMAP (13 mg, 0.10 mmol) and DSC (29 mg, 0.11 mmol). The reaction mixture was stirred at rt for 1 h, followed by addition of compound 5 (39 mg, 0.11 mmol) and triethylamine (31 mg, 0.31 mmol). The reaction mixture was stirred at rt for 1 h, followed by dilution with MeOH (2 mL) and direct purification by prep HPLC (C18, 40 mL/min, 0.05% TFA in H$_2$O:ACN 95:5 to 5:95 over 40 min) to give the dabsyl-TAMRA conjugate 6 as a red solid (85 mg, 69% yield). MS (ESI) m/z (M+2H)$^{2+}$ calculated for $C_{61}H_{71}FN_{10}O_{11}PS^{2+}$ 601.3, found 601.0.

Example 2—Tyramide-TAMRA-Cy5 Multi-Dye Conjugate

The Tyramide-TAMRA-Cy5 Multi-Dye conjugate comprises two chromophores, namely a TAMRA chromophore and a Cy5 chromophore. While TAMRA alone produces a magenta color and Cy5 alone produces a cyan color, the multi-dye conjugate produces a violet color.

Figure 5:
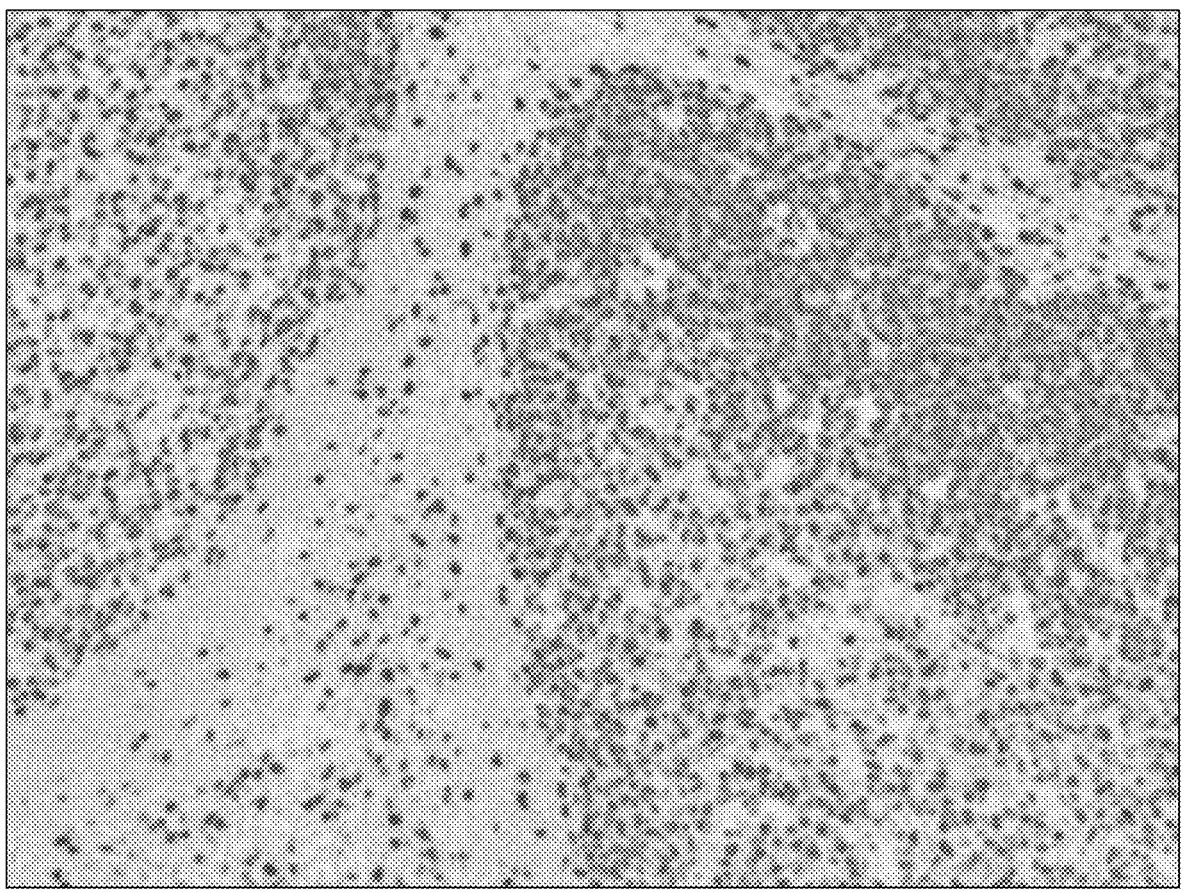
FIG. 5 illustrates a tissue sample stained with a Tyramide-TAMRA-Cy5 Multi-Dye Conjugate, where the CD8 target is stained violet (visible as dark grey spots in the black and white drawing).

The Tyramide-TAMRA-Cy5 Multi-Dye Conjugate was used in an assay to stain the Ki67 marker in tonsil tissue. The tissue was first deparaffinized and antigen retrieved with CC1 for 64 minutes. Endogenous peroxidases were inactivated by incubation with a 1% H$_2$O$_2$ solution for 4 minutes. Rabbit-anti-Ki-67 antibody was applied and incubated (37° C., 16 minutes). Subsequent washes were followed by incubation with a secondary goat polyclonal anti-rabbit, horse radish peroxidase conjugate (37° C.; 8 minutes). After incubation with the HRP conjugate, 200 µL of an about 0.1 to about 1 mM solution of Tyramide-TAMRA-Cy5 Multi-Dye Conjugate and 100 µL 0.1% H$_2$O$_2$ solution were co-incubated for about 32 minutes. The stained tissue sections were counterstained with modified Mayer's hematoxylin (37° C.; about 4 minutes) and then incubated with Bluing Reagent (37° C.; about 4 minutes). The slides were then dehydrated through a graded ethanol series, cleared with xylene, and manually cover-slipped. As illustrated in FIG. 5, the Tyramide-TAMRA-Cy5 Multi-Dye Conjugate stained the CD8 target violet.

The Tyramide-TAMRA-Cy5 Multi-Dye Conjugate of this example comprised a tyramide moiety coupled to the two chromogens. Here, the two chromogens were provided in a "branched" arrangement, using a linker, here lysine, was used to couple the two chromogens to the tyramide moiety. The Tyramide-TAMRA-Cy5 Multi-Dye Conjugate was formed by the method which follows (any numbering of intermediates is illustrated in Scheme 2):

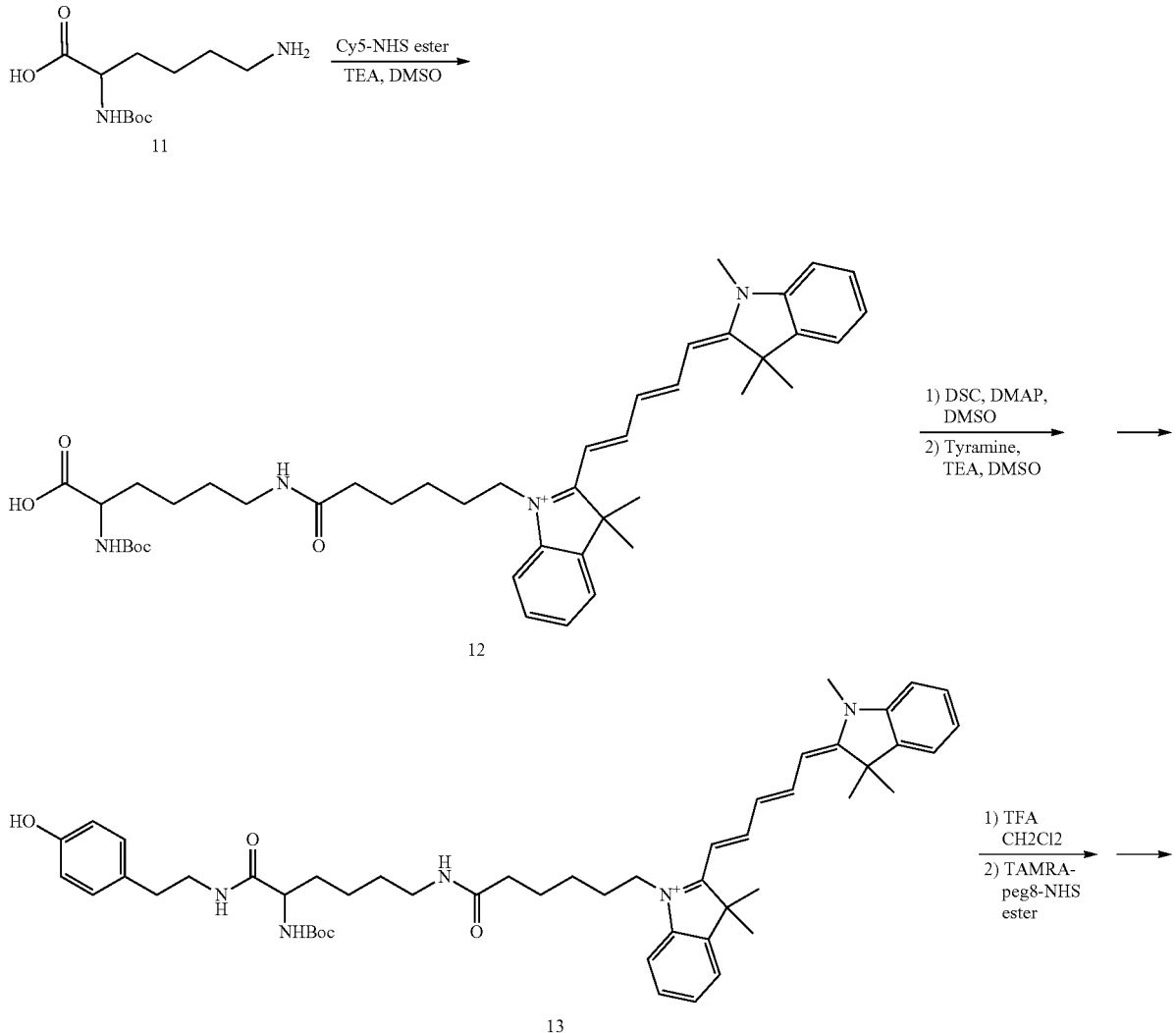

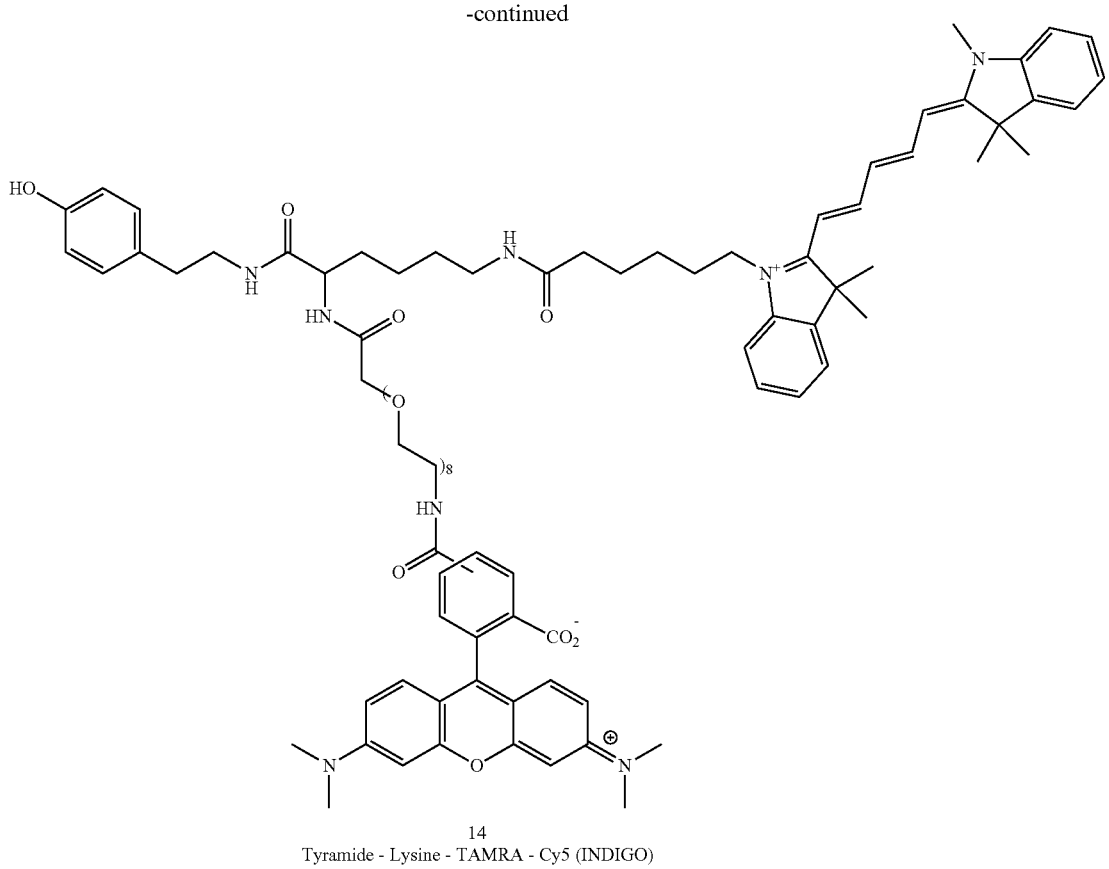

14
Tyramide - Lysine - TAMRA - Cy5 (INDIGO)

To a solution of $N_a$-boc-L-lysine (20 mg, 0.081 mmol) in DMSO (3 mL) was added trimethylamine (25 mg, 0.24 mmol) and Cy5-NHS ester (50 mg, 0.081 mmol). The reaction mixture (comprising intermediate 12) was stirred at rt for 1 h, followed by addition DMAP (10 mg, 0.081 mmol) and DSC (23 mg, 0.089 mmol). The reaction mixture was stirred at rt for 1 h, followed by addition of tyramine (17 mg, 0.12 mmol). The reaction mixture was stirred at rt for 1 h, followed by dilution with MeOH (2 mL) and direct purification by prep HPLC (C18, 40 mL/min, 0.05% TFA in $H_2O$:ACN 95:5 to 5:95 over 40 min) to give the compound 13 as a dark blue solid (37 mg, 65% yield). MS (ESI) m/z $(M)^+$ calcd for $C_{43}H_{59}N_4O_5^+$ 711.5, found 711.3.

Compound 13 (37 mg, 0.052 mmol) was dissolved in a 4:1 solution of TFA:$CH_2Cl_2$ (2 mL) and the reaction mixture stirred at rt for 1 h. The solvents were removed under reduced pressure, and the resulting dark blue viscous oil was azeotroped with toluene (3×5 mL). In a separate flask, amino-pegs-carboxylic acid (25 mg, 0.057 mmol) was dissolved in DMSO (3 mL) followed by addition of triethylamine (17 mg, 0.17 mmol). Then, TAMRA-NHS ester (30 mg, 0.057 mmol) was added and the reaction mixture was stirred at rt for 1 h. DMAP (7.0 mg, 0.057 mmol) and DSC (16 mg, 0.063 mmol) were then added, and the reaction mixture stirred at rt for 1 h. The reaction mixture was added to the previous flask containing the N-boc-cleaved compound 13 followed by addition of triethylamine (17 mg, 0.17 mmol). The resulting reaction mixture was stirred at rt for 2 h, followed by dilution with MeOH (2 mL) and direct purification by prep HPLC (C18, 40 mL/min, 0.05% TFA in $H_2O$:ACN 95:5 to 5:95 over 40 min) to give the TAMRA-Cy5 conjugate 14 a purple solid (TFA salt, 35 mg, 40% yield). MS (ESI) m/z $(M+H)^{2+}$ calcd for $C_{90}H_{118}N_8O_{16}^{2+}$ 783.5, found 783.3.

Example 3—Tyramide-TAMRA-FITC Multi-Dye Conjugate

The Tyramide-TAMRA-FITC Multi-Dye Conjugate comprises two chromophores, namely a TAMRA chromophore and a FITC chromophore. While TAMRA alone produces a magenta color and FITC alone produces a yellow color, the multi-dye conjugate produces a red color.

Figure 6:
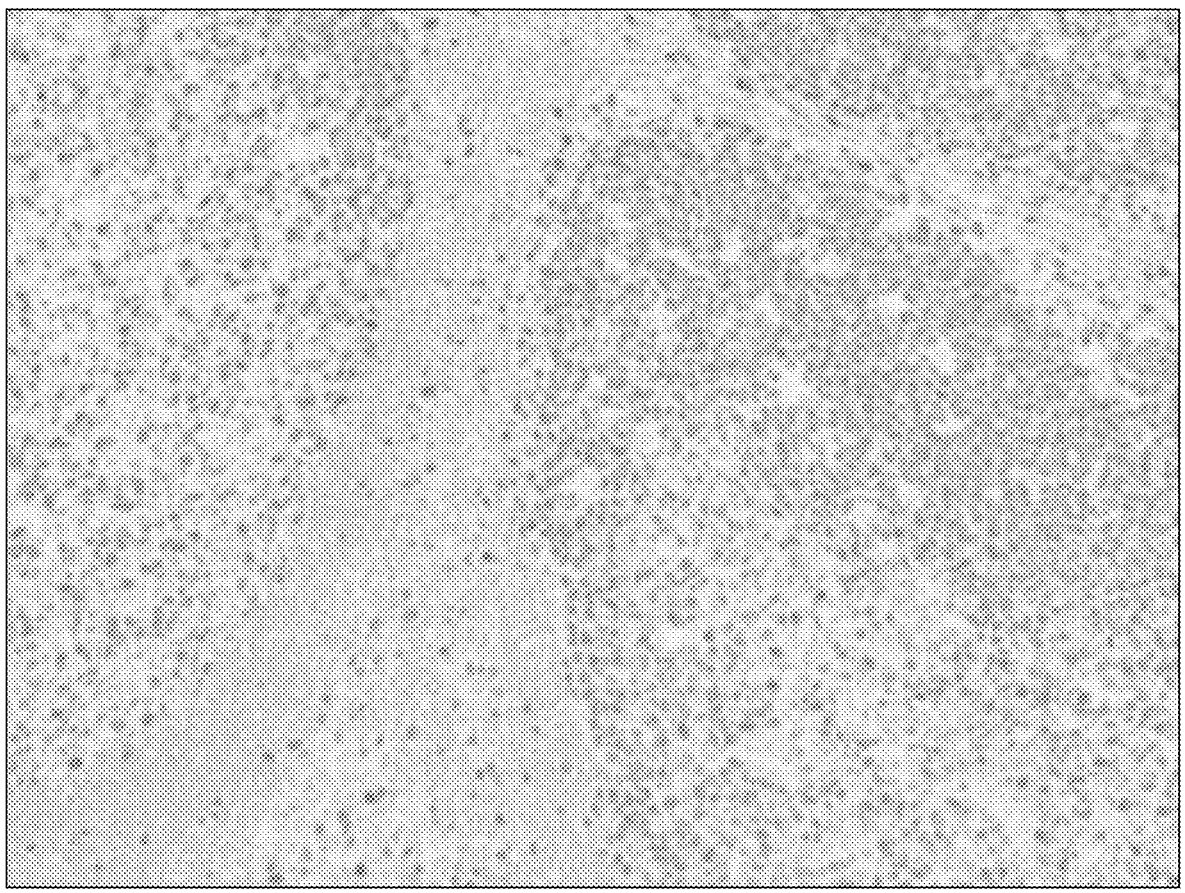
FIG. 6 illustrates a tissue sample stained with a Tyramide-TAMRA-FITC Multi-Dye Conjugate, where the CD8 target is stained red (visible as grey and dark grey spots in the black and white drawing).

The Tyramide-TAMRA-FITC Multi-Dye Conjugate was used in an assay to stain the Ki67 marker in tonsil tissue as described in Example 2. A primary antibody specific to Ki67 was first introduced to the tonsil tissue sample to form an antibody-target complex. A secondary antibody was then introduced, namely an anti-Ki67 antibody conjugated to a horseradish peroxidase enzyme. Upon introduction of the Tyramide-TAMRA-FITC Multi-Dye Conjugate, the horseradish peroxidase converted the Tyramide-TAMRA-FITC Multi-Dye Conjugate to a reactive intermediate which was then able to bond to tissue, either proximal to or directly on the labeled Ki67 target. As illustrated in FIG. 6, the Tyramide-TAMRA-FITC Multi-Dye Conjugate stained the CD8 target red.

The Tyramide-TAMRA-FITC Multi-Dye Conjugate of this example comprised the a tyramide moiety coupled to the two chromogens. Here, the two chromogens were provided in a "branched" arrangement, using a linker, here lysine, was used to couple the two chromogens to the tyramide moiety.

The Tyramide-TAMRA-FITC Multi-Dye Conjugate was prepared using an analogous procedure to the Tyramide TAMRA-Cy5 dual-dye conjugate, with Cy5 being substituted for FITC. MS (ESI) m/z (M+H)2+ calculated for $C_{79}H_{93}N_7O_2OS_2+$ 745.3, found 744.9.

Example 4—Quinone Methide-Dabcyl-Cy3 Multi-Dye Conjugate

The Quinone Methide-Dabcyl-Cy3 Multi-Dye Conjugate comprises two chromophores, namely a Dabcyl chromophore and a Cy3 chromophore. While Dabcyl alone produces a yellow color and Cy3 alone produces a magenta color, the multi-dye conjugate produces a red color.

Figure 7:
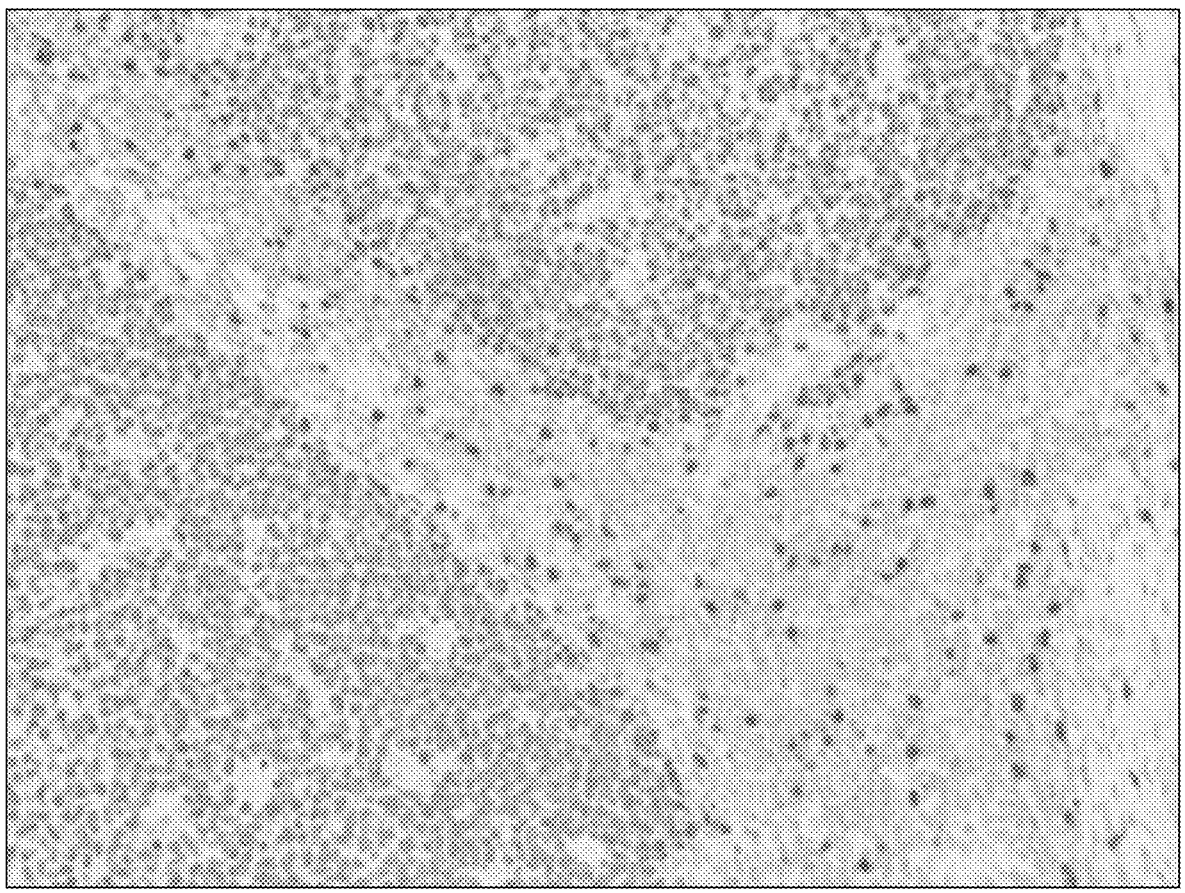
FIG. 7 illustrates a tissue sample stained with a Quinone Methide-Dabcyl-Cy3 Multi-Dye Conjugate, where the Ki-67 target is stained red (visible as dark grey spots in the black and white drawing).

The Quinone Methide-Dabcyl-Cy3 Multi-Dye Conjugate was used in an assay to stain the Ki67 marker in tonsil tissue as described in Example 1. A primary antibody specific to Ki67 was first introduced to the tonsil tissue sample to form an antibody-target complex. A secondary antibody was then introduced, namely an anti-Ki67 antibody conjugated to an alkaline phosphatase enzyme. Upon introduction of the Quinone Methide-Dabcyl-Cy3 Multi-Dye Conjugate, the alkaline phosphatase converted the Quinone Methide-Dabcyl-Cy3 Multi-Dye Conjugate to a reactive intermediate which was then able to bond to tissue, either proximal to or directly on the labeled Ki-67 target. As illustrated in FIG. 7, the Quinone Methide-Dabcyl-Cy3 Multi-Dye Conjugate stained the Ki-67 target red.

The Quinone Methide-Dabcyl-Cy3 Multi-Dye Conjugate of this example comprised a quinone methide precursor moiety coupled to the two chromogens. Here, the two chromogens were provided in a "branched" arrangement, using a linker, here lysine, was used to couple the two chromogens to the tyramide moiety. The Quinone Methide-Dabcyl-Cy3 Multi-Dye Conjugate was formed by a process similar to that described in Example 5, which follows.

Example 5—Quinone Methide-TAMRA-Dabcyl Multi-Dye Conjugate (IHC)

The Quinone Methide-Dabcyl-Cy3 Multi-Dye Conjugate comprises two chromophores, namely a TAMRA chromophore and a Dabcyl chromophore. While TAMRA alone produces a magenta color and Dabcyl alone produces a yellow color, the multi-dye conjugate produces a red color.

Figure 8:
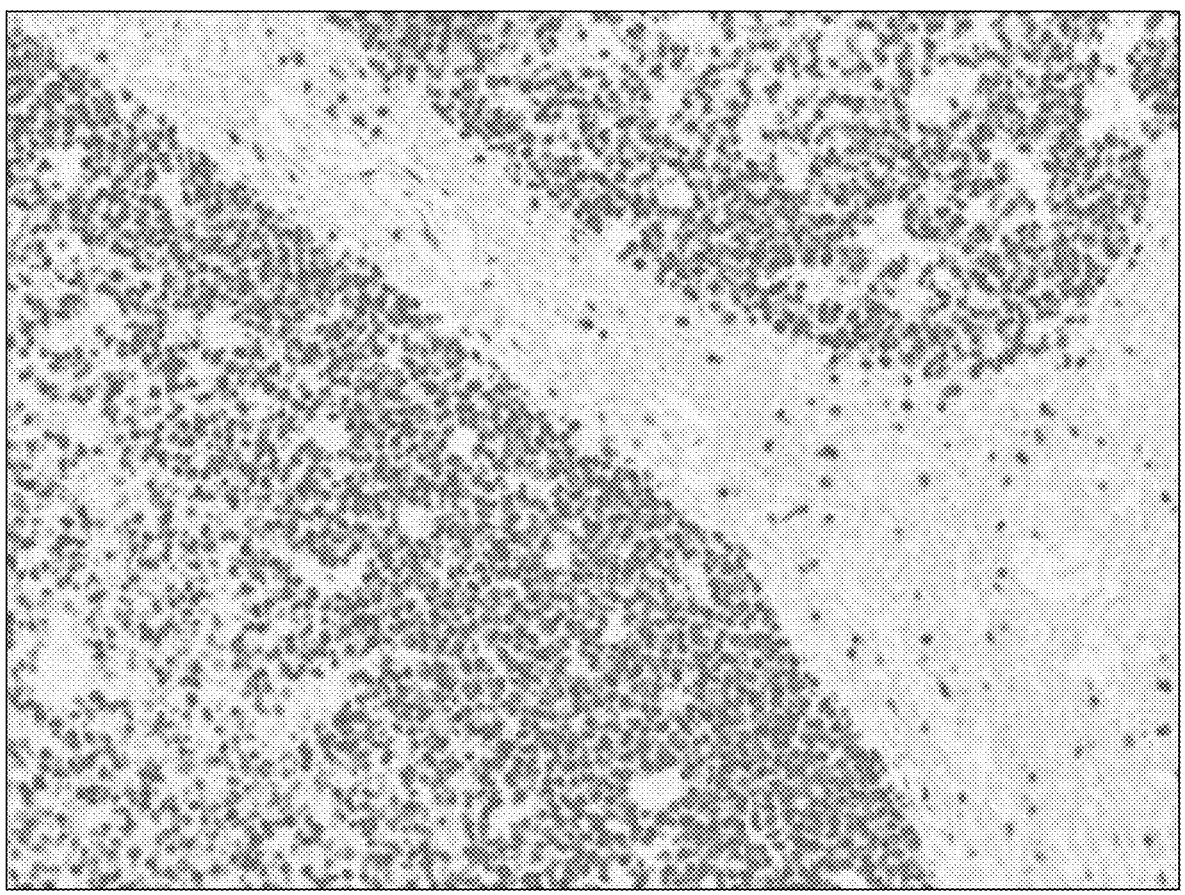
FIG. 8 illustrates a tissue sample stained with a Quinone Methide-TAMRA-Dabcyl Multi-Dye Conjugate, where the Ki-67 target is stained red (visible as dark grey and black spots in the black and white drawing).

The Quinone Methide-TAMRA-Dabcyl Multi-Dye Conjugate was used in an assay to stain the Ki67 marker in tonsil tissue as described in Example 1. A primary antibody specific to Ki67 was first introduced to the tonsil tissue sample to form an antibody-target complex. A secondary antibody was then introduced, namely an anti-Ki67 antibody conjugated to an alkaline phosphatase enzyme. Upon introduction of the Quinone Methide-TAMRA-Dabcyl Multi-Dye Conjugate, the alkaline phosphatase converted the Quinone Methide-TAMRA-Dabcyl Multi-Dye Conjugate to a reactive intermediate which was then able to bond to tissue, either proximal to or directly on the labeled Ki-67 target. As illustrated in FIG. 8, the Quinone Methide-TAMRA-Dabcyl Multi-Dye Conjugate stained the Ki-67 target red.

The Quinone Methide-TAMRA-Dabcyl Multi-Dye Conjugate of this example comprised the quinone methide precursor moiety coupled to the two chromogens. Here, the two chromogens were provided in a "branched" arrangement, using a linker, here lysine, was used to couple the two chromogens to the tyramide moiety. The Quinone Methide-TAMRA-Dabcyl Multi-Dye Conjugate was formed by the method which follows (any numbering of intermediates is illustrated in the schematic):

Scheme 3-Synthesis of Quinone Methide-TAMRA-Dabcyl Multi-Dye Conjugate

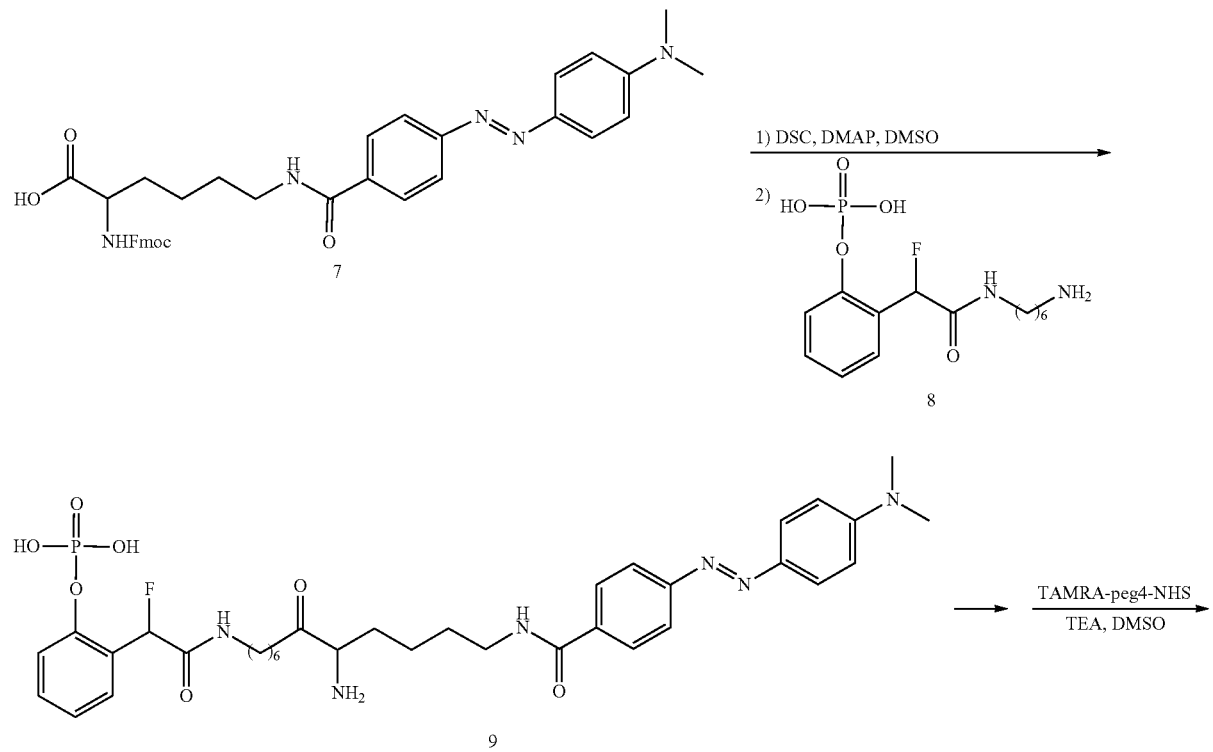

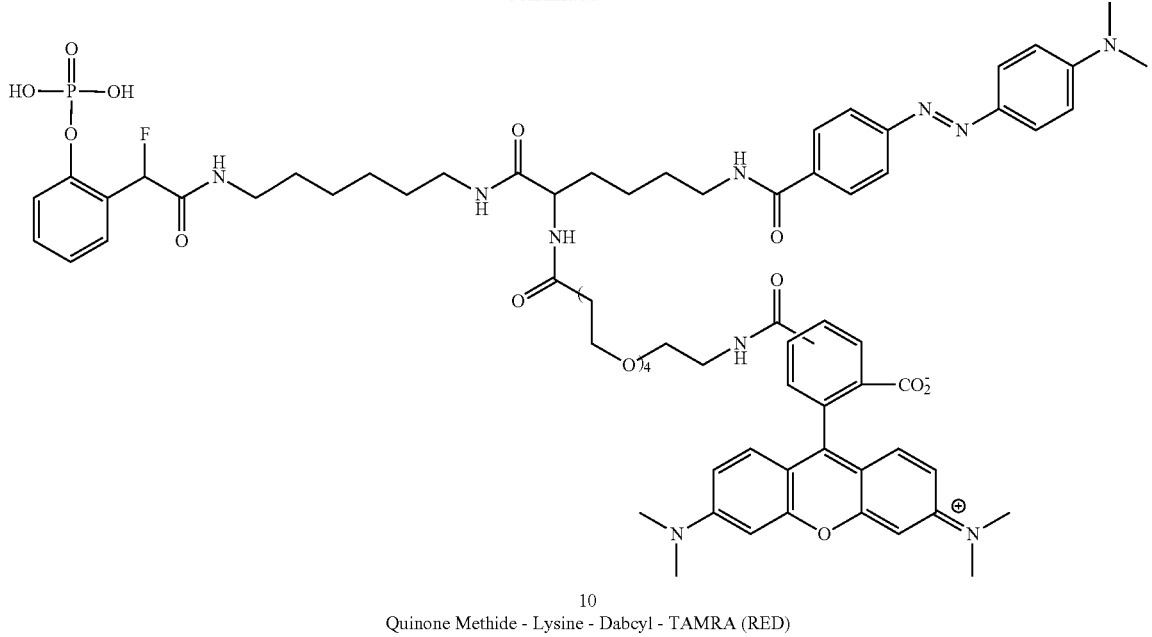

10
Quinone Methide - Lysine - Dabcyl - TAMRA (RED)

To a solution of N-Fmoc-N-dabcyl-L-lysine 7 (100 mg, 0.16 mmol) in DSMO (5 mL) was added DMAP (20 mg, 0.16 mmol) and DSC (0.18 mmol, 45 mg). Compound 8 (62 mg, 0.18 mmol) and triethylamine (49 mg, 0.48 mmol) were then added and the reaction mixture was stirred at rt for 1 h, at which point the coupling reaction appeared complete by HPLC. An additional quantity of triethylamine (3 mL) was then added, and the reaction mixture stirred vigorously at rt for 6 h, at which point the Fmoc group was cleaved as shown by HPLC. The reaction mixture was then precipitated into vigorously stirring EtOAc (100 mL). The resulting orange solid was collected by vacuum filtration and washed several times with EtOAc, giving compound 9 as an orange solid (bis-triethylamine salt, 140 mg, 93% yield). MS (ESI) m/z $(M+H)^+$ calcd for $C_{35}H_{48}FN_7O_7P^+$ 728.3, found 728.0.

In a separate flask, amino-PEG$_4$-carboxylic acid (40 mg, 0.15 mmol) was dissolved in DMSO (3 mL) followed by addition of trimethylamine (46 mg, 0.45 mmol). Then, TAMRA-NHS ester (79 mg, 0.15 mmol) was added and the reaction mixture was stirred at rt for 1 h. DMAP (18 mg, 0.15 mmol) and DSC (42 mg, 0.17 mmol) were then added, and the reaction mixture stirred at rt for 1 h. Compound 9 (140 mg, 0.15 mmol) and triethylamine were then added and the reaction mixture was stirred at rt for 2 h, followed by dilution with MeOH (2 mL) and direct purification by prep HPLC (C18, 40 mL/min, 0.05% TFA in H$_2$O:ACN 95:5 to 5:95 over 40 min) to give the dabcyl-TAMRA conjugate 10 as a red solid (mg, 54% yield). MS (ESI) m/z $(M+2H)^{2+}$ calcd for $C_{71}H_{89}FN_{10}O_{16}P^{2+}$ 694.3, found 694.0.

Example 6—Quinone Methide-TAMRA-Dabcyl Multi-Dye Conjugate (ISH)

The Quinone Methide-Dabcyl-Cy3 Multi-Dye Conjugate comprises two chromophores, namely a TAMRA chromophore and a Dabcyl chromophore. While TAMRA alone produces a magenta color and Dabcyl alone produces a yellow color, the multi-dye conjugate produces a red color.

Figure 9:
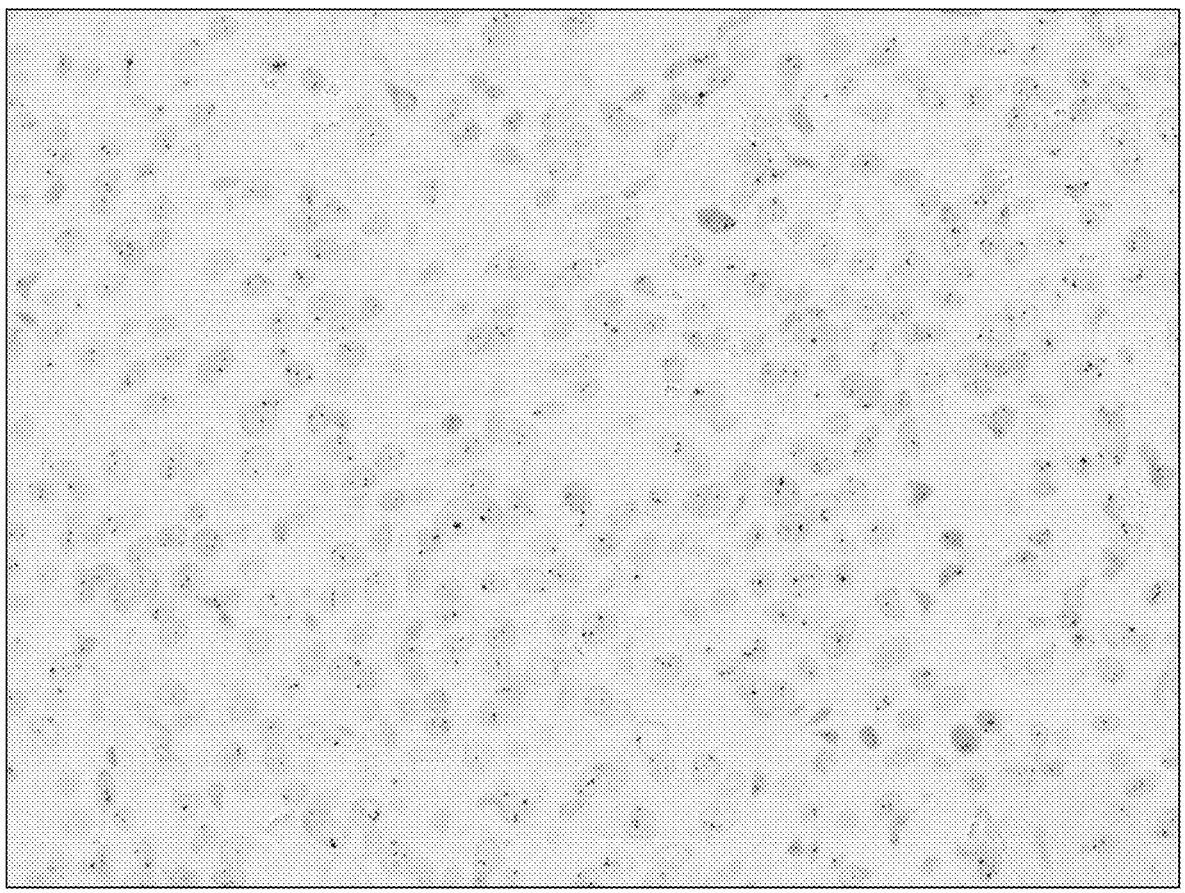
FIG. 9 illustrates a tissue sample stained with a Quinone Methide-TAMRA-Dabcyl Multi-Dye Conjugate, where the Chromosome 17 target is stained red (visible as black dots in the black and white drawing).

The Quinone Methide-TAMRA-Dabcyl Multi-Dye Conjugate was used in a multiplex ISH assay to stain Chromosome 17 marker along with silver staining for the HER2 gene in breast tissue. The tissue was deparaffinized followed by pretreatment with Cell Conditioning 2 (CC2, VMSI #950-123, 90° C.; 28 minutes) and treatment with Protease 3 (VMSI #780-4149, 37° C.; 20 minutes). A cocktail of DNP labeled Her2 and DIG labeled Chromosome 17 probes (VMSI #780-4422) were applied to the tissue, denatured (80° C.; 20 minutes) and hybridized at 44° C. for 6 hours. After three stringency washes at 76° C. with SSC, the sample was incubated with rabbi-anti-DNP antibody (37° C.; 20 minutes), followed by HRP conjugated goat polyclonal anti-rabbit antibody (37° C.; 16 minutes). HRP was detected as a silver deposit by incubation with silver acetate, hydroquinone, and hydrogen peroxide. Chromosome 17 was sequentially visualized by incubation with a mouse-anti-DIG antibody (37° C.; 20 minutes), followed by AP conjugated goat polyclonal anti-mouse antibody (37° C.; 24 minutes). After washing with SSC, then 200 μL of pH adjust solution (0.5 M Tris, pH 10.0) and 100 μL of Quinone Methide-TAMRA-Dabcyl Multi-Dye Conjugate dissolved in 10 mM glycine buffer (pH 2.0) to a final concentration of 50-500 μM were co-incubated (37° C.; 32 minutes). The stained tissue sections were counterstained with Hematoxylin II (37° C.; 4 minutes) and then incubated with Bluing Reagent (37° C.; 4 minutes). They were then rinsed with a detergent water mixture, dehydrated through a graded ethanol series, cleared with xylene, and manually cover-slipped. Upon introduction of the Quinone Methide-TAMRA-Dabcyl Multi-Dye Conjugate, the alkaline phosphatase converted the Quinone Methide-TAMRA-Dabcyl Multi-Dye Conjugate to a reactive intermediate which was then able to bond to tissue, either proximal to or directly on the labeled Chromosome 17 target. As illustrated in FIG. 9, the Quinone Methide-TAMRA-Dabcyl Multi-Dye Conjugate stained the Chromosome 17 target red.

The Quinone Methide-TAMRA-Dabcyl Multi-Dye Conjugate of this example comprised a quinone methide precursor moiety coupled to the two chromogens. Here, the two chromogens were provided in a "branched" arrangement, using a linker, here lysine, was used to couple the two chromogens to the tyramide moiety. The Quinone Methide-TAMRA-Dabcyl Multi-Dye Conjugate was formed according to the methods described in Example 5.

Example 7 Synthesis of Quinone Methide Cy5-Rhodamine 800 Dual-Dye Conjugate

To a stirring soln. of Cy5 acid 15 (50 mg, 0.096 mmol) in MeCN (5 mL) was added DMAP (13 mg, 0.11 mmol). After the DMAP had dissolved, DSC (27 mg, 0.11 mmol) was added and the resulting mixture was stirred at rt for 30 min. Nε-Boc-L-lysine (47 mg, 0.19 mmol) and triethylamine (49 mg, 0.48 mmol) were then added and the resulting mixture stirred at rt for 30 min. The solvents were then removed under reduced pressure, and the residue was dissolved in $CH_2Cl_2$ (50 mL) and extracted with 1M HCl (3×50 mL) and brine (50 mL). The organic layers were collected, dried over $MgSO_4$, and the solvents removed under reduced pressure. The resulting residue 16 (Cy5-N-boc-L-lysine conjugate) was dissolved in MeCN (5 mL) followed by addition of DMAP (13 mg, 0.11 mmol). After the DMAP had dissolved, DSC (27 mg, 0.11 mmol) was added and the resulting mixture was stirred at rt for 30 min. Quinone methide precursor 17. (52 mg, 0.14 mmol) and triethylamine (49 mg, 0.48 mmol) were then added and the resulting mixture stirred at rt for 30 min. The solvents were then removed under reduced pressure, and the residue was dissolved in $CH_2Cl_2$ (50 mL) and extracted with 1M HCL (3×50 mL) and brine (50 mL). The organic layers were collected, dried over $MgSO_4$, and the solvents removed under reduced pressure. The resulting residue (Quinone methide-Nε-boc-L-lysine-Cy5 conjugate) was dissolved in $CH_2Cl_2$ (5 mL) followed by addition of TFA (1 mL). The resulting mixture was stirred at rt for 30 min, at which point the solvents were removed under reduced pressure. The resulting residue was dissolved in MeCN (3 mL) followed by addition of triethylamine (97 mg, 0.96 mmol) and rhodamine 800 (48 mg, 0.096 mmol). The resulting mixture was stirred at rt for 16 h, at which point the solvents were removed under reduced pressure. The resulting residue was dissolved in MeOH (5 mL) and the mixture directly purified by reverse-phase flash chromatography (SNAP C18 Ultra 60 g, 50 mL/min, 0.05% TFA in $H_2O$:MeOH 4:1 to 0:1 over 10 CV) to give the QM-Cy5-rhodamine 800 conjugate 18 as a green solid (70 mg, 55% yield from Cy5 acid). MS (ESI) m/z (M)$^{2+}$ Scheme 4--Synthesis of Quinone Methide Cy5-Rhodamine 800 dual-dye cnojugate

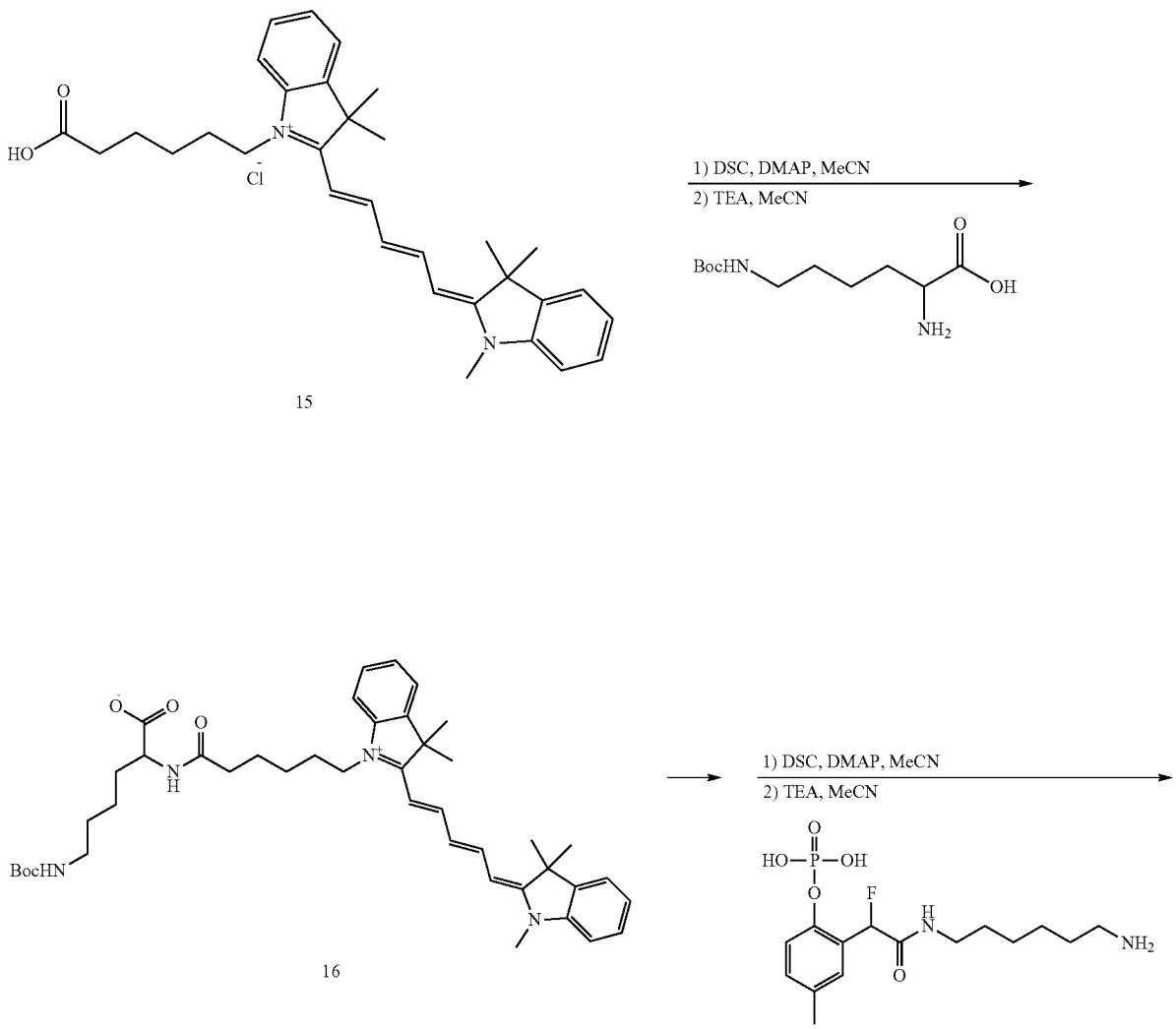

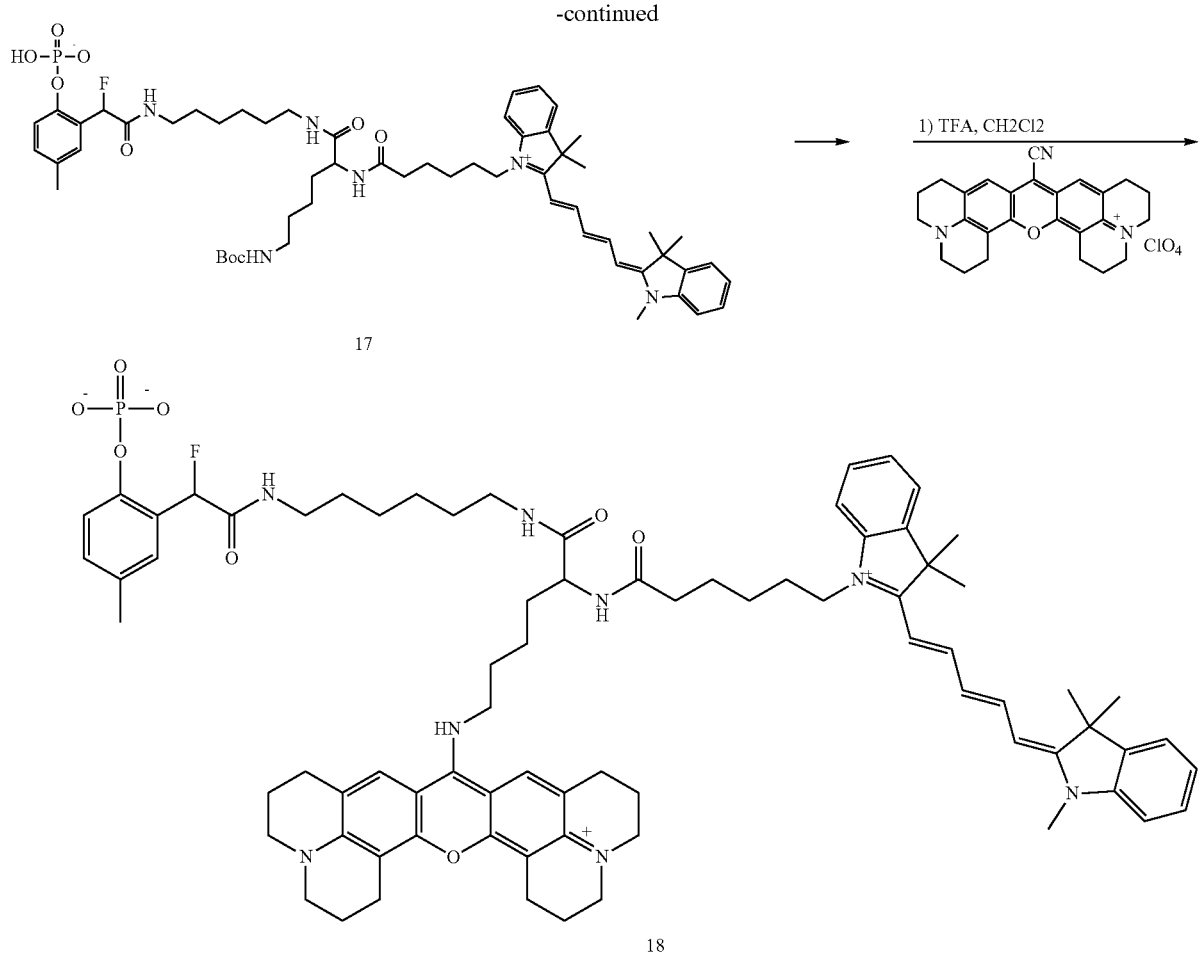

calculated for $C_{78}H_{98}N_8O_8P^{2+}$ 662.4, found 662.1.

Example 8—Quinone Methide-Rhod800-Cy5 Multi-Dye Conjugate (IHC)

The Quinone Methide—Cy5-Rhod800 Multi-Dye Conjugate comprises two chromophores, namely a rhodamine 800 chromophore and a Cy5 chromophore. While rhodamine 800 alone produces a yellow color and Cy5 alone produces a blue color, the multi-dye conjugate produces a green color.

Figure 14:
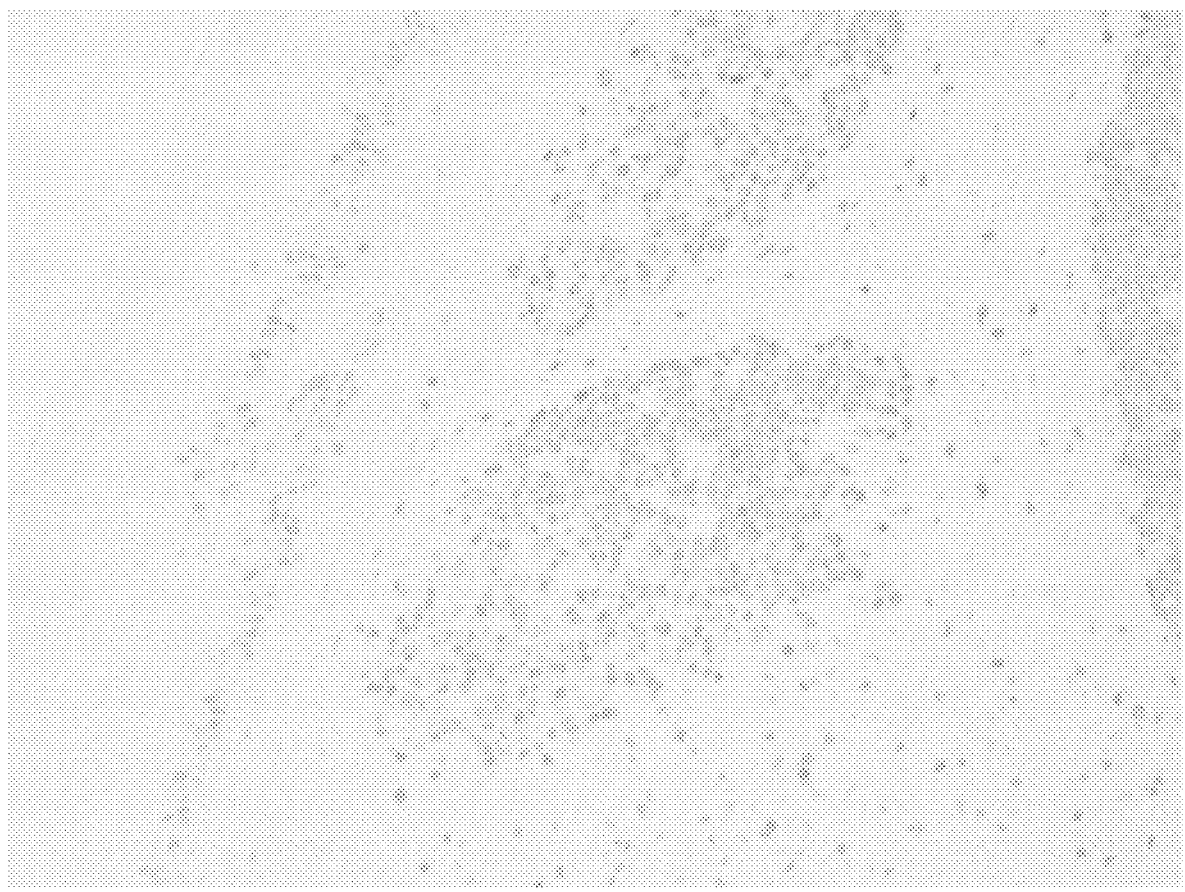
FIG. 14 illustrates a tissue sample stained with a Quinone Methide Cy5-Rhodamine 800 dual-dye, where the Ki67 target is stained green (visible as light grey spots in the black and white drawing).

The Quinone Methide-Rhod800-Cy5 Multi-Dye Conjugate was used in an assay to stain the Ki67 marker in tonsil tissue as described in Example 1. A primary antibody specific to Ki67 was first introduced to the tonsil tissue sample to form an antibody-target complex. A secondary antibody was then introduced, namely an anti-Ki67 antibody conjugated to an alkaline phosphatase enzyme. Upon introduction of the Quinone Methide-Cy5-Rhod800 Multi-Dye Conjugate, the alkaline phosphatase converted the Quinone Methide-Cy5-Rhod800 Multi-Dye Conjugate to a reactive intermediate which was then able to bond to tissue, either proximal to or directly on the labeled Ki-67 target. As illustrated in FIG. 14, the Quinone Methide—Cy5-Rhod800 Multi-Dye Conjugate stained the Ki-67 target green.

All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

ADDITIONAL EXEMPLARY EMBODIMENTS

The following embodiments are also explicitly disclosed. This is not intended to be an exhaustive list.

1. A multi-dye conjugate comprising a tissue reactive moiety and at least two chromophores, wherein the tissue reactive moiety is selected from the group consisting of a quinone methide precursor or a tyramide, and wherein the at least two chromophores are different.
2. The conjugate of embodiment 1, wherein the at least two chromophores are selected from the group consisting of TAMRA, Dabsyl, Cy5, Dabcyl, Cy3, Cy7, Cy3.5, Cy3B, Cy5.5, rhodamine 800, and fluorescein.
3. The conjugate of embodiment 1 or 2, wherein the multi-dye conjugate displays a color different than a color of either of the at least two chromophores.
4. The conjugate of any of embodiments 1 to 3, wherein the at least two chromophores are conjugated to the tissue reactive moiety through a multi-functional linker.
5. The conjugate of embodiment 4, wherein the multi-functional linker is a heterobifunctional linker.
6. The conjugate of embodiment 5, wherein the heterobifunctional linker is lysine or a derivative thereof.

7. The conjugate of embodiment 3, wherein the multifunctional linker is a dendrimer.

8. The conjugate of embodiment 7, wherein the dendrimer is selected from the group consisting of polyamidoamine (PAMAM) dendrimers, Janus dendrimers, and bis-MPA dendrimers.

9. The conjugate of embodiment 3, wherein the multifunctional linker is selected from the group consisting of norspermidine and spermine.

10. The conjugate of embodiment 3, wherein the multifunctional linker has a molecular weight ranging between about 50 g/mol and about 300 g/mol.

11. The conjugates of any of embodiments 1 to 3, wherein a first of the at least two chromophores is conjugated directly or indirectly to the tissue reactive moiety, and a second of the at least two chromophores is conjugated directly or indirectly to the first chromophore.

12. A multi-dye conjugate having Formula (I):

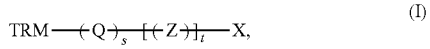

(I)

wherein
"TRM" is a tissue reactive moiety;
Q is a branched or unbranched, linear or cyclic, substituted or unsubstituted group having between 2 and 40 carbon atoms, and optionally having one or more heteroatoms selected from O, N, or S;
Z is a bond or a branched or unbranched, linear or cyclic, substituted or unsubstituted, saturated or unsaturated, group having between 2 and 20 carbon atoms, and optionally having one or more heteroatoms selected from O, N, or S;
X is H, -[(Q)$_d$-[A]$_n$]$_e$; —N—([Z]—[X])$_2$; or —C(H)([Z]—[X]);
A is a chromogen;
d is 0 or 1;
e is an integer ranging from 1 to 4;
s is 0 or an integer ranging from 1 to 4; and
t is 0 or an integer ranging from 1 to 10;
provided that the multi-dye conjugate comprises at least two A groups.

13. The multi-dye conjugate of embodiment 12, wherein TRM has the structure of Formula (II):

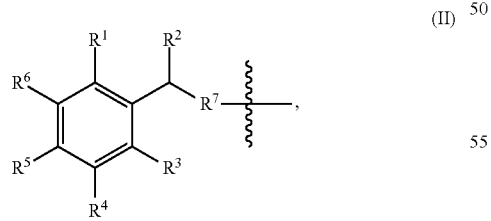

(II)

wherein
$R^1$ is selected from the group consisting of phosphate, amide, nitro, urea, sulfate, methyl, ester, beta-lactam, and a sugar;
$R^2$ is a halide;
$R^3$, $R^4$, $R^5$, and $R^6$ are independently selected from hydrogen or an aliphatic group having between 1 and 4 carbon atoms; and $R^7$ is —(CH$_2$)$_w$NH—, —O(CH$_2$)$_w$NH—, —N(H)C(O)(CH$_2$)$_w$NH—, —C(O)N(H)(CH$_2$)$_w$NH—, —(CH$_2$)$_w$O—, —O(CH$_2$)$_w$O—, —O(CH$_2$CH$_2$O)$_w$—, —N(H)C(O)(CH$_2$)$_w$O—, —C(O)N(H)(CH$_2$)$_w$O—, —C(o)N(H)(CH$_2$CH$_2$O)$_w$—, —(CH$_2$)$_w$S—, —O(CH$_2$)$_w$S—, —N(H)C(O)(CH$_2$)$_w$S—, —C(O)N(H)(CH$_2$)$_w$S—, —(CH$_2$)$_w$NH—, —C(O)N(H)(CH$_2$CH$_2$O)$_w$CH$_2$CH$_2$NH, —C(O)(CH$_2$CH$_2$O)$_w$CH$_2$CH$_2$NH—, —C(O)N(H)(CH$_2$)NHC(O)CH(CH$_3$)(CH$_2$)$_w$NH—, or —N(H)(CH$_2$)$_w$NH—, where w is an integer ranging from 1 to 12.

14. The multi-dye conjugate of embodiment 12, wherein TRM has the structure of Formula (IIc):

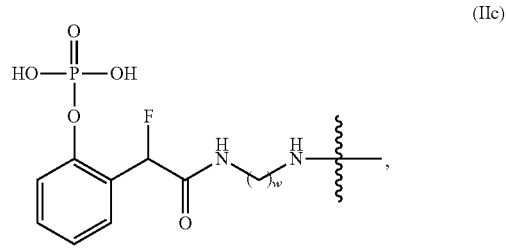

(IIc)

wherein
w ranges from 1 to 12.

15. The multi-dye conjugate of embodiment 14, wherein w ranges from 2 to 6.

16. The multi-dye conjugate of embodiment 12, wherein TRM is a tyramide or a tyramide derivative.

17. The multi-dye conjugate of any of embodiments 12 to 16, wherein Q has the structure of Formula (IVa):

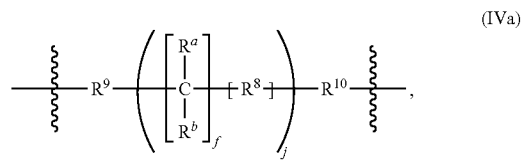

(IVa)

wherein
f is 0, 1, or 2;
$R^8$ is a bond, O, S, or N(R$^c$)(R$^d$);
$R^a$ and $R^b$ are independently H, a C$_1$-C$_4$ alkyl group, F, Cl, or —N(R$^c$)(R$^d$);
$R^c$ and $R^d$ are independently selected from CH$_3$ or H;
$R^9$ and $R^{10}$ are independently a bond or a group selected from carbonyl, amide, imide, ester, ether, amine, thione, thiol; and
j is an integer ranging from 1 to 8.

18. The multi-dye conjugate of any of embodiments 12 to 16, wherein Q has the structure of Formula (IVb):

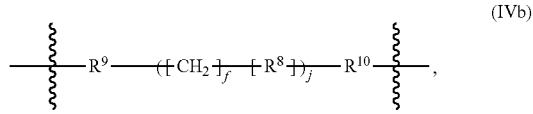

(IVb)

wherein f is 0, 1, or 2;

$R^8$ is a bond, O, S, or $N(R^c)(R^d)$;

$R^c$ and $R^d$ are independently $CH_3$ or H;

$R^9$ and $R^{10}$ are independently a bond or a group selected from carbonyl, amide, imide, ester, ether, amine, or thiol; and j is an integer ranging from 1 to 8.

19. The multi-dye conjugate of any of embodiments 12 to 18, wherein Z has the structure of Formula (Va):

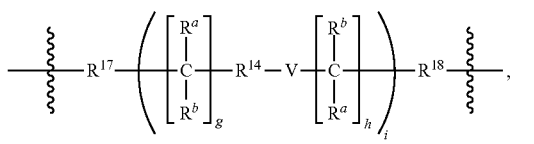

(Va)

wherein $R^{17}$ and $R^{18}$ are independently a bond or a group selected from carbonyl, amide, imide, ester, ether, —NH, —N—, thione, or thiol;

$R^{14}$ is a bond, a carbonyl, an imine, or a thione;

V is a bond, —C($R^{15}$)($R^{16}$)—, —O—, —S—, —N($R^{16}$)—, —N(X)—; —C($R^{15}$)(X); —C(X)$_2$—, or —C($R^{15}$)(N($R^{16}$)(X));

X is as defined herein;

$R^a$ and $R^b$ are independently H, a $C_1$-$C_4$ alkyl group, F, Cl, or N($R^{15}$)($R^{16}$);

$R^{15}$ and $R^{16}$ are independently a bond or —$CH_3$ or H;

g is 0 or an integer ranging from 1 to 4;

h is 0 or an integer ranging from 1 to 8; and i is 1 or 2.

20. The multi-dye conjugate of embodiment 19, wherein g is 0, $R^{14}$ is a carbonyl, V is —C($R^{15}$)(N($R^{16}$)(X)), $R^{15}$ is H, $R^{16}$ is H, and h ranges from 2 to 6.

21. The multi-dye conjugate of embodiment 19, wherein g is 0, $R^{14}$ is a carbonyl, V is —C($R^{15}$)(N($R^{16}$)(X)), $R^{15}$ is H, $R^{16}$ is H, and h ranges from 2 to 4.

22. The multi-dye conjugate of embodiment 19, wherein g is 0, $R^{14}$ is a carbonyl, V is —C($R^{15}$)(N($R^{16}$)(X)), $R^{15}$ is H, $R^{16}$ is H, and h is 4.

23. The multi-dye conjugate of embodiment 19, wherein g is 0, $R^{14}$ is a carbonyl, V is —C($R^{15}$)(N($R^{16}$)(X)), $R^{15}$ is H, $R^{16}$ is H, $R^a$ and $R^b$ are H, and h ranges from 2 to 4.

24. The multi-dye conjugate of embodiment 19, wherein g is 0, $R^{14}$ is a carbonyl, V is —C($R^{15}$)(N($R^{16}$)(X)), $R^{15}$ is H, $R^{16}$ is H, $R^a$ and $R^b$ are H, $R^9$ is a bond, $R^{10}$ is an amine; and h ranges from 2 to 4.

25. The multi-dye conjugate of embodiment 19, wherein g is 0, $R^{14}$ is a carbonyl, V is —C($R^{15}$)(N($R^{16}$)(X)), $R^{15}$ is H, $R^{16}$ is H, $R^a$ and $R^b$ are H, $R^9$ is a bond, $R^{10}$ is an amine; X is -[(Q)$_d$-[A]$_n$]$_e$, d, n, and e are each 1, and h ranges from 2 to 4.

26. The multi-dye conjugate of embodiment 12, wherein the multi-dye conjugate has the structure:

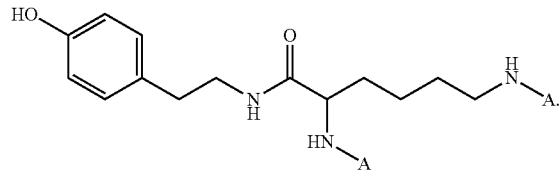

27. The multi-dye conjugate of embodiment 12, wherein the multi-dye conjugate has the structure:

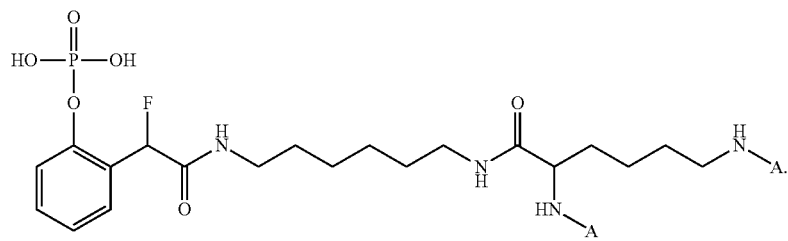

28. The multi-dye conjugate of embodiment 12, wherein the multi-dye conjugate has the structure:
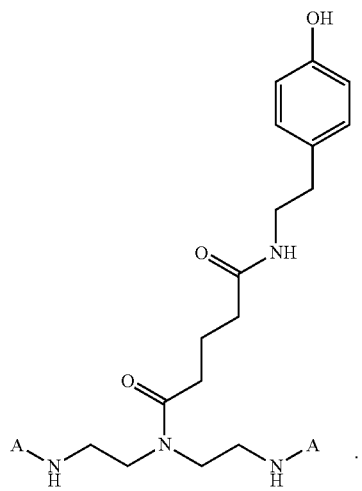
29. The multi-dye conjugate of embodiment 12, wherein the multi-dye conjugate has the structure:
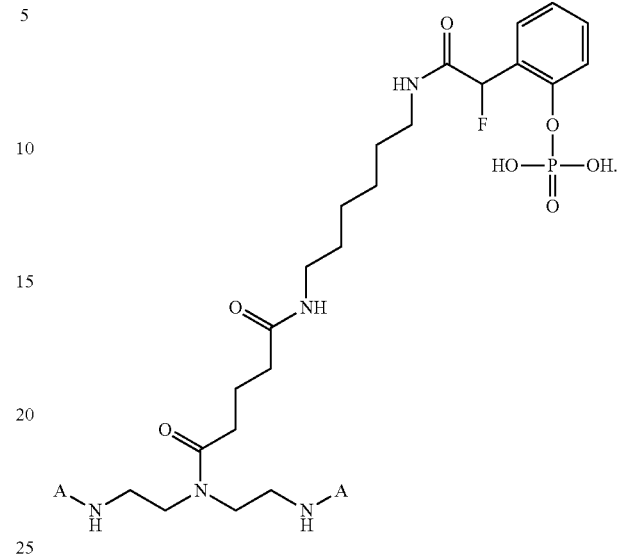
30. The multi-dye conjugate of embodiment 12, wherein the multi-dye conjugate has the structure:
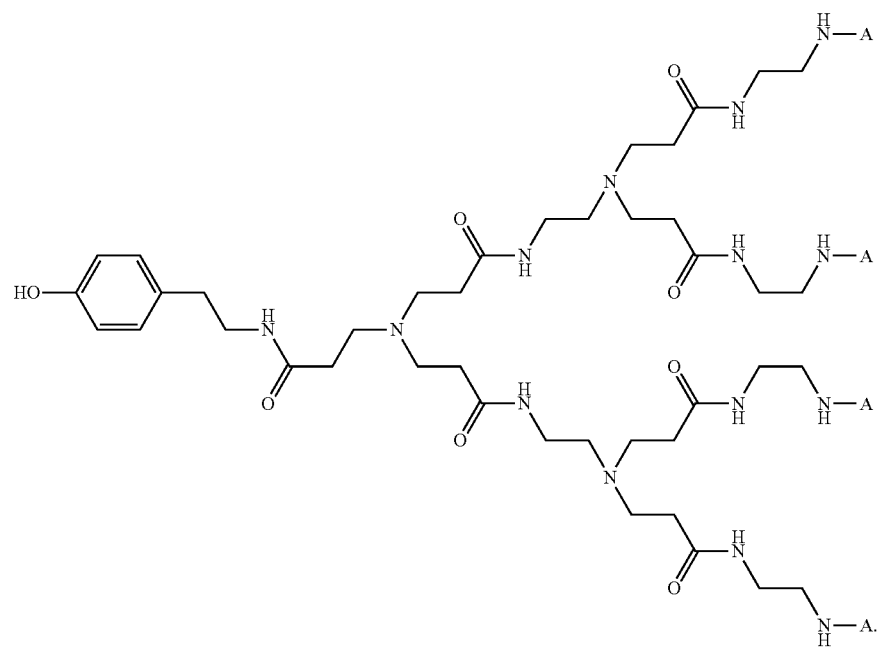

31. The multi-dye conjugate of embodiment 12, where multi-dye conjugate has the structure:
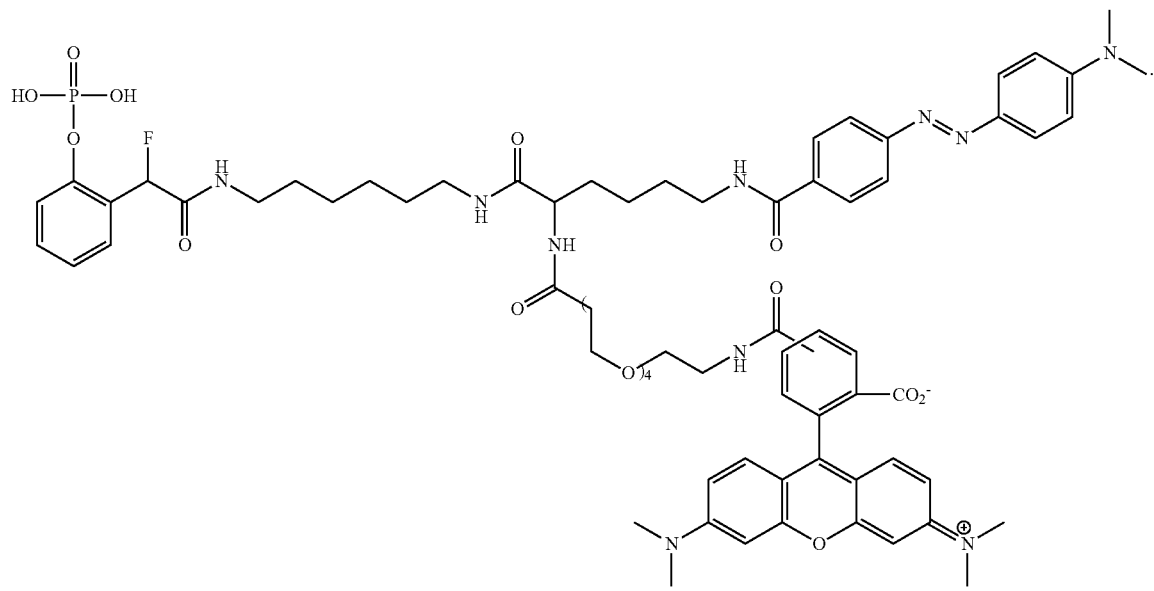
32. The multi-dye conjugate of embodiment 12, where multi-dye conjugate has the structure:
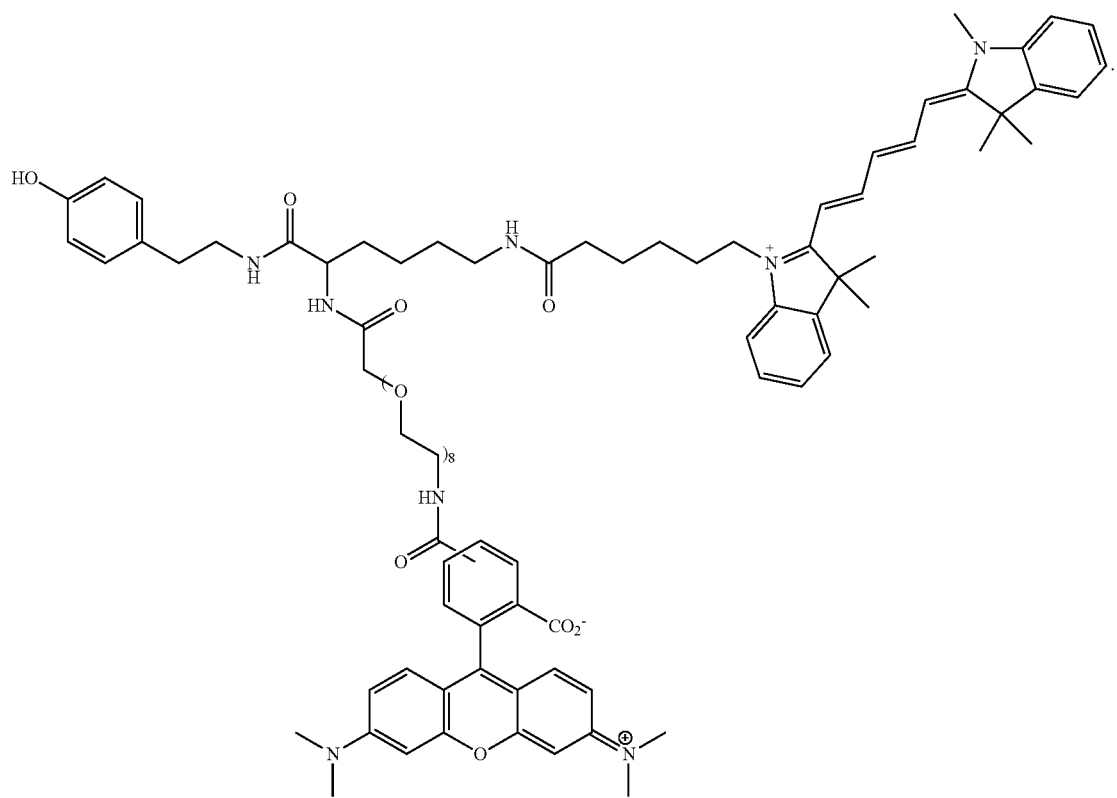

33. The multi-dye conjugate of embodiment 12, where multi-dye conjugate has the structure:
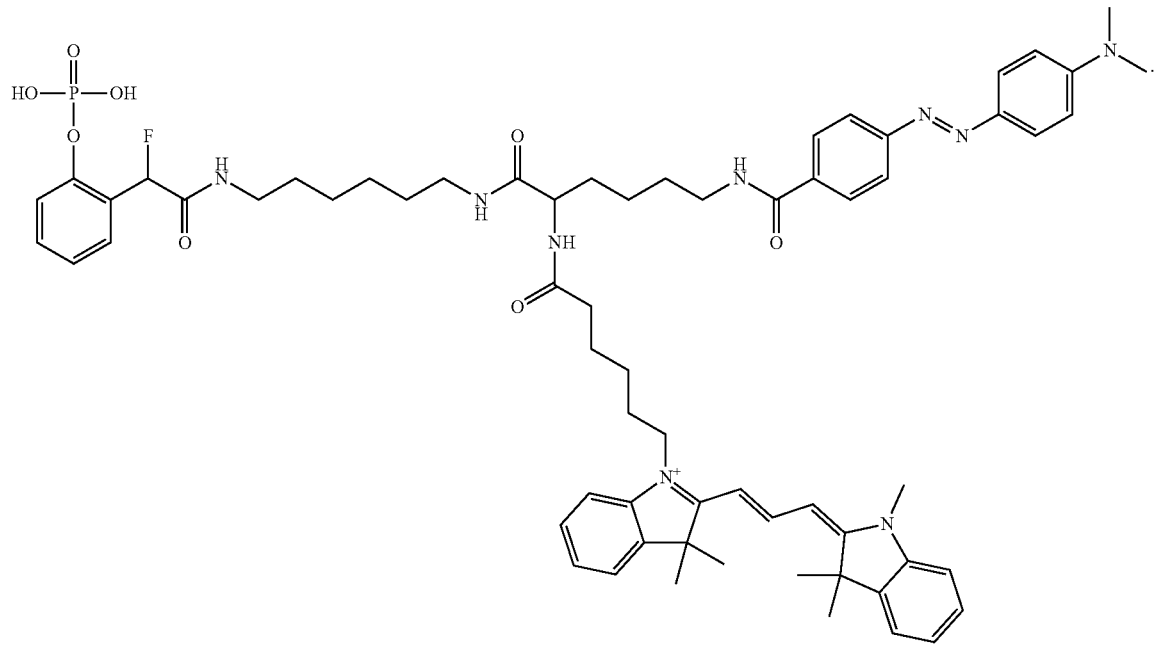 [SMILES: CN(C)c1ccc(/N=N/c2ccc(C(=O)NCCCCC(NC(=O)CCCCC[N+]3=C(/C=C/C=C4/N(C)c5ccccc5C4(C)C)C(C)(C)c4ccccc43)C(=O)NCCCCCCNC(=O)C(F)c3ccccc3OP(=O)(O)O)cc2)cc1]
34. The multi-dye conjugate of embodiment 12, where multi-dye conjugate has the structure:
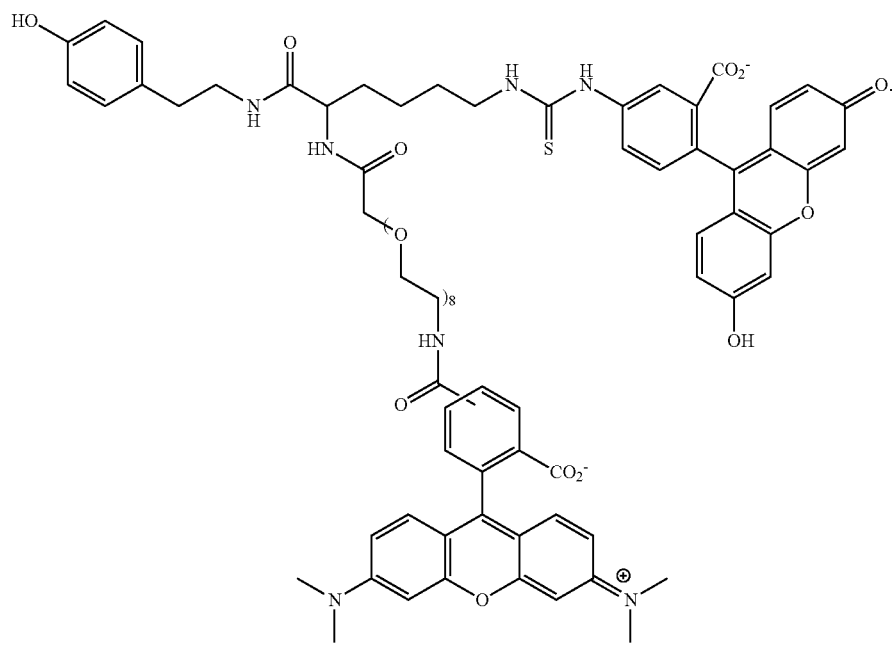

35. The multi-dye conjugate of embodiment 12, where multi-dye conjugate is selected from the group consisting of:

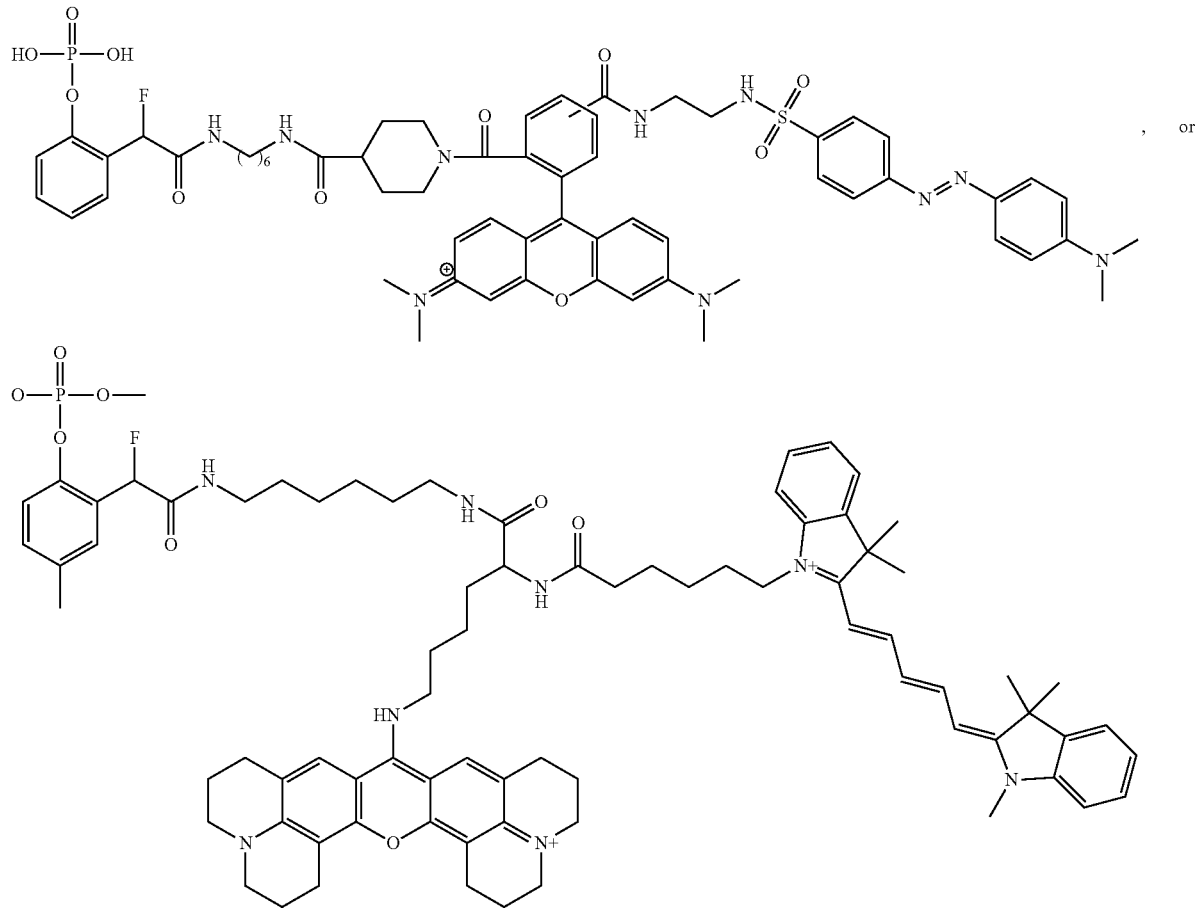

36. A method of detecting a first target in a biological sample, comprising
    (i) contacting the biological sample with a first detection probe specific to the first target to form a first detection probe-target complex;
    (ii) contacting the biological sample with a first labeling conjugate specific for the first detection probe, the first labeling conjugate comprising a first enzyme; and
    (iii) contacting the biological sample with a first multi-dye conjugate, the first multi-dye conjugate comprising a tissue reactive moiety conjugated to at least two chromogens, wherein the first enzyme converts the first multi-dye conjugate to a first reactive intermediate which covalently bonds to the biological sample proximally to or directly on the first target.
37. The method of embodiment 36, wherein the first detection probe is a first primary antibody and the first labeling conjugate comprises an anti-species antibody conjugated to the first enzyme.
38. The method of claim 36, wherein the first detection probe comprises a first nucleic acid probe conjugated to a label, and wherein the first labeling conjugate comprises an anti-label antibody conjugated to the first antibody.
39. The method of any of claims 36 to 38, wherein the first enzyme is selected from the group consisting of phosphatase, phosphodiesterase, esterase, lipase, amidase, protease, nitroreductase, urease, sulfatase, cytochrome P450, alpha-glucosidase, betaglucosidase, beta-lactamase, alpha-glucoronidase, beta-glucoronidase, alpha-5 galactosidase, beta-galactosidase, alpha-lactase and beta-lactase.
40. The method of any of embodiment 36 to 39, wherein the first multi-dye conjugate comprises a quinone methide precursor moiety and wherein the first enzyme is alkaline phosphatase.
41. The method of any of embodiments 36 to 40, wherein the at least two chromophores of the first multi-dye conjugate are selected from the group consisting of TAMRA, Dabsyl, Cy5, Dabcyl, Cy3, and fluorescein.
42. The method of embodiment 41, wherein the at least two chromophores are conjugated to the tissue reactive moiety through a multi-functional linker.
43. The method of embodiment 42, wherein the multi-functional linker is lysine.
44. The method of embodiment 42, wherein the multi-functional linker is a dendrimer.
45. The method of any of embodiments 36 to 44, wherein a first of the at least two chromophores of the first multi-dye conjugate is conjugated directly or indirectly to the tissue reactive moiety, and a second of the at least two chromophores is conjugated directly or indirectly to the first chromophore.

46. The method of any of embodiments 36 to 45, wherein the method further comprises contacting (i) contacting the biological sample with a second detection probe specific to a second target to form a second detection probe-target complex; (ii) contacting the biological sample with a second labeling conjugate specific for the second detection probe, the second labeling conjugate comprising a second enzyme; and (iii) contacting the biological sample with a second multi-dye conjugate, the second multi-dye conjugate comprising a tissue reactive moiety conjugated to at least two chromogens, wherein the second enzyme converts the second multi-dye conjugate to a second reactive intermediate which covalently bonds to the biological sample proximally to or directly on the second target, wherein a signal displayed by the first multi-dye conjugate is different from a color displayed by the second multi-dye conjugate.

47. The method of embodiment 46, wherein the second multi-dye conjugate comprises a tyramide moiety and wherein the first enzyme is a horseradish peroxidase.

48. The method of embodiment 46 or 47, wherein the at least two chromophores of the second multi-dye conjugate are selected from the group consisting of TAMRA, Dabsyl, Cy5, Dabcyl, Cy3, and fluorescein.

49. The method of any of embodiments 46 to 48, wherein the at least two chromophores of the second multi-dye conjugate are conjugated to the tissue reactive moiety through a multi-functional linker.

50. The method of embodiment 49, wherein the multi-functional linker is lysine.

51. The method of embodiment 49, wherein the multi-functional linker is a dendrimer.

52. The method of any of embodiments 46 to 48, wherein a first of the at least two chromophores of the second multi-dye conjugate is conjugated directly or indirectly to the tissue reactive moiety, and a second of the at least two chromophores is conjugated directly or indirectly to the first chromophore.

53. The method of any of embodiments 36 to 45, wherein the method further comprises contacting (i) contacting the biological sample with a second detection probe specific to a second target to form a second detection probe-target complex; (ii) contacting the biological sample with a second labeling conjugate specific for the second detection probe, the second labeling conjugate comprising a second enzyme; and (iii) contacting the biological sample with a TSA single chromogen conjugate or QMSA single chromogen conjugate, wherein the second enzyme converts the TSA or QMSA single chromogen conjugate to a second reactive intermediate which covalently bonds to the biological sample proximally to or directly on the second target, wherein a color displayed by the first multi-dye conjugate is different from a color displayed by the TSA or QMSA single chromogen conjugate.

54. The method of any of embodiments 36 to 53, wherein one or more of the steps are performed by an automated system.

55. A method of detecting targets within in a biological sample, comprising
(i) contacting the biological sample with a first detection probe specific to a first target to form a first detection probe-target complex;
(ii) contacting the biological sample with a first labeling conjugate specific for the first detection probe, the first labeling conjugate comprising a first enzyme;
(iii) contacting the biological sample with a first conjugate selected from the group consisting of (a) a first multi-dye conjugate, the first first multi-dye conjugate comprising a tissue reactive moiety and at least two chromophores, wherein the tissue reactive moiety is selected from the group consisting of a quinone methide precursor or a tyramide; (b) a first TSA-single chromogen conjugate, and (c) a first QMSA-single chromogen conjugate; wherein the first enzyme converts the first conjugate conjugate to a first reactive intermediate which covalently bonds to the biological sample proximally to or directly on the first target;
(iv) contacting the biological sample with a second detection probe specific to a second target to form a second detection probe-target complex;
(v) contacting the biological sample with a second labeling conjugate specific for the second detection probe, the second labeling conjugate comprising a second enzyme;
(vi) contacting the biological sample with a second conjugate selected from the group consisting of (a) a second multi-dye conjugate, the second multi-dye conjugate comprising a tissue reactive moiety and at least two chromophores, wherein the tissue reactive moiety is selected from the group consisting of a quinone methide precursor or a tyramide; (b) a second TSA-single chromogen conjugate, and (c) a second QMSA-single chromogen conjugate; wherein the second enzyme converts the second conjugate conjugate to a second reactive intermediate which covalently bonds to the biological sample proximally to or directly on the second target; and
(vii) wherein the first and second conjugates display different signals.

56. A method of detecting a first target in a biological sample, comprising
(i) contacting the biological sample with a first detection probe specific to the first target to form a first detection probe-target complex;
(ii) contacting the biological sample with a first labeling conjugate specific for the first detection probe, the first labeling conjugate comprising a first enzyme; and
(iii) contacting the biological sample with a first multi-dye conjugate of Formula (I),

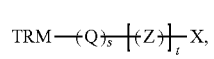

$$\text{TRM}-(Q)_s-[(Z)]_t-X, \quad (I)$$

wherein
"TRM" is a tissue reactive moiety;
Q is a branched or unbranched, linear or cyclic, substituted or unsubstituted group having between 2 and 40 carbon atoms, and optionally having one or more heteroatoms selected from O, N, or S;
Z is a bond or a branched or unbranched, linear or cyclic, substituted or unsubstituted, saturated or unsaturated, group having between 2 and 20 carbon atoms, and optionally having one or more heteroatoms selected from O, N, or S;

X is H, -[(Q)$_d$-[A]$_n$]$_e$; —N—([Z]—[X])$_2$; or —C(H)([Z]—[X]);

A is a chromogen;

d is 0 or 1;

e is an integer ranging from 1 to 4;

s is 0 or an integer ranging from 1 to 4; and t is 0 or an integer ranging from 1 to 10; and wherein the first enzyme converts the first multi-dye conjugate to a first reactive intermediate which covalently bonds to the biological sample proximally to or directly on the first target.

57. The method of embodiment 56, wherein the method further comprises (i) contacting the biological sample with a second detection probe specific to a second target to form a second detection probe-target complex; (ii) contacting the biological sample with a second labeling conjugate specific for the second detection probe, the second labeling conjugate comprising a second enzyme; and (iii) contacting the biological sample with a second multi-dye conjugate of Formula (I), wherein a color displayed by the first multi-dye conjugate is different from a color displayed by the second multi-dye conjugate.

58. The method of any of embodiments 56 and 57, wherein Q has the structure of Formula (IVa)

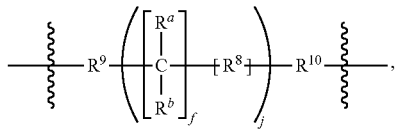 (IVa)

wherein f is 0, 1, or 2;

$R^8$ is a bond, O, S, or N($R^c$)($R^d$);

$R^a$ and $R^b$ are independently H, a $C_1$-$C_4$ alkyl group, F, Cl, or —N($R^c$)($R^d$);

$R^c$ and $R^d$ are independently selected from $CH_3$ or H;

$R^9$ and $R^{10}$ are independently a bond or a group selected from carbonyl, amide, imide, ester, ether, amine, thione, thiol; and j is an integer ranging from 1 to 8.

59. The method of any of embodiments 56 and 57, wherein Q has the structure of Formula (IVb):

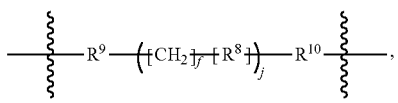 (IVb)

wherein f is 0, 1, or 2;

$R^8$ is a bond, O, S, or N($R^c$)($R^d$);

$R^c$ and $R^d$ are independently $CH_3$ or H;

$R^9$ and $R^{10}$ are independently a bond or a group selected from carbonyl, amide, imide, ester, ether, amine, or thiol; and j is an integer ranging from 1 to 8.

60. The method of any of embodiments 56 and 57, wherein Z has the structure of Formula (Va):

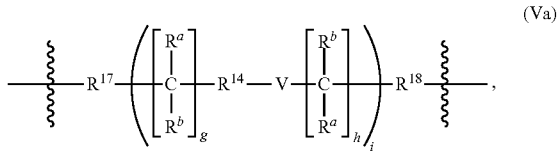 (Va)

wherein $R^{17}$ and $R^{18}$ are independently a bond or a group selected from carbonyl, amide, imide, ester, ether, —NH, —N—, thione, or thiol;

$R^{14}$ is a bond, a carbonyl, an imine, or a thione;

V is a bond, —C($R^{15}$)($R^{16}$)—, —O—, —S—, —N($R^{16}$)—, —N(X)—; —C($R^{15}$)(X); —C(X)$_2$—, or —C($R^{15}$)(N($R^{16}$)(X));

X is as defined herein;

$R^a$ and $R^b$ are independently H, a $C_1$-$C_4$ alkyl group, F, Cl, or N($R^{15}$)($R^{16}$);

$R^{15}$ and $R^{16}$ are independently a bond or —$CH_3$ or H;

g is 0 or an integer ranging from 1 to 4;

h is 0 or an integer ranging from 1 to 8; and i is 1 or 2.

61. A kit comprising:

(i) a multi-dye conjugate having Formula (I):

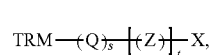 (I)

wherein

"TRM" is a tissue reactive moiety;

Q is a branched or unbranched, linear or cyclic, substituted or unsubstituted group having between 2 and 40 carbon atoms, and optionally having one or more heteroatoms selected from O, N, or S;

Z is a bond or a branched or unbranched, linear or cyclic, substituted or unsubstituted, saturated or unsaturated, group having between 2 and 20 carbon atoms, and optionally having one or more heteroatoms selected from O, N, or S;

X is H, -[(Q)$_d$-[A]$_n$]$_e$; —N—([Z]—[X])$_2$; or —C(H)([Z]—[X]);

A is a chromogen;

d is 0 or 1;

e is an integer ranging from 1 to 4;

s is 0 or an integer ranging from 1 to 4; and t is 0 or an integer ranging from 1 to 10;

wherein the multi-dye conjugate comprises at least two A groups;

(ii) a detection probe specific to a target; and (iii) a labeling conjugate specific for the first detection probe.

62. The kit of embodiment 61, wherein the detection probe is a primary antibody.

63. The kit of embodiment 61, wherein the detection probe is a nucleic acid probe conjugated to a label.

64. The kit of embodiment 61 or 62, wherein the labeling conjugate is an anti-antibody antibody, and wherein the anti-antibody antibody is conjugated to an enzyme.

65. The kit of embodiment 61 or 63, wherein the labeling conjugate is an anti-label antibody, and wherein the anti-label antibody is conjugated to an enzyme.
66. The kit of any of embodiments 61 to 65, wherein the target is CD8.
67. The kit of any of embodiments 61 to 65, wherein the target is Ki-67.
68. The kit of any of embodiments 61 to 65, wherein the target is Chromosome-17.
69. A conjugate comprising a tyramide moiety, TAMRA, and Cy5.
70. The conjugate of embodiment 69, wherein the TAMRA is coupled directly or indirectly to the tyramide moiety, and wherein the Cy5 is coupled directly or indirectly to the TAMRA.
71. A conjugate comprising a tyramide moiety, TAMRA, and FITC.
72. The conjugate of embodiment 71, wherein the tyramide moiety, TAMRA, and FITC are coupled through a multi-functional linker.
73. The conjugate of embodiment 72, wherein the multi-functional linker is lysine or a derivative thereof.
74. A conjugate comprising a quinone methide precursor moiety, Dabcyl, and Cy3.
75. The conjugate of embodiment 74, wherein the quinone methide precursor moiety, Dabcyl, and Cy3 are coupled through a multi-functional linker.
76. The conjugate of embodiment 75, wherein the multi-functional linker is lysine or a derivative thereof.
77. A conjugate comprising a quinone methide precursor moiety, TAMRA, and Dabcyl.
78. The conjugate of embodiment 77, wherein the quinone methide precursor moiety, TAMRA, and Dabcyl are coupled through a multi-functional linker.
79. The conjugate of embodiment 78, wherein the multi-functional linker is lysine or a derivative thereof.
80. A conjugate comprising a quinone methide precursor moiety, TAMRA, and Dabsyl.
81. The conjugate of embodiment 80, wherein the quinone methide precursor moiety, TAMRA, and Dabsyl are coupled through a multi-functional linker.
82. The conjugate of embodiment 81, wherein the multi-functional linker is lysine or a derivative thereof.

Although the disclosure herein has been described with reference to particular embodiments, it is to be understood that these embodiments are merely illustrative of the principles and applications of the present disclosure. It is therefore understood that numerous modifications may be made to the illustrative embodiments and that other arrangements may be devised without departing from the spirit and scope of the present disclosure as defined by the appended claims.

The invention claimed is:

1. A multi-dye conjugate comprising a tissue reactive moiety and at least two chromophores, wherein the tissue reactive moiety is a quinone methide precursor moiety and wherein the at least two chromophores are different; wherein the at least two chromophores of the multi-dye conjugate are covalently conjugated to a heterobifunctional linker or a polyamine linker having between 2 and 10 amine groups, and wherein the heterobifunctional linker or the polyamine linker is covalently conjugated to the quinone methide precursor moiety, and wherein the quinone methide precursor moiety has the structure of Formula (II):

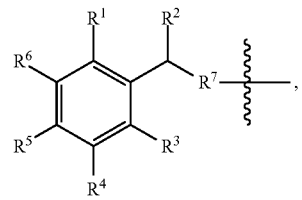

wherein
$R^1$ is a group selected from phosphate, amide, nitro, urea, sulfate, methyl, ester, beta-lactam, or a sugar;
$R^2$ is a halide;
$R^3$, $R^4$, $R^5$, and $R^6$ are independently selected from hydrogen or an aliphatic group having between 1 and 4 carbon atoms; and
$R^7$ is $-(CH_2)_w NH-$, $-O(CH_2)_w NH-$, $-N(H)C(O)(CH_2)_w NH-$, $-C(O)N(H)(CH_2)_w NH-$, $-(CH_2)_w O-$, $-O(CH_2)_w O-$, $-O(CH_2CH_2O)_w-$, $-N(H)C(O)(CH_2)_w O-$, $-C(O)N(H)(CH_2)_w O-$, $-C(o)N(H)(CH_2CH_2O)_w-$, $-(CH_2)_w S-$, $-O(CH_2)_w S-$, $-N(H)C(O)(CH_2)_w S-$, $-C(O)N(H)(CH_2)_w S-$, $-(CH_2)_w NH-$, $-C(O)N(H)(CH_2 CH_2O)_w CH_2CH_2NH$, $-C(O)(CH_2 CH_2O)_w CH_2CH_2NH-$, $-C(O)N(H)(CH_2)NHC(O)CH(CH_3)(CH_2)_w NH-$, or $-N(H)(CH_2)_w NH-$, where w is an integer ranging from 1 to 12; and wherein the wavy line indicates covalent linkage point of the heterobifunctional linker or the polyamine linker.

2. The multi-dye conjugate of claim 1, wherein the at least two chromophores are selected from the group consisting of TAMRA, Dabsyl, Cy5, Dabcyl, Cy3, Cy7, Cy3.5, Cy3B, Cy5.5, rhodamine 800, fluorescein, and derivatives or analogs thereof.

3. The multi-dye conjugate of claim 1, wherein a first of the at least two chromophores comprises a yellow or a yellow-like color.

4. The multi-dye conjugate of claim 1, wherein a second of the at least two chromophores comprises a cyan or a cyan-like color.

5. The multi-dye conjugate of claim 1, wherein a first of the at least two chromophores comprises a rhodamine or a derivative or an analog thereof.

6. The multi-dye conjugate of claim 5, wherein the rhodamine or the derivative or analog thereof comprises rhodamine 800.

7. The multi-dye conjugate of claim 6, wherein a second of the at least two chromophores is selected from the group consisting of TAMRA or a derivative or an analog thereof, Dabsyl or a derivative or an analog thereof, Cy5 or a derivative or an analog thereof, Dabcyl or a derivative or an analog thereof, Cy3 or a derivative or an analog thereof, Cy7 or a derivative or an analog thereof, Cy3.5 or a derivative or an analog thereof, Cy3B or a derivative or an analog thereof, Cy5.5 or a derivative or an analog thereof, and fluorescein or a derivative or an analog thereof.

8. The multi-dye conjugate of claim 1, wherein a first of the at least two chromophores comprises Cy5 or a derivative or an analog thereof.

9. The multi-dye conjugate of claim 8, wherein a second of the at least two chromophores is selected from the group consisting of a rhodamine or a derivative or an analog thereof, Dabsyl or a derivative or an analog thereof, TAMRA or a derivative or an analog thereof, Dabcyl or a derivative or an analog thereof, Cy3 or a derivative or an analog thereof, Cy7 or a derivative or an analog thereof, Cy3.5 or a derivative or an analog thereof, Cy3B or a derivative or an analog thereof, Cy5.5 or a derivative or an analog thereof, and fluorescein or a derivative or an analog thereof.

10. The multi-dye conjugate of claim 1, wherein the heterobifunctional linker or the polyamine linker comprises a molecular weight ranging from between about 50 g/mol to about 300 g/mol.

11. The multi-dye conjugate of claim 1, wherein the heterobifunctional linker or the polyamine linker is derived from lysine or a derivative or analog thereof.

12. A conjugate comprising (i) quinone methide precursor moiety, (ii) a rhodamine or a derivative or an analog thereof, and (iii) Cy5 or a derivative or an analog thereof; wherein the rhodamine or the derivative or the analog thereof and the Cy5 or the derivative or the analog thereof are conjugated to a heterobifunctional or a polyamine linker having between 2 and 10 amine groups, and wherein the heterobifunctional linker or the polyamine linker is covalently conjugated to the quinone methide precursor moiety; and wherein the quinone methide precursor moiety has the structure of Formula (II):

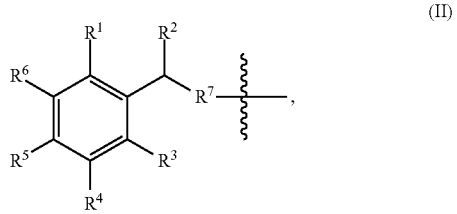

(II)

wherein $R^1$ is a group selected from phosphate, amide, nitro, urea, sulfate, methyl, ester, beta-lactam, or a sugar;

$R^2$ is a halide;

$R^3$, $R^4$, $R^5$, and $R^6$ are independently selected from hydrogen or an aliphatic group having between 1 and 4 carbon atoms; and $R_7$ is —$(CH_2)_w$NH—, —O$(CH_2)_w$NH—, —N(H)C(O)$(CH_2)_w$NH—, —C(O)N(H)$(CH_2)_w$NH—, —$(CH_2)_w$O—, —O$(CH_2)_w$O—, —O$(CH_2CH_2O)_w$—, —N(H)C(O)$(CH_2)_w$O—, —C(O)N(H)$(CH_2)_w$O—, —C(o)N(H)$(CH_2CH_2O)_w$—, -$(CH_2)_w$S—, —O$(CH_2)_w$S—, —N(H)C(O)$(CH_2)_w$S—, —C(O)N(H)$(CH_2)_w$S—, —$(CH_2)_w$NH—, —C(O)N(H)$(CH_2CH_2O)_w$$CH_2CH_2$NH, —C(O)$(CH_2CH_2O)_w$$CH_2CH_2$NH—, —C(O)N(H)$(CH_2)$NHC(O)CH$(CH_3)$$(CH_2)_w$NH—, or —N(H)$(CH_2)_w$NH—, where w is an integer ranging from 1 to 12; and wherein the wavy line indicates covalent linkage point of the heterobifunctional linker or the polyamine linker.

13. The conjugate of claim 12, wherein the rhodamine or the derivative or the analog thereof and the Cy5 or the derivative or the analog thereof are conjugated to the tissue reactive moiety through a multi-functional linker, wherein the multi-functional linker comprises a molecular weight ranging from between about 50 g/mol to about 300 g/mol.

14. The conjugate of claim 13, wherein the multi-functional linker is derived from lysine or a derivative or analog thereof.

15. The conjugate of claim 12, wherein the rhodamine or the derivative or the analog thereof comprises rhodamine 800.

16. A multi-dye conjugate comprising a tissue reactive moiety and at least two different chromophores, wherein the tissue reactive moiety is a quinone methide precursor moiety and the multi-dye conjugate produces a green or green-like color; wherein the at least two different chromophores of the multi-dye conjugate are covalently conjugated to a heterobifunctional linker or a polyamine linker having between 2 and 10 amine groups, and wherein the heterobifunctional linker or the polyamine linker is covalently conjugated to the quinone methide precursor moiety; and wherein the quinone methide precursor moiety has the structure of Formula (II):

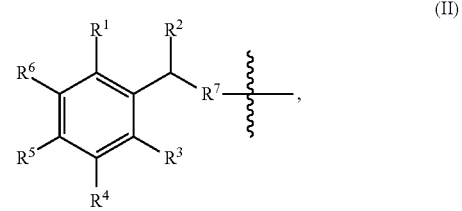

(II)

wherein $R^1$ is a group selected from phosphate, amide, nitro, urea, sulfate, methyl, ester, beta-lactam, or a sugar;

$R^2$ is a halide;

$R^3$, $R^4$, $R^5$, and $R^6$ are independently selected from hydrogen or an aliphatic group having between 1 and 4 carbon atoms; and $R^7$ is -$(CH_2)_w$NH—, —O$(CH_2)_w$NH—, —N(H)C(O)$(CH_2)_w$NH—, —C(O)N(H)$(CH_2)_w$NH—, —$(CH_2)_w$O—, —O$(CH_2)_w$O—, —O$(CH_2CH_2O)_w$—, —N(H)C(O)$(CH_2)_w$O—, —C(O)N(H)$(CH_2)_w$O—, —C(o)N(H)$(CH_2CH_2O)_w$—, -$(CH_2)_w$S—, —O$(CH_2)_w$S—, —N(H)C(O)$(CH_2)_w$S—, —C(O)N(H)$(CH_2)_w$S—, —$(CH_2)_w$NH—, —C(O)N(H)$(CH_2CH_2O)_w$$CH_2CH_2$NH, —C(O)$(CH_2CH_2O)_w$$CH_2CH_2$NH—, —C(O)N(H)$(CH_2)$NHC(O)CH$(CH_3)$$(CH_2)_w$NH—, or —N(H)$(CH_2)_w$NH—, where w is an integer ranging from 1 to 12; and wherein the wavy line indicates covalent linkage point of the heterobifunctional linker or the polyamine linker.

17. The multi-dye conjugate of claim 16, wherein a first of the at least two different chromophores has a yellow or yellow-like color, and wherein a second of the at least two different chromophores has a cyan or a cyan-like color.

18. The multi-dye conjugate of claim 17, wherein the first of the at least two different chromophores comprises rhodamine or a derivative or an analog thereof.

19. The multi-dye conjugate of claim 18, wherein the second of the at least two different chromophores comprises a cyanine dye or a derivative or an analog thereof.

20. A conjugate comprising (i) quinone methide precursor moiety, (ii) a rhodamine or a derivative or an analog thereof, and (iii) a cyanine-based chromogen or a derivative or an analog thereof; wherein the rhodamine or the derivative or the analog thereof and the cyanine-based chromogen or the derivative or the analog thereof are conjugated to a heterobifunctional linker or a polyamine linker having between 2 and 10 amine groups, and wherein the heterobifunctional linker or the polyamine linker is covalently conjugated to the quinone methide precursor moiety; and wherein the quinone methide precursor moiety has the structure of Formula (II):

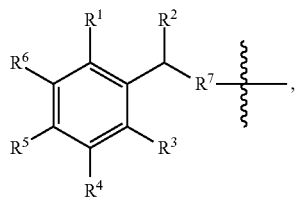

(II)

wherein $R^1$ is a group selected from phosphate, amide, nitro, urea, sulfate, methyl, ester, beta-lactam, or a sugar;

$R^2$ is a halide;

$R^3$, $R^4$, $R^5$, and $R^6$ are independently selected from hydrogen or an aliphatic group having between 1 and 4 carbon atoms; and $R^7$ is —$(CH_2)_w$NH—, —O$(CH_2)_w$NH—, —N(H)C(O)$(CH_2)_w$NH—, —C(O)N(H)$(CH_2)_w$NH—, —$(CH_2)_w$O—, —O$(CH_2)_w$O—, —O$(CH_2CH_2O)_w$—, —N(H)C(O)$(CH_2)_w$O—, —C(O)N(H)$(CH_2)_w$O—, —C(o)N(H)$(CH_2CH_2O)_w$—, —$(CH_2)_w$S—, —O$(CH_2)_w$S—, —N(H)C(O)$(CH_2)_w$S—, —C(O)N(H)$(CH_2)_w$S—, —$(CH_2)_w$NH—, —C(O)N(H)$(CH_2CH_2O)_w$CH_2CH_2NH, —C(O)$(CH_2CH_2O)_w$CH_2CH_2NH—, —C(O)N(H)$(CH_2)$NHC(O)CH$(CH_3)(CH_2)_w$NH—, or —N(H)$(CH_2)_w$NH—, where w is an integer ranging from 1 to 12; and wherein the wavy line indicates covalent linkage point of the heterobifunctional linker or the polyamine linker.

21. The conjugate of claim 20, wherein the rhodamine or the derivative or analog thereof comprises rhodamine 800, and wherein the cyanine-based chromogen comprises Cy5 of a derivative or an analog thereof.

* * * * *